(12) United States Patent
Yan et al.

(10) Patent No.: US 12,187,747 B2
(45) Date of Patent: Jan. 7, 2025

(54) GOLD COMPOSITIONS AND METHODS OF USE THEREOF

(71) Applicant: THE UNIVERSITY OF MASSACHUSETTS, Boston, MA (US)

(72) Inventors: Mingdi Yan, Lowell, MA (US); Bin Wu, Lowell, MA (US); William G. Ndugire, Lowell, MA (US); Olof Ramstrom, Lowell, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 916 days.

(21) Appl. No.: 17/268,845

(22) PCT Filed: Aug. 16, 2019

(86) PCT No.: PCT/US2019/046863
§ 371 (c)(1),
(2) Date: Feb. 16, 2021

(87) PCT Pub. No.: WO2020/037231
PCT Pub. Date: Feb. 20, 2020

(65) Prior Publication Data
US 2021/0198284 A1 Jul. 1, 2021

Related U.S. Application Data

(60) Provisional application No. 62/719,441, filed on Aug. 17, 2018.

(51) Int. Cl.
*C07F 1/00* (2006.01)
*A61P 31/04* (2006.01)

(52) U.S. Cl.
CPC .............. *C07F 1/005* (2013.01); *A61P 31/04* (2018.01)

(58) Field of Classification Search
CPC ...... C07F 1/005; A61K 31/7135; A61K 31/04
USPC ......................................................... 514/24
See application file for complete search history.

(56) References Cited

U.S. PATENT DOCUMENTS

| 2003/0134394 A1 | 7/2003 | Anterim et al. |
| 2018/0020669 A1 | 1/2018 | Charles et al. |

OTHER PUBLICATIONS

Harbut et al, PNAS, 2015, 112(14), 4453-4458.*
Zhang et al, Chinese Chemical Letters, published online Mar. 2, 2018, 29, 687-693.*
Harbut et al, PNAS, Apr. 7, 2015, 112(4), 4453-4458.*
Aguinagalde, Leire et al.; "Auranofin efficacy against MDR Streptococcus pneumoniae and *Staphylococcus aureus* infections"; J Antimicrob Chemother 2015; 70: 2608-2617.
Battisti et al., Preparation, Structure and Reactivity of Polynuclear Gold(I) Phosphanyl Alkanethiolates, European Journal of Inorganic Chemistry, Jan. 12, 2007, pp. 865-875.
Chen, Wei-Yu et al.; "Functional gold nanoclusters as antimicrobial agents for antibiotic-resistant bacteria"; Nanomedicine, V 5, Issue 5, Jul. 2010, p. 1-6.
Gimeno et al, Competitive Gold-Activation Modes in Terminal Alkynes: An Experimental and Mechanistic Study, Chemistry A European Journal, vol. 20, Dec. 6, 2013, pp. 683-688.
Harbut, Michael B. et al.; "Auranofin exerts broad-spectrum bactericidal activities by targeting thiol-redox homeostasis"; PNAS, V 112, No. 14, Apr. 7, 2015, p. 4453-4458.
International Search Report for International Application No. PCT/US2019/046863; International Filing Date: Aug. 16, 2019; Date of Mailing: Dec. 18, 2019; 6 pages.
Pubchem, Substance Record for SID 141574364. Available Date: Aug. 20, 2012 [retrieved on Sep. 24, 2019]. Retrieved from the Internet: <https://pubchem.nci.nim.nih.gov/substance/141574364>. entire document.
Thangamani, Shankar et al.; "Antibacterial activity and mechanism of action of auranofin against multi-drug resistant bacterial pathogens"; Scientific Reportsm V. 6:22571, Mar. 3, 2016, p. 1-13.
Written Opinion for International Application No. PCT/US2019/046863; International Filing Date: Aug. 16, 2019; Date of Mailing: Dec. 18, 2019; 7 Pages.
Xie, Yangzhouyun et al., "Gold Nanoclusters for Targeting Methicillin-Resistant *Staphylococcus aureus* In Vivo", Angew. Chem. Int. Ed. 2018, 57; pp. 3958-3962.
Yanagawa, Akira et al.; "Anti-bacterial and anti-fungal effect of several anti-rheumatic drugs"; vol. 15, No. 3, May 1995, p. 261-264.
Zheng, Kaiyuan et al.; "Antimicrobial Gold Nanoclusters"; ACS Nano, V. 11, 2017, p. 6904-6910.

* cited by examiner

*Primary Examiner* — Ganapathy Krishnan
(74) *Attorney, Agent, or Firm* — CANTOR COLBURN LLP

(57) ABSTRACT

Gold compounds and pharmaceutically acceptable salts thereof are disclosed. Certain compounds and salts are active as antibacterial, antifungal, and/or anti-parasitic agents. The disclosure provides pharmaceutical compositions containing the gold compounds. Methods of using the gold compounds to treat bacterial infections are disclosed.

6 Claims, No Drawings

GOLD COMPOSITIONS AND METHODS OF USE THEREOF

CROSS-REFERENCE TO RELATED APPLICATIONS

This is a U.S. National Phase Application, that claims priority to International Application No. PCT/US2019/046,863, filed on Aug. 16, 2019, that claims priority to U.S. Provisional Application No. 62/719,441, filed on Aug. 17, 2018, the contents of which are herein incorporated by reference in their entirety.

STATEMENT OF GOVERNMENTAL INTEREST

The National Institutes of Health funded the subject matter of this disclosure. The United States Government has certain rights in this application.

BACKGROUND

The increasing prevalence of resistance to the majority of existing antibiotics has generated a pressing global healthcare crisis. To undermine the actions of antibiotics, bacteria have developed powerful resistance mechanisms including mutational alteration of the targeted proteins, loss of membrane porins, enzymes that degrade antibiotics, and overexpression of efflux pumps that drive antibiotics out of the bacterium. Certain highly resistant bacteria have acquired multiple mechanisms against all available antibiotics. The situation is especially dire for Gram-negative bacteria. The recent addition of antibiotics in the clinical pipeline has been limited to treating Gram-positive infections, and there has been no new class of clinically-approved antibiotics for Gram-negative bacteria since the discovery of quinolones in 1968. Untreatable antimicrobial resistance (AMR) is rapidly emerging in, for example, *Escherichia coli, Klebsiella pneumoniae, Pseudomonas aeruginosa* and *Acinetobacter baumannii* that are resistant to all commonly used antibiotics, including fluoroquinolones, β-lactams, macrolides, aminoglycosides, tetracyclines, and the last-resort antibiotic colistin, contributing to the majority of deaths caused by hospital-acquired infections. There is therefore an urgent need to develop novel antibiotics.

SUMMARY

The disclosure includes compounds and salts of Formula IA, Formula IB or a pharmaceutically acceptable salt thereof where

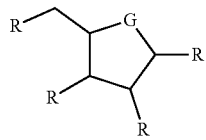

(Formula IA)

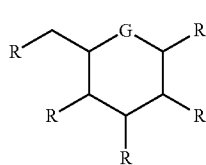

(Formula IB)

G is NR, O, S, or CRR; each instance of R is independently chosen from

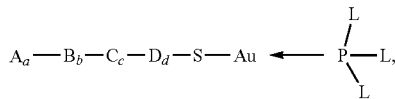

hydrogen, halogen, hydroxyl, aryl, amino, mono-alkylamino, di-alkylamino, —S-alkyl, $C_1$-$C_3$alkyl, —O—$C_1$-$C_3$alkyl, —C(O)alkyl, —C(O)OH, —C(O)Oalkyl, or —NH—C(O)alkyl, which alkyl can contain one or more double or triple bonds and which any H of an alkyl can be substituted with one hydroxyl or one or more halogens; each instance of L is independently chosen from alkyl, $C_0$-$C_4$alkyl(cycloalkyl), or $C_0$-$C_4$alkyl(aryl), which alkyl can contain one or more double or triple bonds, which L can be optionally substituted with one or more substituents independently chosen from halogen, or —O-alkyl, which alkyl can contain one or more triple bonds and any H of an alkyl can be substituted with one hydroxyl or one or more halogens, and A is —NH—, —O—, —S—, —S(O)—, —$SO_2$—, —NHC(O)—, O—C(O)—, —S—C(O)—, —NHC(O)O—, O—C(O)O—, —S—C(O)O—, —NHC(O)NH—, O—C(O)NH—, —S—C(O)NH—, —NHC(O)S—, O—C(O)S—, —S—C(O)S—; B is $C_1$-$C_6$alkyl, which alkyl can contain one or more double or triple bonds; C is NH, O, or S; D is alkyl, aryl, or cycloalkyl, which D is optionally substituted with one or more substituents independently chosen from halogen, hydroxyl, alkyl, or —O-alkyl, which alkyl can contain one or more triple bonds and any H of an alkyl can be substituted with one or more halogens; a is 0 to 1; b is 0 to 1; c is 0 to 1; d is 0 to 1; and wherein one instance of R is

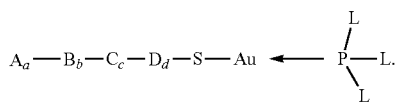

The disclosure includes compounds and salts of Formula IIIA, Formula IIIB or a pharmaceutically acceptable salt thereof where

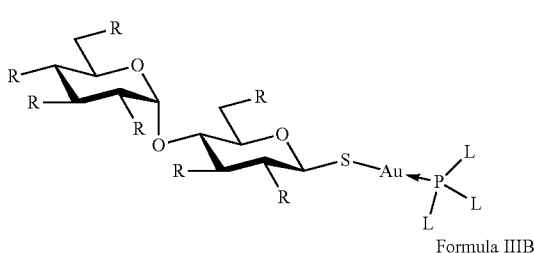

Formula IIIA

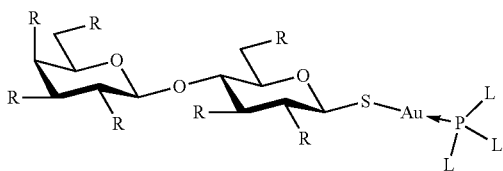

Formula IIIB each instance of R is independently chosen from hydrogen, halogen, hydroxyl, $C_1$-$C_3$alkyl, —O—$C_1$-$C_3$alkyl, —C(O)alkyl, or —NH—C(O)alkyl, which alkyl can contain one or more double or triple bonds and which any H of an alkyl can be substituted with one hydroxyl or one or more halogens; each instance of L is independently chosen from alkyl, $C_0$-$C_4$alkyl(cycloalkyl), or $C_0$-$C_4$alkyl(aryl), which alkyl can contain one or more double or triple bonds, which L can be optionally substituted with one or more substituents independently chosen from halogen, —O— alkyl, or alkyl, which alkyl can contain one or more triple bonds and any H of an alkyl can be substituted with one hydroxyl or one or more halogens.

The disclosure includes compounds and salts of Formula IV or a pharmaceutically acceptable salt thereof where

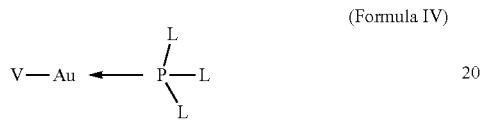

(Formula IV)

V is $C_0$-$C_4$alkyl(cycloalkyl), or $C_0$-$C_4$alkyl(aryl), or alkyl, which alkyl can contain one or more double or triple bonds, which V is optionally substituted with one or more substituents independently chosen from halogen, alkyl, hydroxyl, nitro, —$NH_2$, mono-alkylamino, di-alkylamino, —O-alkyl, —C(O)O-alkyl, —C(O)NH-alkyl, —C(O)N-dialkyl, —O—C(O)alkyl, —NC(O)O-alkyl, or —NHC(O)NH-alkyl, which alkyl can contain one or more double or triple bonds, and which any H of an alkyl can be substituted with one hydroxyl or one or more halogens; and each instance of L is independently chosen from $C_0$-$C_4$alkyl(cycloalkyl), or $C_0$-$C_4$alkyl(aryl), or alkyl, which alkyl can contain one or more double or triple bonds, which L is optionally substituted with one or more substituents independently chosen from halogen, —O-alkyl, or alkyl, which alkyl can contain one or more double or triple bonds and which any H of an alkyl can be substituted with one hydroxyl or one or more halogens.

The disclosure includes compounds and salts of V-A, Formula-B, or Formula V-C or a pharmaceutically acceptable salt thereof where

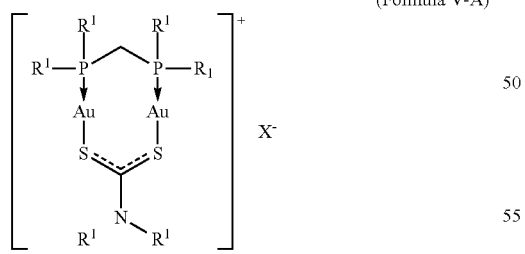

(Formula V-A)

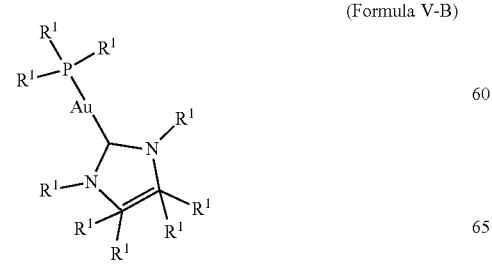

(Formula V-B)

-continued

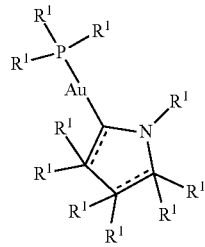

(Formula V-C)

each instance of $R^1$ is independently chosen from hydrogen, $C_0$-$C_4$alkyl(cycloalkyl), $C_0$-$C_4$alkyl(aryl), or alkyl, or $C_0$-$C_4$alkyl($R^2$); each instance of $R^2$ is independently chosen from

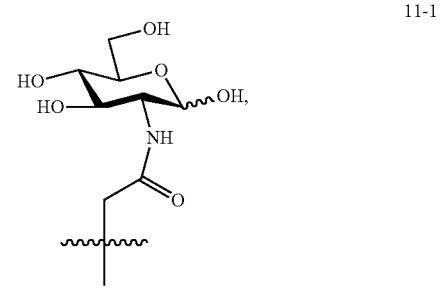

11-1

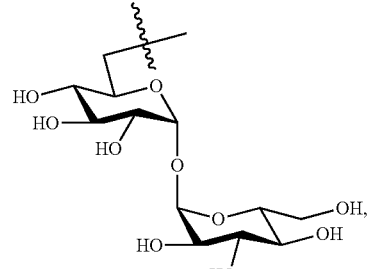

11-2

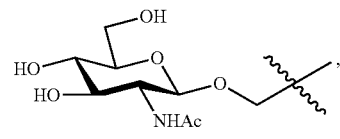

11-3

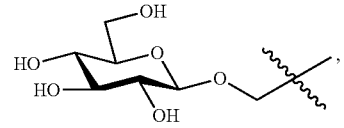

11-4

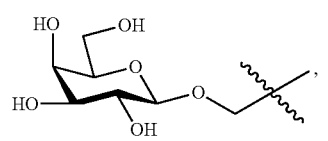

11-5

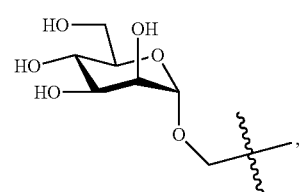

11-6

-continued

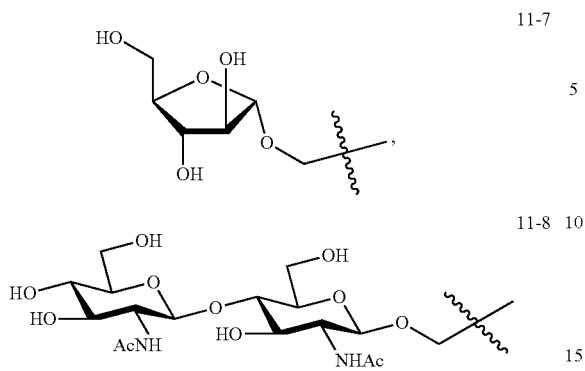

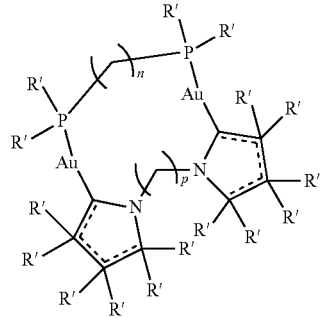

(Formula VI-B)

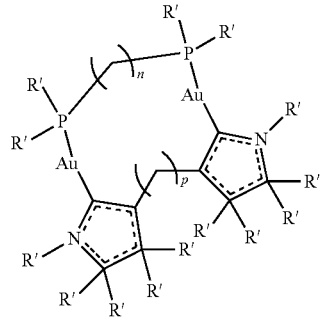

(Formula VI-C)

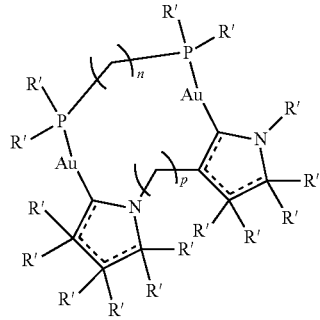

(Formula VI-D)

which alkyl can contain one or more double or triple bonds, which $R^1$ is optionally substituted with one or more substituents independently chosen from halogen, —O-alkyl, or alkyl, which alkyl can contain one or more double or triple bonds and which any H of an alkyl can be substituted with one or more halogens.

The disclosure includes compounds and salts of Formula V-A, Formula V-B and Formula V-C wherein one or more instances of $R^1$ is methyl, ethyl, isopropyl, butyl, aryl, or cyclohexyl.

The disclosure includes compounds and salts of Formula VI-A, Formula VI-B, Formula VI-C, Formula VI-D or a pharmaceutically acceptable salt thereof where

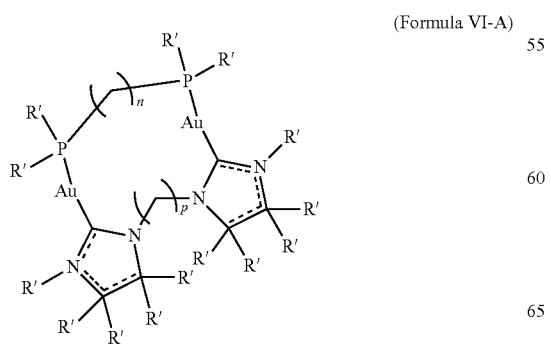

(Formula VI-A)

each instance of R' is independently chosen from hydrogen, $C_0$-$C_4$alkyl(cycloalkyl), $C_0$-$C_4$alkyl(aryl), $C_0$-$C_4$alkyl($R^2$), or alkyl; n is 1 to 4; p is 1 to 4; each instance of $R^2$ is independently chosen from

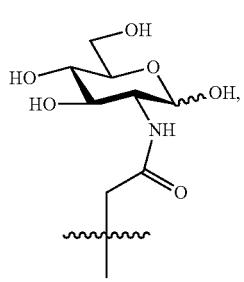

12-1

-continued

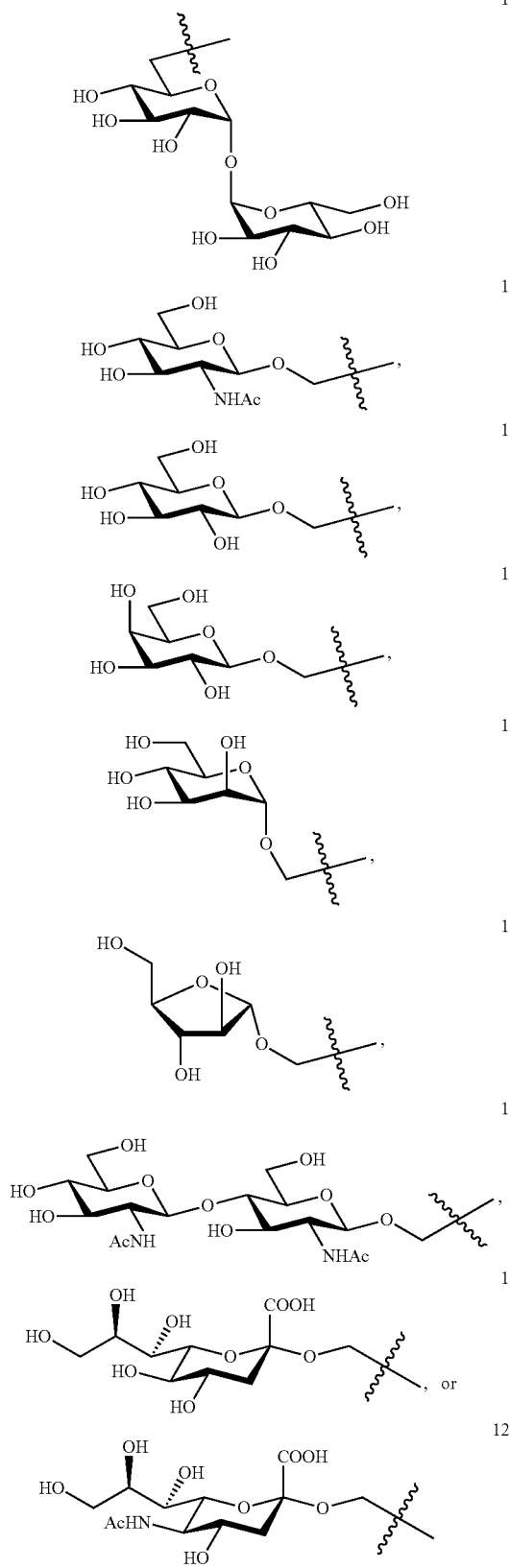

which alkyl can contain one or more double or triple bonds, which R' is optionally substituted with one or more substituents independently chosen from halogen, —O-alkyl, or alkyl which alkyl can contain one or more double or triple bonds and which any H of an alkyl can be substituted with one or more halogens.

The disclosure includes compound or salt of Formula VII or a pharmaceutically acceptable salt thereof where $$Au_a(X)_x(Y)_y(Z)_z \qquad \text{(Formula VII)}$$

X is an aromatic or aliphatic phosphine; Y is a sugar; Z is a $NO_3$ or halogen; a is at least 5; x is 0 to 14; y is 0 to 14; z is 0 to 6; and wherein one of x or y is at least 1.

The disclosure includes a compound or salt of Formula VIII or a pharmaceutically acceptable salt thereof where $$Au_a(X)_x(Y)_y(W)_w(Z)_z \qquad \text{(Formula VIII)}$$

X is an aromatic or aliphatic phosphine; Y is a sugar; W is —$S_2C_2(CN)_2$, —$SC_2H_5$, or —$SC_2H_4Ph$; Z is $NO_3$ or halogen; a is at least 10; x is 0 to 14; y is 0 to 14; w is 0 to 10; z is 0 to 2; and wherein one of x or y is at least 1.

The disclosure includes methods of treating a bacterial infection in a patient comprising administering a therapeutically effective amount of a compound or salt according to any one of the foregoing.

The disclosure includes methods of inhibiting the growth of a bacterium in vitro or in vivo comprising contacting a bacterium with a compound or salt according to any one of the foregoing.

The disclosure includes methods of treating a parasitic infection in a patient comprising administering a therapeutically effective amount of a compound or salt according to any one of the foregoing.

The disclosure includes methods of inhibiting the growth of a parasite in vitro or in vivo comprising contacting a parasite with a compound or salt according to any one of the foregoing.

The disclosure includes methods of treating a fungal infection in a patient comprising administering a therapeutically effective amount of a compound or salt according to any one of the foregoing.

The disclosure includes methods of inhibiting the growth of a fungus in vitro or in vivo comprising contacting a fungus with a compound or salt according to any one of the foregoing.

The disclosure includes pharmaceutical compositions comprising a compound or salt of any of the foregoing together with a pharmaceutically acceptable carrier.

DETAILED DESCRIPTION

Chemical Description and Terminology

Prior to setting forth the invention in detail, it may be helpful to provide definitions of certain terms to be used in this disclosure. Compounds are described using standard nomenclature. Unless defined otherwise, all technical and scientific terms used herein have the same meaning as is commonly understood by one of skill in the art to which this invention belongs. Unless clearly contraindicated by the context each compound name includes the free acid or free base form of the compound as well as all pharmaceutically acceptable salts of the compound.

The term "compounds of Formula ___", for example "compounds of Formula I encompasses all compounds that satisfy the formula, including any enantiomers, racemates and stereoisomers, as well as all pharmaceutically acceptable salts of such compounds. The phrase "a compound of Formula I" includes all subgeneric groups of Formula I (e.g., Formula I-A, Formula I-B, Formula I-C) and also includes pharmaceutically acceptable salts of a compound of Formula I, unless clearly contraindicated by the context in which this phrase is used.

A dash ("-") that is not between two letters or symbols is used to indicate a point of attachment for a substituent. For example, —(C=O)OH is attached through carbon of the keto (C=O) group.

The terms "a" and "an" do not denote a limitation of quantity, but rather denote the presence of at least one of the referenced item. The term "or" means "and/or". The open-ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in any suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

"Alkyl" is a branched or straight chain saturated aliphatic hydrocarbon group, having the specified number of carbon atoms, generally from 1 to about 8 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_4$alkyl and $C_1$-$C_2$alkyl. When $C_0$-$C_n$ alkyl is used herein in conjunction with another group, for example, —$C_0$-$C_4$alkyl(aryl), the indicated group, in this case aryl, is either directly bound by a single covalent bond ($C_0$alkyl), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Cycloalkyl" is a saturated hydrocarbon ring group, having the specified number of carbon atoms. Monocyclic cycloalkyl groups typically have from 3 to about 8 carbon ring atoms or from 3 to 7 (3, 4, 5, 6, or 7) carbon ring atoms. Cycloalkyl substituents may be pendant from a substituted nitrogen, sulfur, oxygen or carbon atom, or a substituted carbon atom that may have two substituents may have a cycloalkyl group, which is attached as a spiro group. Examples of cycloalkyl groups include cyclopropyl, cyclobutyl, cyclopentyl, or cyclohexyl as well as bridged or caged saturated ring groups such as norbornane or adamantine.

"Halo" or "halogen" indicates any of fluoro, chloro, bromo, and iodo.

"Aryl" indicates an aromatic ring, for example, phenyl or a fused aromatic ring system, for example, naphthalene.

"Mono- and/or di-alkylamino" is a secondary or tertiary alkyl amino group, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino.

The term "substituted," as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure.

"Pharmaceutical compositions" are compositions comprising at least one active agent, such as a compound or salt of Formula IA, and at least one other substance, such as a carrier. Pharmaceutical compositions optionally contain one or more additional active agents. When specified, pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like.

The term "carrier" applied to pharmaceutical compositions/combinations of the present disclosure refers to a diluent, excipient, or vehicle with which an active compound is provided. To be pharmaceutically acceptable a carrier must be safe, non-toxic and neither biologically nor otherwise undesirable.

A "patient" is a human or non-human animal in need of medical treatment. Medical treatment can include treatment of an existing condition, such as a disease or disorder, prophylactic or preventative treatment, or diagnostic treatment. In certain embodiments disclosed herein "medical treatment" means treatment of a diagnosed cancer or known tumor. In certain embodiments the patient is a human patient.

"Treatment," as used herein includes providing a compound or salt, either as the only active agent or together with an additional active agent sufficient to: (a) prevent or decrease the likelihood a disease or a symptom of a disease from occurring in a patient who may be predisposed to the disease but has not yet been diagnosed as having it; (b) inhibiting the disease, i.e. arresting its development; and (c) relieving the disease, i.e., causing a remission of the disease.

A "therapeutically effective amount" of a pharmaceutical composition/combination of this disclosure means an amount effective, when administered to a patient, to provide a therapeutic benefit such as an amelioration of symptoms, for example, an amount effective to decrease the symptoms of a bacterial, fungal or parasitic infection.

Chemical Description

The disclosure includes compounds and salts of Formula I and Formula II in which the variables, e.g. G, R, A, B, C, D, a, b, c, d, carry any of the definitions set forth below. Any of the variable definitions set forth below can be combined with any other of the variable definitions so long as a stable compound results.

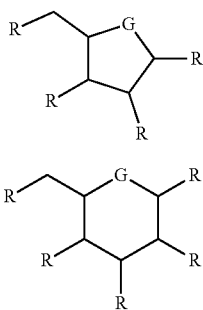

(Formula I)

(Formula II)

G is NR, O, S, or CRR; each instance of R is independently chosen from

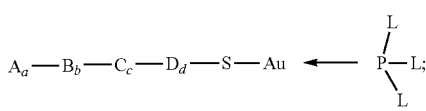

hydrogen, halogen, hydroxyl, aryl, amino, mono-alkylamino, di-alkylamino, —S-alkyl, $C_1$-$C_3$alkyl, —O—$C_1$-$C_3$alkyl, —C(O)alkyl, —C(O)OH, —C(O)Oalkyl, or —NH—C(O)alkyl, which alkyl can contain one or more double or triple bonds and which any H of an alkyl can be substituted with one hydroxyl or one or more halogens; each instance of L is independently chosen from alkyl, $C_0$-$C_4$alkyl(cycloalkyl), or $C_0$-$C_4$alkyl(aryl), which alkyl can contain one or more double or triple bonds, which L can be optionally substituted with one or more substituents independently chosen from halogen, or —O-alkyl, which alkyl can contain one or more triple bonds and any H of an alkyl can be substituted with one hydroxyl or one or more halogens; and A is —NH—, —O—, —S—, —S(O)—, —$SO_2$—, —NHC(O)—, O—C(O)—, —S—C(O)—, —NHC(O)O—, O—C(O)O—, —S—C(O)O—, —NHC(O)NH—, O—C(O)NH—, —S—C(O)NH—, —NHC(O)S—, O—C(O)S—, —S—C(O)S—; B is $C_1$-$C_6$alkyl, which alkyl can contain one or more double or triple bonds; C is NH, O, or S; D is alkyl, aryl, or cycloalkyl, which D is optionally substituted with one or more substituents independently chosen from halogen, hydroxyl, alkyl, or —O-alkyl, which alkyl can contain one or more triple bonds and any H of an alkyl can be substituted with one or more halogens; a is 0 to 1; b is 0 to 1; c is 0 to 1; d is 0 to 1; and wherein one instance of R is

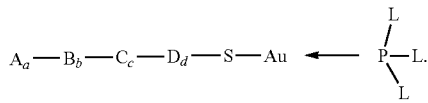

Formula I also includes subformulae I-A, I-B, and I-C.

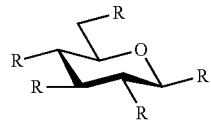

(Formula I-A)

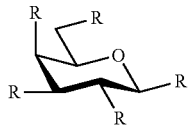

(Formula I-B)

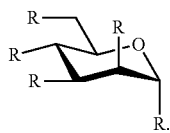

(Formula I-C)

Some embodiments of a compound or salt of Formula I or Formula II can have no more than three R groups that are —O—C(O)alkyl.

Some embodiments of a compound or salt of or Formula II can have least three R groups that are —O—C(O)alkyl.

Some embodiments of a compound or salt of Formula I or Formula II can have four R groups that are —O—C(O)alkyl.

The disclosure includes oligosaccharides comprising a compound or salt of Formula I and/or Formula II.

The disclosure includes polysaccharides comprising a compound or salt of Formula I and/or Formula II.

The disclosure includes compounds and salts of Formula III-A to III-C in which the variables, e.g. R, L, carry any of the definitions set forth below. Any of the variable definitions set forth below can be combined with any other of the variable definitions so long as a stable compound results.

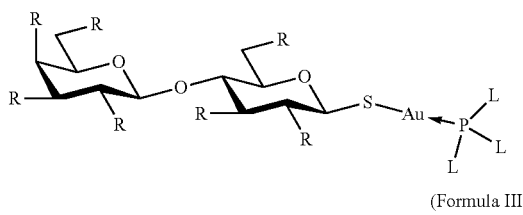
(Formula III-A)

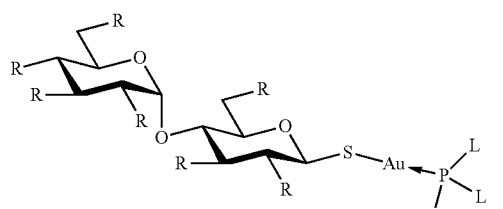
(Formula III-B)

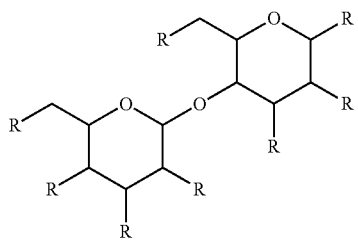
(Formula III-C)

each instance of R is independently chosen from hydrogen, halogen, hydroxyl, $C_1$-$C_3$alkyl, —O—$C_1$-$C_3$alkyl, —C(O)alkyl, or —NH—C(O)alkyl, which alkyl can contain one or more double or triple bonds and which any H of an alkyl can be substituted with one hydroxyl or one or more halogens; each instance of L is independently chosen from alkyl, $C_0$-$C_4$alkyl(cycloalkyl), or $C_0$-$C_4$alkyl(aryl), which alkyl can contain one or more double or triple bonds, which L can be optionally substituted with one or more substituents independently chosen from halogen, —O— alkyl, or alkyl, which alkyl can contain one or more triple bonds and any H of an alkyl can be substituted with one hydroxyl or one or more halogens.

The disclosure includes the following compounds and their pharmaceutically acceptable salts:

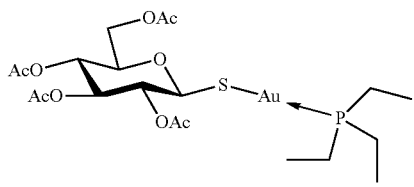
1

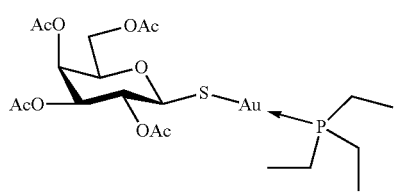
2

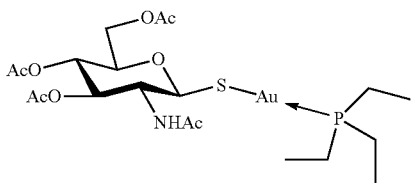
3

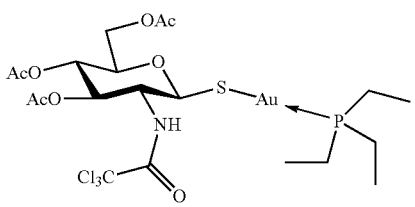
4

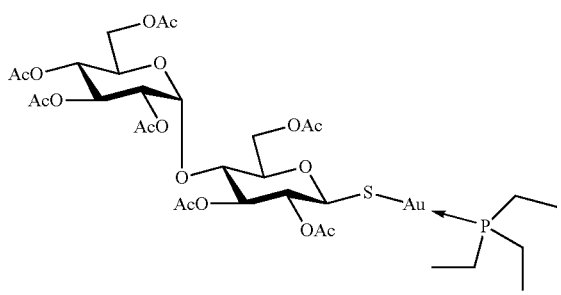
5

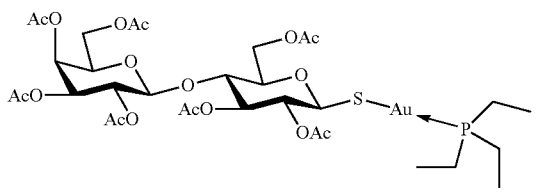
6

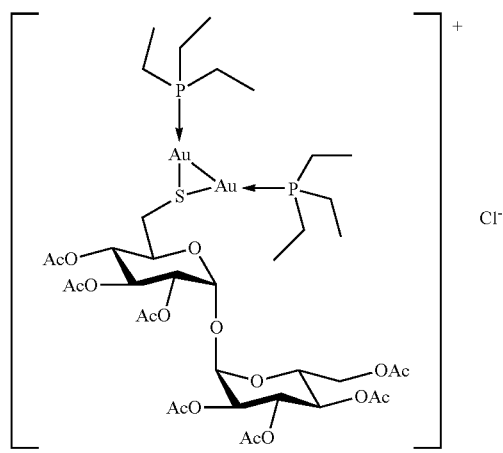
7

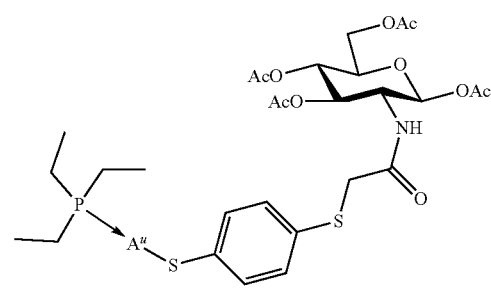
8
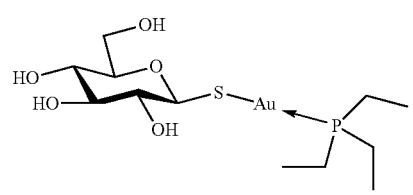
9
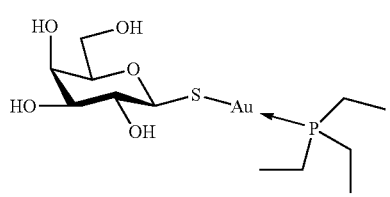
10
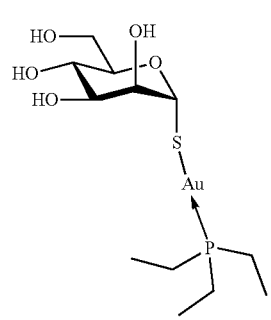
11
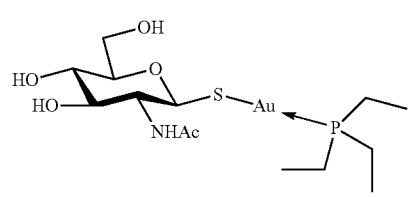
12
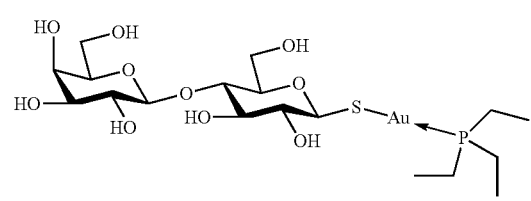
13
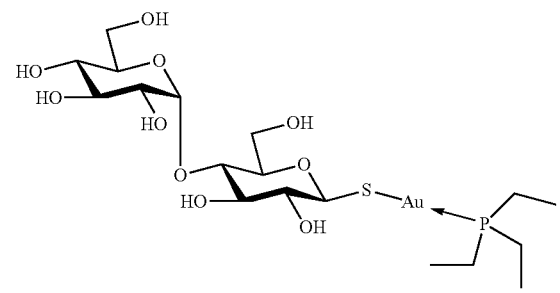
14
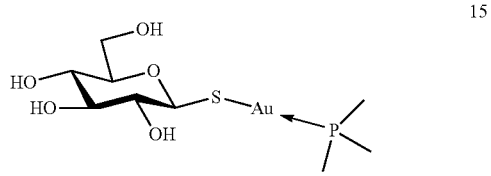
15
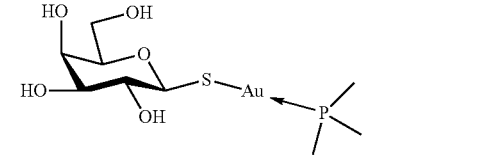
16
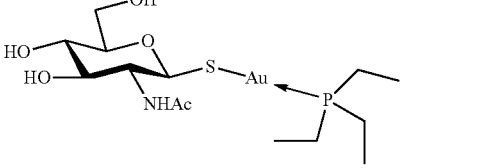
17
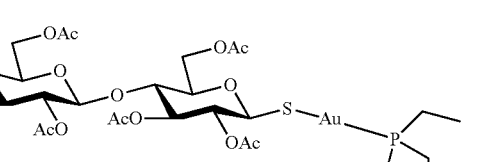
8-1
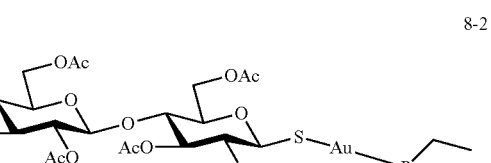
8-2
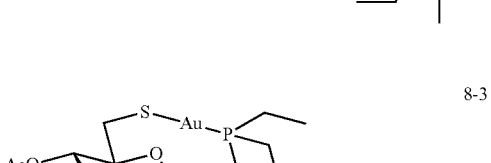
8-3
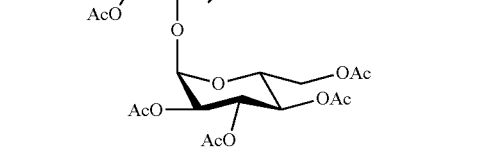

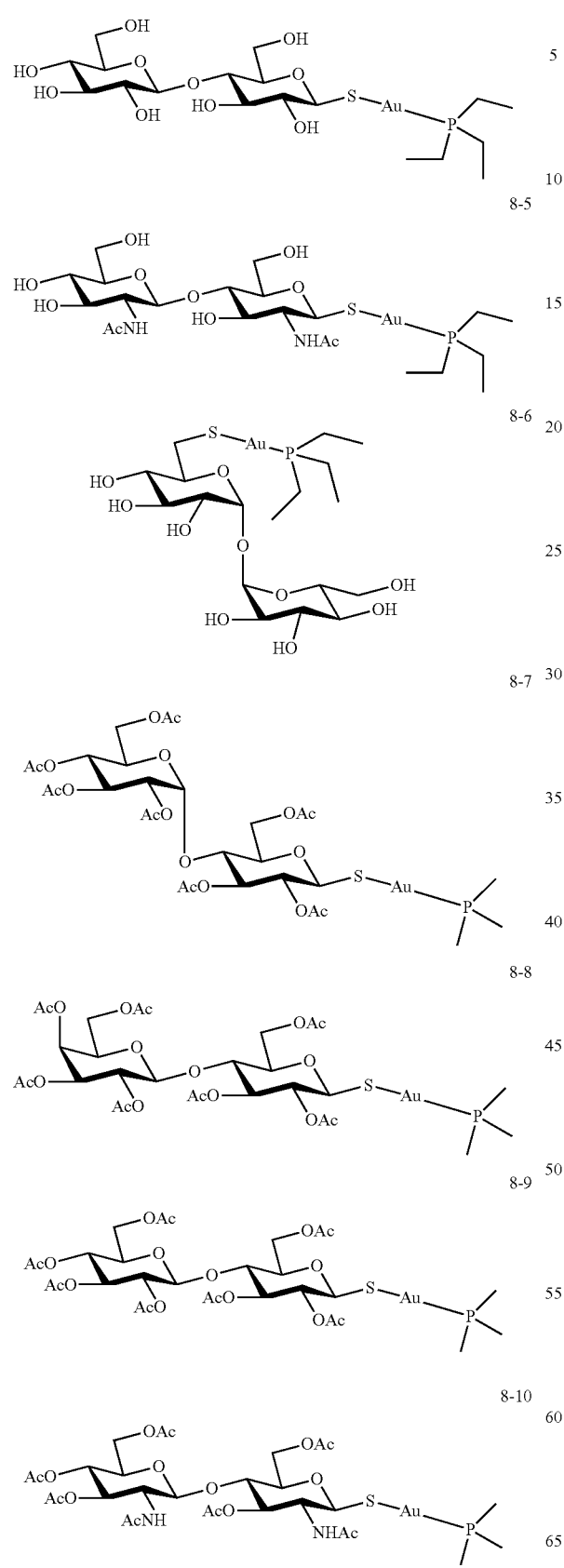
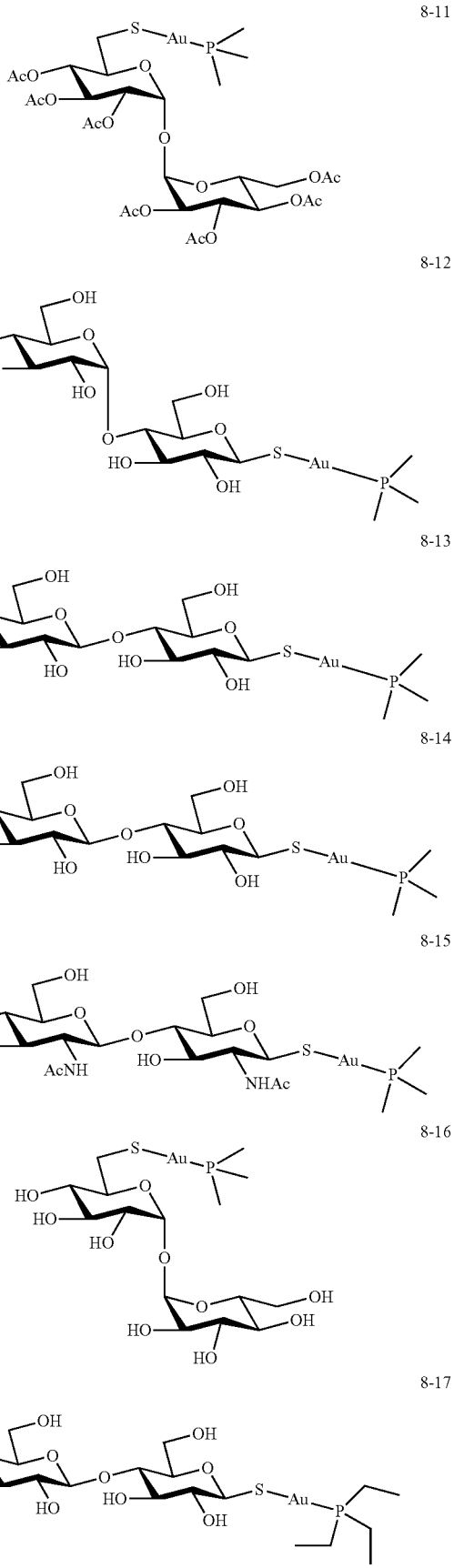

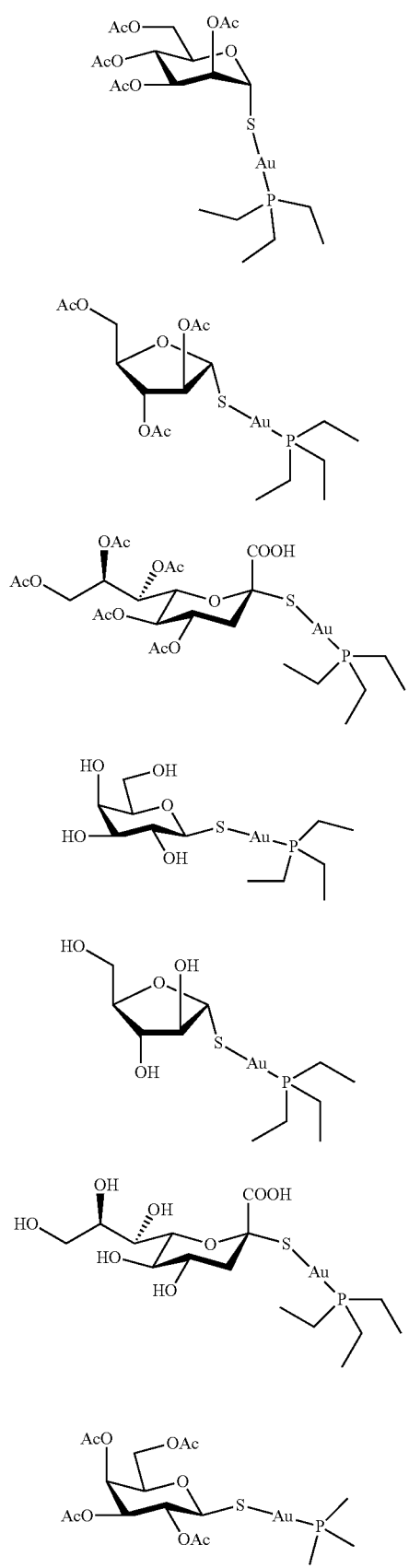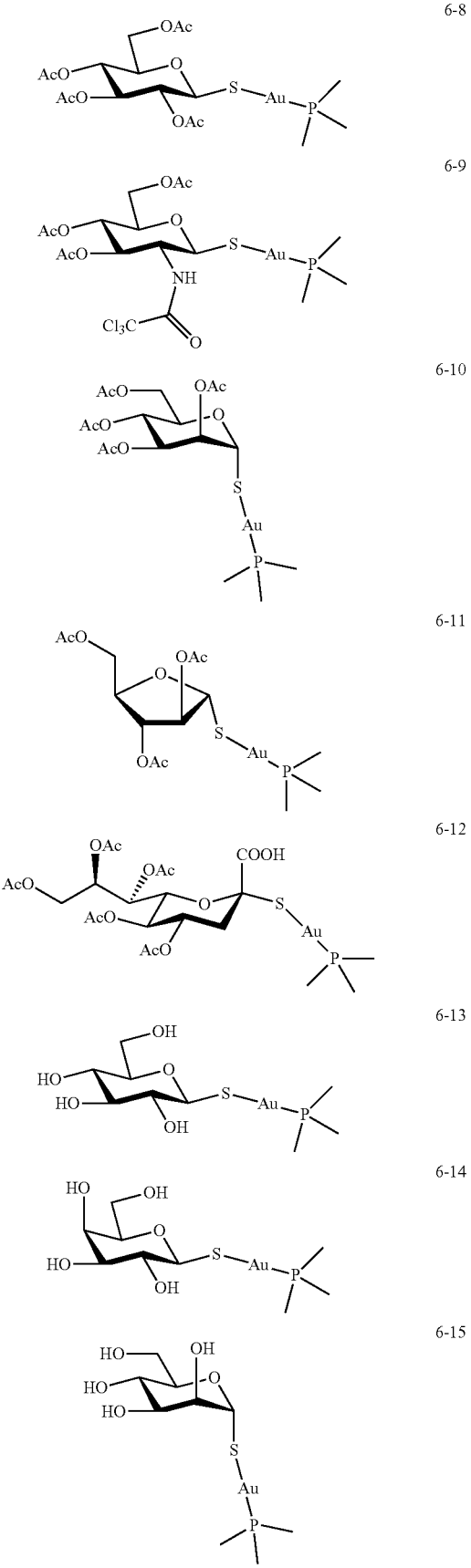

-continued

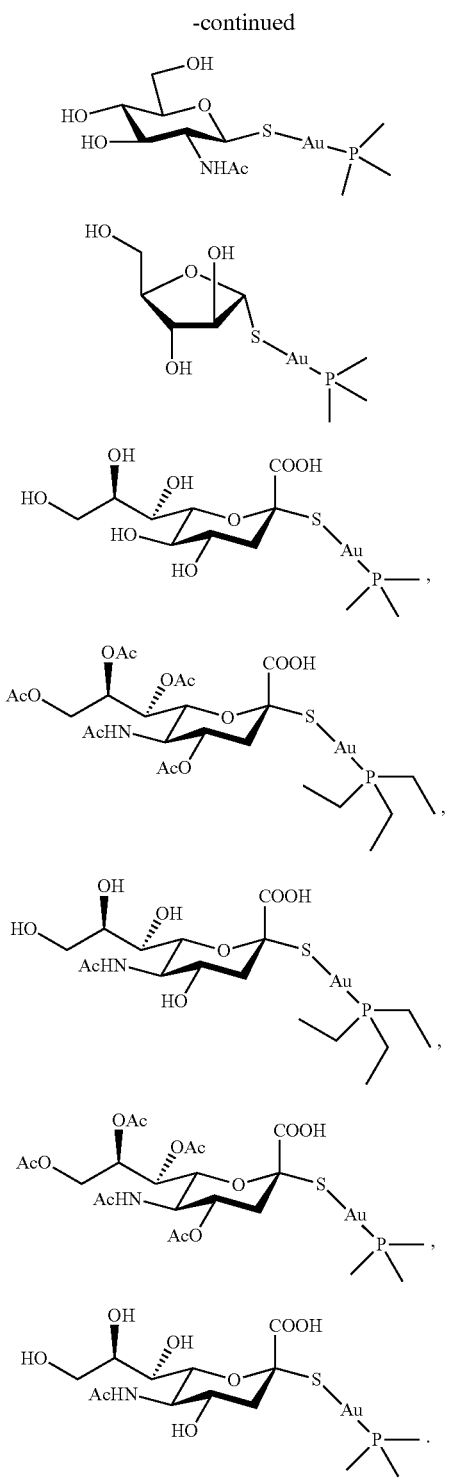

6-16

6-17

6-18

6-19

6-20

6-21

6-22

Auranofin analogs were synthesized by varying the structure of the thio-sugar ligand and the phosphine ligands. These analogs were screened for antimicrobial activity against 5 key ESKAPE pathogens and *E. coli*. (Table 3). The "ESKAPE" pathogens consist of six pathogens with growing multidrug resistant virulence: *Enterococcus faecium* (gram-positive), *Staphylococcus aureus* (gram-positive), *Klebsiella pneumoniae* (gram-negative), *Acinetobacter* (gram-negative), *Pseudomonas aeruginosa* (gram-negative) and *Eterobacter* (gram-negative). According to the data from the Centers for Disease Control and Prevention (CDC), two-thirds of all clinical infections are caused by these six ESKAPE bacteria.

Several thio-sugars were synthesized, replacing Glc in auranofin either as protected (1-8) or unprotected sugars (9-16), including galactose (2, 10), N-acetylglucosamine (GlcNAc, 3, 4, 12), maltose (5, 14), lactose (6, 13) and trehalose (7). GlcNAc is an important component in peptidoglycan cell wall of both Gram-positive and Gram-negative bacteria, and there are GlcNAc sensing proteins that regulate GlcNAc synthesis and catabolism. Maltose is an energy source for *E. coli*. and is actively transported by ATP-binding cassette (ABC) transporters, a complicated process involving binding of maltose to several proteins. There are reports showing that both galactose and lactose can be transported through proton symport. In addition, galactose can be recognized by ATP-dependent ABC transport.

Auranofin 1 showed potent bactericidal activity against: (1) MRSA even at the lowest tested concentration of 0.25 μg/mL; and (2) *S. aureus* and *E. faecalis* even at the lowest tested concentration of 0.5 μg/mL; but lacked significant activity against tested Gram-negative bacteria *P. aeruginosa*, *E. cloacae* and *K. pneumoniae*. Auranofin analogs 2-7 all exhibited activity similar to auranofin 1 against *E. coli, K. pneumonia, P. aeruginosa* and fungi *C. albicans*. This suggests that varying the thio-sugar moiety of 1 has little impact on the antibacterial activity in these strains. Auranofin 1 and 7 exhibited moderate antifungal activity against *C. neoforman* whereas auranofin analogs 2-6 were inactive. Auranofin analog 2 having an acetamide at the C-2 position of the glucose moiety, had a MIC of 4 μg/mL against *A. baumainii*, a gram-negative bacterium, resulting in a value 4 times lower than the auranofin 1.

Compound 3 showed the best results among compounds 1-7. The acetylated sugar moiety can impact the MIC up to 8 fold for gram-negative bacteria. The presence of an electron withdrawing group (NH-acetyl) in the C2-position of the thio-sugar ligand undermines its activity towards gram negative bacteria, as evidenced by the activity of compound 3 when compared to compound 4. Compounds 9 and 11 show activity towards *A. baumanni* and *E. cloacae*. (9 vs 2) The deacetylated galactose moiety shows better activity compared to acetylated form for *E. cloacae*.

The disclosure includes compounds and salts of Formula IV in which the variables, e.g. V, L, carry any of the definitions set forth below. Any of the variable definitions set forth below can be combined with any other of the variable definitions so long as a stable compound results.

(Formula IV)

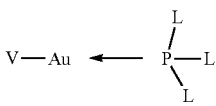

V is $C_0$-$C_4$alkyl(cycloalkyl), or $C_0$-$C_4$alkyl(aryl), or alkyl, which alkyl can contain one or more double or triple bonds, which V is optionally substituted with one or more substituents independently chosen from halogen, alkyl, hydroxyl, nitro, —$NH_2$, mono-alkylamino, di-alkylamino, —O-alkyl, —C(O)O-alkyl, —C(O)NH-alkyl, —C(O)N-dialkyl, —O—C(O)alkyl, —NC(O)O-alkyl, or NC(O)N-alkyl, which alkyl can contain one or more double or triple bonds, and which any H of an alkyl can be substituted with one hydroxyl or one or more halogens; and each instance of L is independently chosen from $C_0$-$C_4$alkyl(cycloalkyl), or $C_0$-$C_4$alkyl (aryl), or alkyl, which alkyl can contain one or more double or triple bonds, which L is optionally substituted with one or more substituents independently chosen from halogen, —O-alkyl, or alkyl, which alkyl can contain one or more double or triple bonds and which any H of an alkyl can be substituted with one hydroxyl or one or more halogens.

The disclosure includes the following compounds.

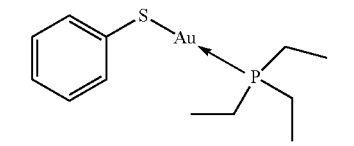

18

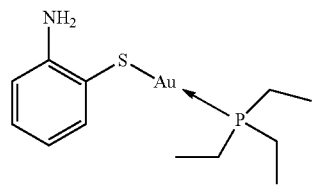

19

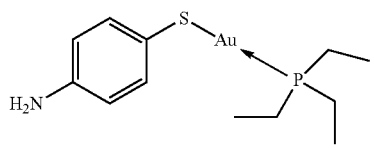

20

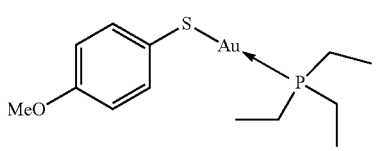

21

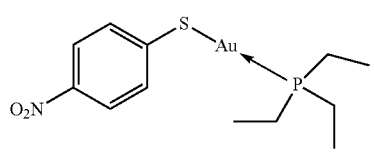

22

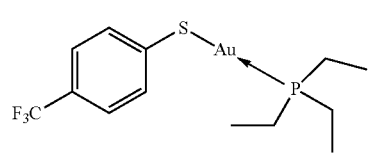

23

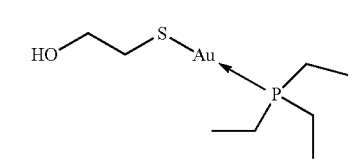

24

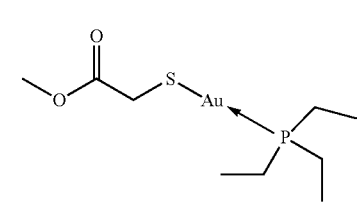

25

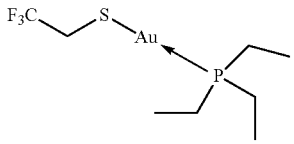

26

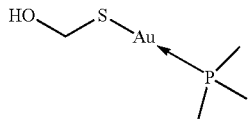

27

The disclosure includes the following compounds.

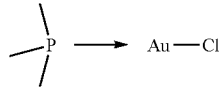

28

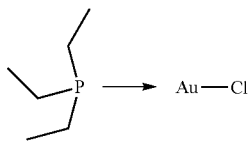

29

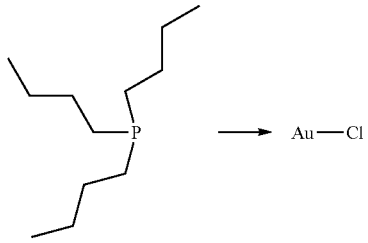

30

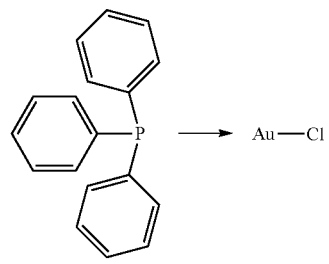

31

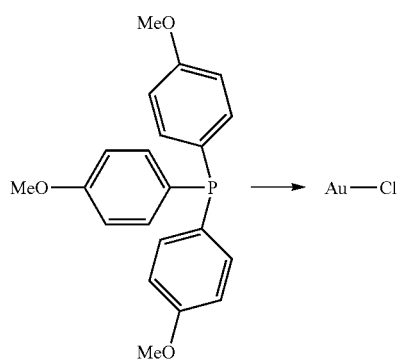

32

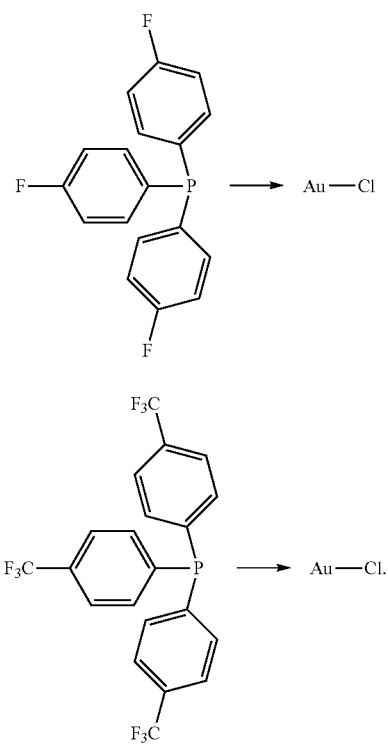

The disclosure includes the following compounds.

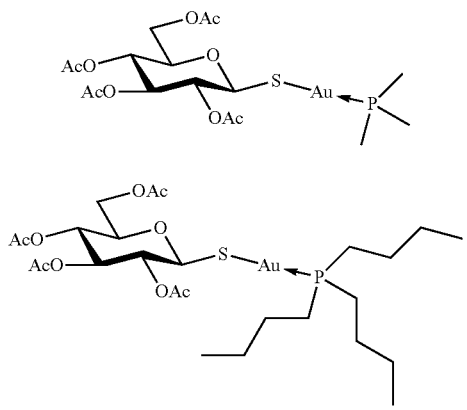

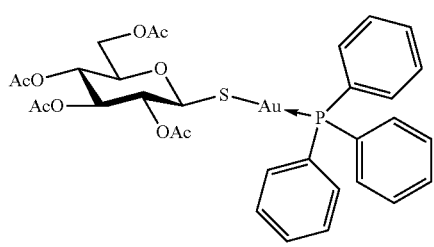

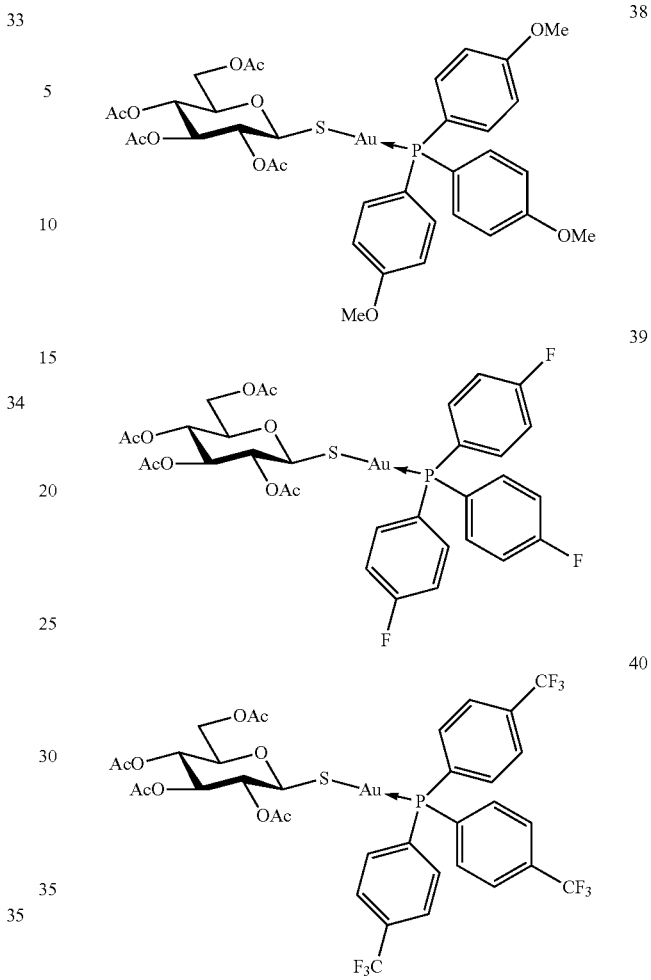

The disclosure includes the compounds and their pharmaceutically acceptable salts of Formula VII in which the variables, e.g. a, X, x, Y, y, Z, z, carry any of the definitions set forth below. Any of the variable definitions set forth below can be combined with any other of the variable definitions so long as a stable compound results.

$$Au_a(X)_x(Y)_y(Z)_z \qquad \text{(Formula VII)}$$

X is an aromatic or aliphatic phosphine; Y is a sugar; Z is $NO_3$ or halogen; a is at least 5; x is 0 to 14; y is 0 to 14; z is 0 to 6; and wherein one of x or y is at least 1.

Formula VII also includes subformulae VII-A, VII-B, VII-C, VII-D, VII-E, VII-F, VI-G, VII-H, VII-I, VII-J, VII-K, VII-L, VII-M, and VII-N (Table 1).

TABLE 1

Gold Clusters of Formula VII.

| Formula | Chemical Formula | x | y | z |
|---|---|---|---|---|
| VII-A | $[Au_5(dppm)_x(Ac_4Glc)_y](NO_3)_z$ | 0-4 | 0-4 | 0-2 |
| VII-B | $[Au_6(TTP)_x(Ac_4Glc)_y](NO_3)_z$ | 0-6 | 0-6 | 0-2 |
| VII-C | $[Au_8(TTP)_x(Ac_4Glc)_y]Z_z$ | 0-8 | 0-8 | 0-3 |
| VII-D | $[Au_9(TTP)_x(Ac_4Glc)_y](NO_3)_z$ | 0-8 | 0-8 | 0-3 |
| VII-E | $Au_{11}(TPP)_x(Ac_4Glc)_yCl_z$ | 0-8 | 0-8 | 0-3 |
| VII-F | $Au_{11}(TPPMS)_xCl_z$ | 0-8 | 0 | 0-3 |
| VII-G | $Au_{13}(dppe)_x(Ac_4Glc)_yCl_z$ | 0-6 | 0-6 | 0-4 |
| VII-H | $[Au_{18}(dppm)_x(Ac_4Glc)_yBr_z]$ | 0-10 | 0-10 | 0-4 |

TABLE 1-continued

Gold Clusters of Formula VII.

| Formula | Chemical Formula | x | y | z |
|---|---|---|---|---|
| VII-I | [Au$_{20}$(PPhpy$_2$)$_x$(Ac$_4$Glc)$_y$Cl$_z$] | 0-10 | 0-10 | 0-4 |
| VII-J | Au$_{39}$(TPP)$_x$(Ac$_4$Glc)$_y$Cl$_z$ | 0-14 | 0-14 | 0-6 |
| VII-K | Au$_{55}$(TPP)$_x$(Ac$_4$Glc)$_y$Cl$_z$ | 0-12 | 0-12 | 0-6 |
| VII-L | Au$_{101}$(TPP)$_x$(Ac$_4$Glc)$_y$Cl$_z$ | 0-21 | 0-21 | 0-5 |
| VII-M | Au$_{101}$(TPPMS)$_x$Cl$_z$ | 0-21 | 0 | 0-5 |
| VII-N | Au$_{101}$(TPPMS)$_x$(Ac$_4$Glc)$_y$Cl$_z$ | 0-21 | 0-21 | 0-5 |

The disclosure includes compounds of Formula VIII or a pharmaceutically acceptable salt thereof in which the variables, e.g. a, X, x, Y, y, W, w, Z, z, carry any of the definitions set forth below. Any of the variable definitions set forth below can be combined with any other of the variable definitions so long as a stable compound results.

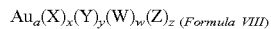

$Au_a(X)_x(Y)_y(W)_w(Z)_z$ (Formula VIII)

X is an aromatic or aliphatic phosphine; Y is a sugar W is —S$_2$C$_2$(CN)$_2$, —SC$_5$H$_5$, or —SC$_2$H$_4$Ph; Z is a NO$_3$ or halogen; a is at least 10; x is 0 to 14, y is 0 to 14, z is 0 to 6; and wherein one of x or y is at least 1.

Formula VIII also includes subformulae VIII-A, VIII-B, VIII-C, and VIII-D as shown in Table 2.

TABLE 2

Gold Clusters of Formula VIII.

| Formula | Chemical Formula | x | y | w | z |
|---|---|---|---|---|---|
| VIII-A | [Au$_{10}$(TTP)$_x$(Ac$_4$Glc)$_y$(S$_2$C$_2$(CN)$_2$)$_2$] | 0-7 | 0-7 | 2 | 0 |
| VIII-B | [Au$_{24}$(TTP)$_x$(Ac$_4$Glc)$_y$(SC$_2$H$_4$Ph)$_5$Cl$_z$] | 0-10 | 0-10 | 5 | 0-2 |
| VIII-C | [Au$_{25}$(TTP)$_x$(Ac$_4$Glc)$_y$(SC$_2$H$_4$)$_5$Cl$_z$] | 0-10 | 0-10 | 5 | 0-2 |
| VIII-D | [Au$_{37}$(TTP)$_x$(Ac$_4$Glc)$_y$(SC$_2$H$_4$Ph)$_{10}$Cl$_z$] | 0-10 | 0-10 | 10 | 0-2 |

The disclosure includes compounds or salts of Formula VII and VIII, wherein X is 17-1

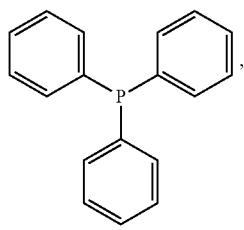

17-2

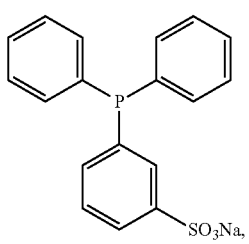

17-3

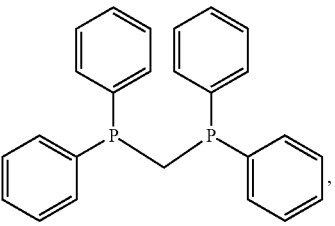

17-4

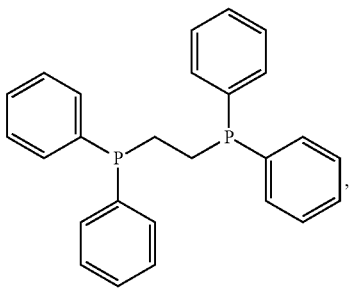

17-5

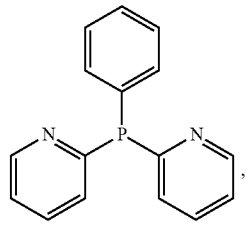

17-6

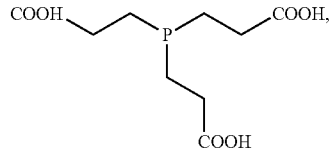

17-7

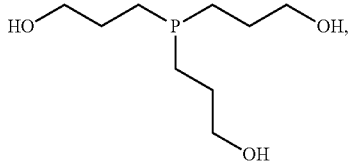

17-8

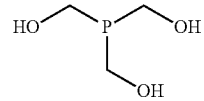

17-9

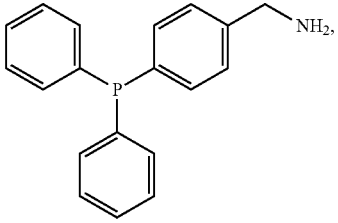

-continued

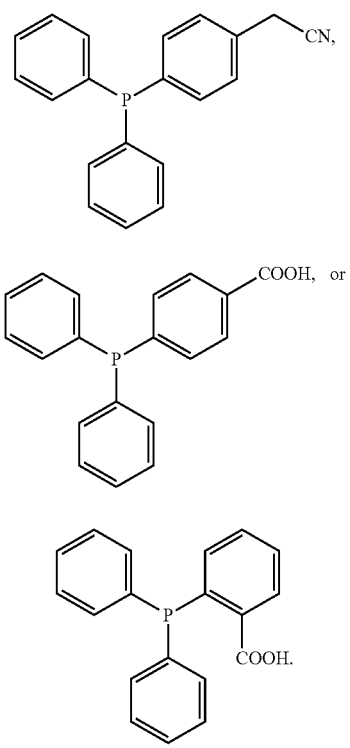

17-10

17-11

17-12

The disclosure includes compounds or salts of Formula VII and VIII, wherein Y is

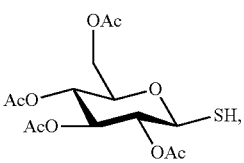

18-1

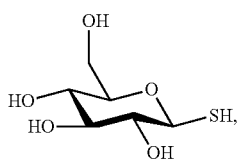

18-2

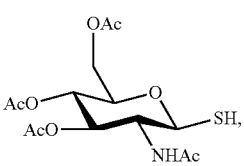

18-3

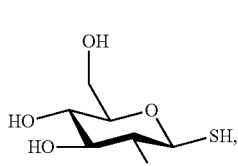

18-4

-continued

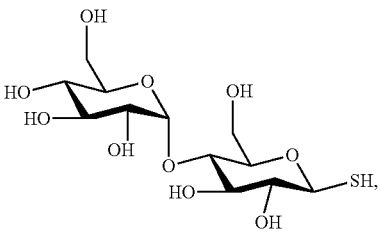

18-5

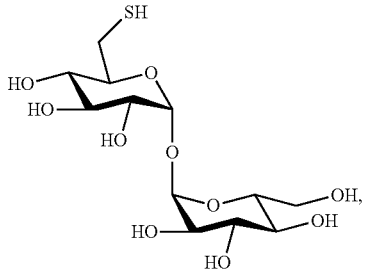

18-6

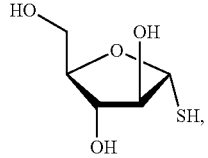

18-7

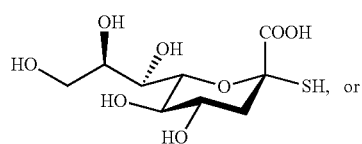

18-8

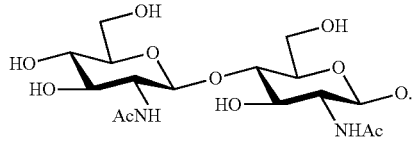

18-9

In some embodiments of Formula VII and Formula VIII, the compound can have a size of about 0.5-50 nanometers (nm), about 0.5-40 nm, about 0.5-30 nm, about 0.5-20 nm, about 0.5-10 nm, about 0.5-5 nm, no more than 3 nm, a size of from about 0.5 to about 3 nm, a size of from about 0.5 to about 2.8 nm, a size of from about 0.5 to about 2.6 nm, a size of from about 0.5 to about 2.4 nm, a size of from about 0.5 to about 2.2 nm, a size of from about 0.5 to about 2.0 nm, a size of from about 0.5 to about 1.8 nm, a size of from about 0.5 to about 1.6 nm, a size of from about 0.5 to about 1.4 nm, or a size of from about 0.5 to about 1.2 nm.

The disclosure includes the following compounds or salts: $Au_5(dppmH)_3(dppm)(NO_3)_2$, $Au_6(PPh_3)_6(NO_3)_2$, $Au_9(PPh_3)_8$, $Au_{11}(PPh_3)_8(NO_3)_3$, $Au_{10}(PPh_3)_7(S_2C_2(CN)_2)$, $[Au_{11}(PPh_3)_8Cl_2]Cl$ (45), $Au_{11}(PPh_3)(Ac_4Glc)$ (46), $[Au_{11}(PPh_3SO_3Na)_8Cl_2]Cl$ (47), $[Au_3(dppe)_5C_2]Cl_3$, $Au_{18}(dppm)_6Br_4$, $Au_{20}(PPhPy_2)_{10}Cl_4$, $Au_{24}(PPh_3)_{10}(SC_2H_4Ph)_5Cl_2$, $Au_2(PPh_3)_{10}(SC_2H)_5Cl_2$, $Au_{37}(PPh_3)_{10}(SC_2H_4Ph)_{10}Cl_2$, $[Au_{39}(PPh_3)_{14}Cl_6]Cl_2$, and $Au_{55}(PPh_3)_{12}Cl_6$, $Au_{101}(PPh_3)_{21}Cl_5$ (41), $Au_{101}(PPh_3)(Ac_4Glc)Cl$ (42), $Au_{101}(PPh_3SO_3Na)_{21}Cl_5$ (43), and $Au_{101}(PPh_3SO_3Na)(Ac_4Glc)Cl$ (44).

The disclosure includes compounds or salts of Formula IX

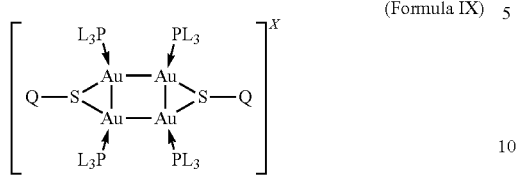

(Formula IX)

wherein each instance of Q is independently chosen from hydrogen, halogen, hydroxyl, aryl, $C_1$-$C_6$alkyl, —O—$C_1$-$C_6$alkyl, —C(O)alkyl, —NH—C(O)alkyl, which alkyl can contain one or more double or triple bonds and which any H of an alkyl can be substituted with one hydroxyl or one or more halogens, or groups 19-1 to 19-24; each instance of L is independently chosen from alkyl, $C_0$-$C_4$alkyl(cycloalkyl), or $C_0$-$C_4$alkyl(aryl), which alkyl can contain one or more double or triple bonds, which L can be optionally substituted with one or more substituents independently chosen from halogen, or —O-alkyl, which alkyl can contain one or more triple bonds and any H of an alkyl can be substituted with one hydroxyl or one or more halogens; and X is a counterion

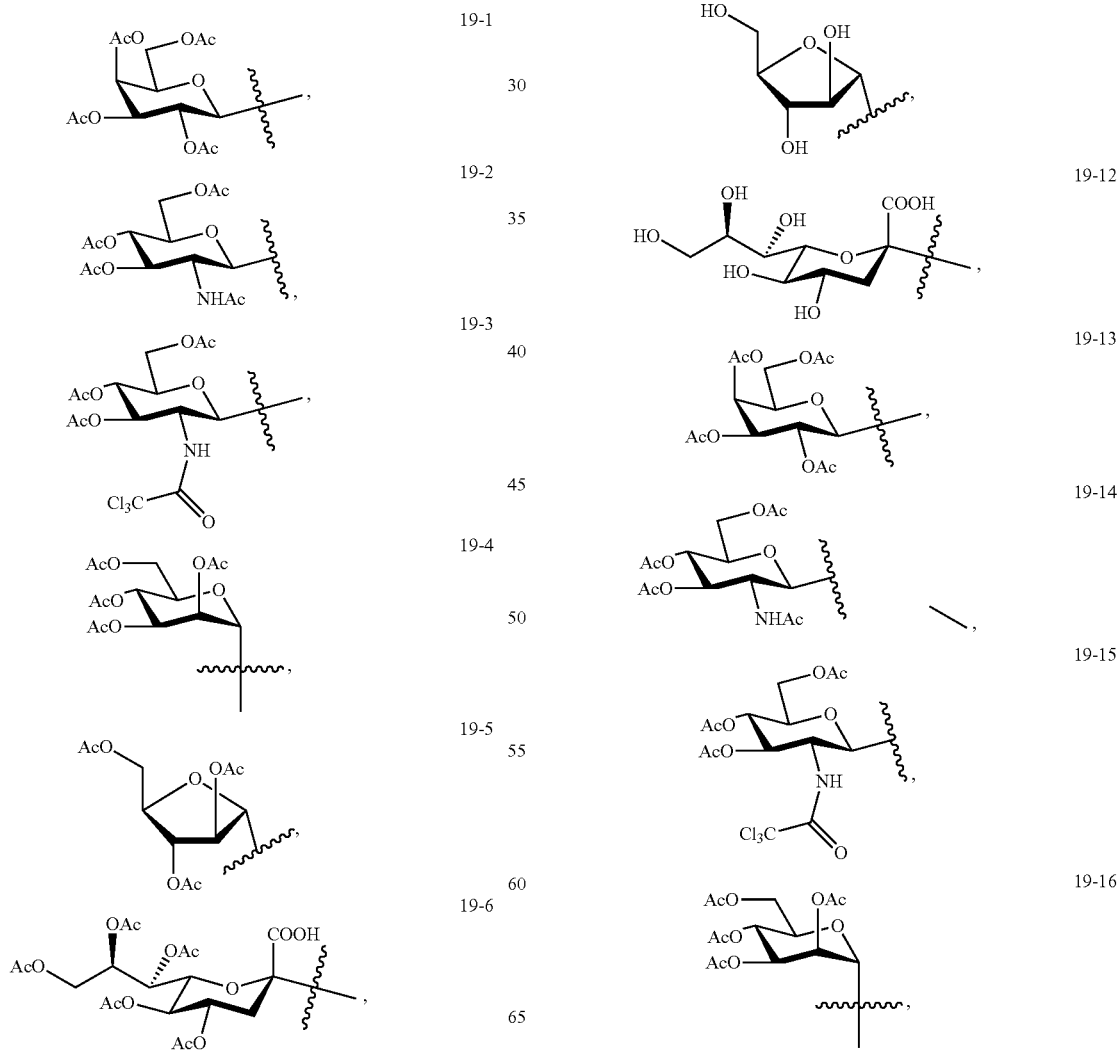

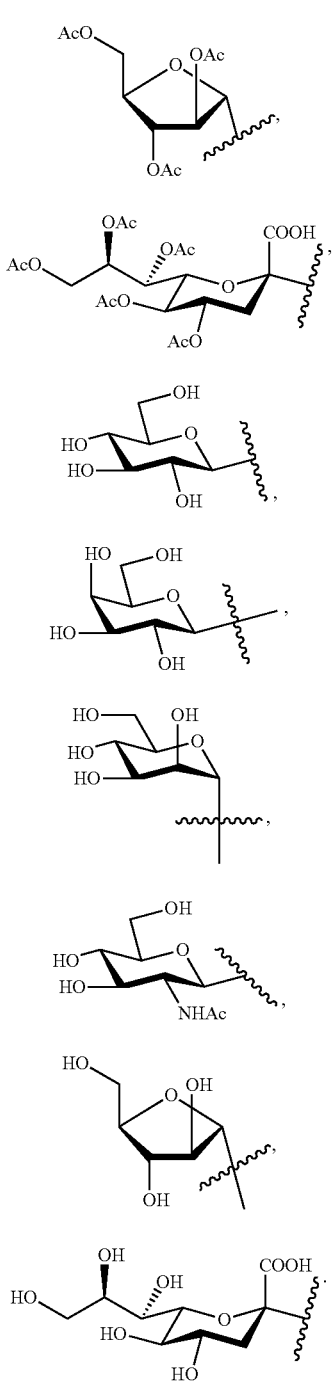

EXAMPLES

Materials

All reagents and solvents were used as received from Sigma Aldrich or Fisher Scientific. All reactions were monitored by thin layer chromatography (TLC) with TLC plates pre-coated with TLC silica gel 60 $F_{254}$ (Merck KGaA, Darmstadt, Germany). Spots on TLC were visualized with ultraviolet light or after stained with 5% $H_2SO_4$ solution in ethanol. NMR spectra were recorded on a Bruker Avance Spectrospin DRX500 spectrometer or a Bruker Avance Spectrospin DPX200 spectrometer. $^1$H NMR and $^{13}$C NMR signals are referenced either to the non-deuterated residual solvent peaks or tetramethyl silane peak (TMS, $\delta$ 0.00 ppm). $CF_3COOH$ (−76.55 ppm) was used as external standard in $^{19}$F NMR. Freshly prepared $Ph_3P$ solution (0.1 M in $CDCl_3$, −6.00 ppm) was used as the external standard in $^{31}$P NMR. HRMS analyses were obtained at University of Illinois at Urbana Champaign Mass Spectroscopy facility.

Example 1

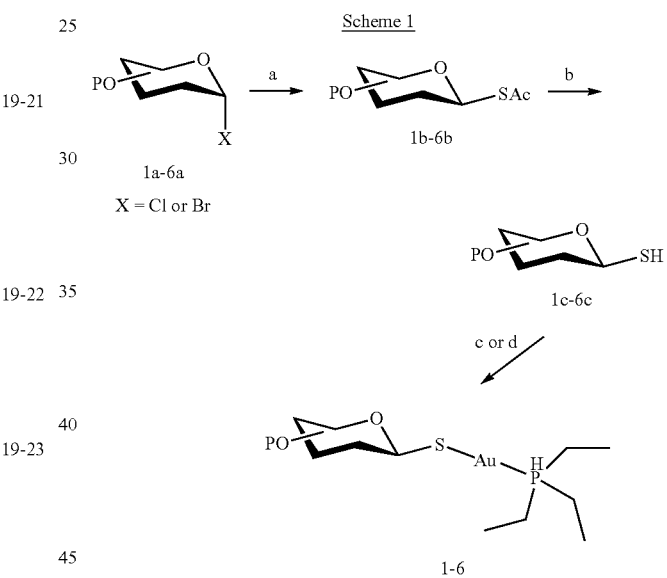

The reagents and conditions used in Scheme are as follows: a KSAc, acetone, RT, 3-4 h, (82~90%); b) DTT, NaHCO$_3$, DMF, RT, 1~1.5 h, (90~95%); c) Et$_3$PAuCl, K$_2$CO$_3$, DCM/H$_2$O, 0~RT, 1~1.5 h, (65~94%).

General procedure A for the synthesis of thiolacetate derivatives 1b-6b. To a solution of glycosyl halide (1.0 equiv.) or triflate in acetone (0.3 M), potassium thioacetate (2.0 equiv.) was added. The reaction mixture was stirred at room temperature (RT) for 3 to 5 h, after which the solvent was removed by rotovap evaporation. Then water was added to the residue. The mixture was extracted with ethyl acetate (EtOAc) 3 times. The combined organic phase was washed by brine, and dried over Na$_2$SO$_4$. After removing the solvent under vacuum at RT, the residue was purified by silica gel chromatography to give thiolacetates 1b-6b.

2,3,4,6-tetra-O-acetyl-1-S-acetyl-1-thio-β-D-glucopyranose (1b). This compound was synthesized from 1a, and purified by column chromatography to give 1b as white solid in 87% yield. $^1$H NMR (500 MHz, CDCl$_3$) δ 5.24-5.14 (m, 2H, H-3, H-1), 5.08-4.97 (m, 2H, H-2, H-4), 4.18 (dd, The disclosure includes methods of treating a bacterial infection in a patient comprising administering a therapeutically effective amount of a compound or salt according to any one of the foregoing. The bacterial infection can be caused by gram-positive bacteria. The bacterial infection can be caused by gram-negative bacteria.

The disclosure includes methods of inhibiting the growth of a bacterium in vitro or in vivo comprising contacting a bacterium with a compound or salt according to any of the foregoing. The bacterium can be a gram-positive bacterium. The bacterial infection can be a gram-negative bacterium.

J=12.5, 4.5 Hz, 1H, H-6a), 4.01 (dd, J=12.5, 2.1 Hz, 1H, H-6b), 3.77 (ddd, J=10.1, 4.4, 2.1 Hz, 1H, H-5), 2.30 (s, 3H, SAc), 1.98 (s, 3H, OAc), 1.94 (s, 3H, OAc), 1.93 (s, 3H, OAc), 1.91 (s, 3H, OAc).

3,4,6-Tri-O-acetyl-N-acetyl-S-acetyl-1-thio-β-D-glucosamine (2b). This compound was synthesized from 2a, and purified by column chromatography to give 2b as pale yellow solid in 88% yield. $^1$H NMR (500 MHz, CDCl$_3$) 5.58 (d, J=9.7 Hz, 1H, NH), 5.15 (d, J=10.8 Hz, 1H, H-1), 5.13 (t, J=9.3 Hz, 1H, H-3), 5.09 (t, J=9.5 Hz, 1H, H-4), 4.35 (q, J=10.0 Hz, 1H, H-2), 4.24 (dd, J=12.5, 4.5 Hz, 1H, H-6a), 4.10 (dd, J=12.5, 2.2 Hz, 1H, H-6b), 3.78 (ddd, J=9.6, 4.5, 2.2 Hz, 1H, H-5), 2.37 (s, 3H, SAc), 2.08 (s, 3H, OAc), 2.03 (s, 6H, OAc×2), 1.92 (s, 3H, OAc).

2,3,4,6-tetra-O-acetyl-1-S-acetyl-1-thio-β-D-galactopyranose (3b). This compound was synthesized from 3a, and purified by column chromatography to give 3b as a viscous solid in 90% yield. $^1$H NMR (500 MHz, CDCl$_3$) 5.46 (d, J=3.3 Hz, 1H, H-4), 5.35-5.29 (t, J=3.3 Hz, 1H, H-2), 5.25 (d, J=10.4 Hz, 1H, H-1), 5.11 (dd, J=9.7, 3.4 Hz, 1H, H-3), 4.18-4.02 (m, 3H, H-6a, H-6b, H-5), 2.39 (s, 3H), 2.15 (s, 3H, SAc), 2.04 (s, 3H, OAc), 2.03 (s, 3H, OAc), 1.98 (s, 3H, OAc).

2,3,4,6-Tetra-O-acetyl-α-D-glucopyranosyl(1→4)-2,3,6-tri-O-acetyl-1-S-acetyl-1-thio-β-D-glucopyranose (4b). This compound was synthesized from 4a, and purified by column chromatography to give 4b as a viscous solid in 82% yield. $^1$H NMR (500 MHz, CDCl$_3$) δ 5.38 (d, J=3.7 Hz, 1H, H-1'), 5.37-5.23 (m, 3H, H-3', H-3, H-1), 5.12-4.90 (m, 2H, H-4', H-2), 4.84 (dd, J=10.4, 4.0 Hz, 1H, H-2'), 4.43 (dd, J=12.3, 2.3 Hz, 1H, H-6a), 4.30-4.12 (m, 2H, H-6b, H-6'a), 4.10-3.72 (m, 4H, H-6'b, H-4, H-5', H-5), 2.36 (s, 3H, SAc), 2.11 (s, 3H, SAc), 2.08 (s, 3H, OAc), 2.04 (s, 3H, OAc), 2.01 (s, 3H, OAc), 1.99 (s, 3H, OAc), 1.99 (s, 6H, OAc×2).

2,3,4,6-Tetra-O-acetyl-β-D-galactopyranosyl(1→4)-2,3,6-tri-O-acetyl-1-S-acetyl-1-thio-β-D-glucopyranose (5b). This compound was synthesized from 5a, and purified by column chromatography to give 5b as a viscous solid in 85% yield. $^1$H NMR (500 MHz, CDCl$_3$) δ 5.35 (dd, J=3.4, 1.0 Hz, 1H, H-4'), 5.25 (t, J=9.1 Hz, 1H, H-3), 5.21 (d, J=10.5 Hz, 1H, H-1), 5.11 (dd, J=10.4, 7.9 Hz, 1H, H-2'), 5.04 (dd, J=10.4, 9.2 Hz, 1H, H-2), 4.94 (dd, J=10.4, 3.5 Hz, 1H, H-3'), 4.46 (d, J=7.9 Hz, 1H, H-1'), 4.45 (dd, J=12.1, 1.9 Hz, 1H, H-6'a), 4.16-4.04 (m, 3H, H-6a, H-6b, H-6'b), 3.89-3.84 (m, 1H, H-5'), 3.82 (dd, J=9.9, 9.0 Hz, 1H, H-4), 3.75 (ddd, J=10.0, 4.7, 1.9 Hz, 1H, H-5), 2.37 (s, 3H, SAc), 2.15 (s, 3H, OAc), 2.11 (s, 3H, OAc), 2.07 (s, 3H, OAc), 2.05 (s, 3H, OAc), 2.04 (s, 3H, OAc), 2.02 (s, 3H, OAc), 1.96 (s, 3H, OAc).

General procedure B for the synthesis of 1c-6c by S-deacetylation. The S-deacetylation was conducted following by a reported method. Briefly, DMF (10 mL) was added to a mixture of thiolacetate derivatives 1b-6b (1.5 mmol), NaHCO$_3$ (0.15 mmol) and DTT (2.5 mmol). The reaction mixture was stirred at RT for 1 h for secondary thiolacetate derivatives, and was stirred at RT for 24 h for primary thiolacetate derivatives under Ar(g) atmosphere. Then the mixture was poured into 100 mL water and extracted with toluene (80 mL×3). The combined organic phase was washed with water (100 mL), and solvent was removed under vacuum. The crude product was used in the next step without further purification.

General procedure C for synthesis of auranofin analogs 1-6. To a solution of derivatives 1c-6c (1.05 mmol) and choro(triethylphosphine)gold(I) (1.0 mmol) in DCM (4 mL), a solution of K$_2$CO$_3$ (1.2 mmol in 4 mL water) was added dropwise at 0° C. The mixture was stirred at RT for 1 h. Then the mixture was poured into 30 mL water, and extracted with DCM (30 mL×3). The combined organic phase was dried with MgSO$_4$ and filtered. After removing the solvent, the residue was purified by column chromatography to give the auranofin analogs 1-6.

General procedure D. To a solution of choro(triethylphosphine)gold(I) (1.0 mmol) and thiols (1.05 mmol) in toluene or DCM (4 mL), DBU (1.2 mmol in 1 mL of toluene or DCM) was added dropwise. The mixture was stirred at RT for 2 h. The mixture was concentrated, after which the residue was purified by column chromatography to give auranofin analogs 8, 18, 19, 21-23, 35-40.

General procedure E. To a solution of thioacetate (0.5 mmol) in methanol (12 mL), NaOMe (0.6 mmol in 1 mL of methanol) was added dropwise at 0° C. The mixture was stirred at RT for 1-4 h, after which chloro(triphosphine)gold (I) (1.0 mmol) was added and the mixture was stirred for another 1 h. The solvent was removed, and the residue was purified by column chromatography to give auranofin analogs 9-17, 20, 24-27, 37-40.

General Procedure F. Thiodiglycol (5 mmol) was added to a solution of gold acid chloride trihydrate (2.5 mmol, in 6 mL of water) dropwise. When the bright orange-yellow solution was almost colorless, it was cooled to 0° C., and triphosphine (2.63 mmol, in DCM/EtOH) was added dropwise. The reaction was stirred at RT for 2 h. 20 mL of DCM and 20 mL of water were added to the mixture, and the aqueous layer was extracted by DCM twice. To remove trace metal impurity in the solution, the combined organic layers was filtered, and 20 mL of EtOH/H$_2$O (v/v 2:1) was added to this filtrate. The solution was slowly concentrated on a rotovap to remove the DCM. A large amount of precipitate formed, which was collected by filtration, washed by cold EtOH/H$_2$O (v/v 1:2), air dried and vacuum dried to give the desired product.

(2,3,4,6-Tetra-O-acetyl-1-thio-β-D-glucopyranosato) (triethylphosphine) gold(I) (Auranofin (1)). This compound was synthesized from compound 1b (450 mg, 1.11 mmol) according to general procedure B to give 400 mg of 1c, which was used to directly prepare compound 1 according to general procedure C. The crude was purified by flash column chromatography (ethyl acetate:hexanes=4:3) to give 1 as a colorless viscous solid (676 mg, 90% over 2 steps). $^1$H NMR (500 MHz, CDCl$_3$) δ 5.11-4.99 (m, 3H, H-1, H-3, H-4), 4.94-4.87 (m, 1H, H-2), 4.17 (dd, J=12.2, 4.8 Hz, 1H, H-6a), 4.03 (dd, J=12.2, 2.3 Hz, 1H, H-6b), 3.66 (ddd, J=9.6, 4.7, 2.3 Hz, 1H, H-5), 2.01 (s, 3H, OAc), 1.98 (s, 3H, OAc), 1.94 (s, 3H, OAc), 1.91 (s, 3H, OAc), 1.79 (dq, J=10.0, 7.6 Hz, 6H, CH$_2$CH$_3$), 1.15 (dt, J=18.5, 7.6 Hz, 9H, CH$_2$CH$_3$).

(2,3,4,6-Tetra-O-acetyl-1-thio-β-D-galacotopyranosato) (triethylphosphine) gold(I) (2). This compound was synthesized from compound 2b (300 mg, 0.824 mmol) according to general procedure B to give 2c (quantitative yield), which was directly used to prepare compound 2 according to general procedure C. The product was purified by flash column chromatography (ethyl acetate:hexanes=4:3) to give 1 as a colorless viscous solid (481 mg, 96% over 2 steps). $^1$H NMR (500 MHz, CDCl$_3$) δ 5.73 (d, J=7.8 Hz, 1H, NH), 5.14 (d, J=9.8 Hz, 1H, H-1), 5.06 (t, J=9.5 Hz, 1H, H-3), 5.02 (t, J=9.5 Hz, 1H, H-4), 4.19 (dd, J=12.2, 4.9 Hz, 1H, H-6a), 4.06 (dd, J=12.1, 2.3 Hz, 1H, H-6b), 4.03 (t, J=9.6 Hz, 1H, H-2), 3.68 (ddd, J=9.6, 4.8, 2.3 Hz, 1H, H-5), 2.01 (s, 3H, OAc), 1.96 (s, 3H, OAc), 1.96 (s, 3H, OAc), 1.93 (s, 3H, OAc), 1.82 (dq, J=9.9, 7.6 Hz, 6H, CH$_2$CH$_3$), 1.17 (dt, J=18.4, 7.6 Hz, 9H, CH$_2$CH$_3$). $^{13}$C NMR (50 MHz, CDCl$_3$) δ 171.04, 170.96, 169.86, 169.68, 84.32, 76.11, 74.99, 69.10, 63.12, 60.50, 23.80, 20.94, 20.90, 20.82, 18.31, 18.31, 18.31, 17.65, 17.65, 17.65, 9.04, 9.04, 9.04. $^{31}$P NMR (81 MHz, CDCl$_3$) δ 36.93.

(3,4,6-Tri-O-acetyl-2-N-acetyl-1-thio-β-D-glucopyranosato)(triethylphosphine) gold (1)(3). This compound was synthesized from 3b (203 mg, 0.5 mmol) according to modified general procedure B using ethyl acetate as extraction solvent instead of toluene. The crude product of 3c was further purified by flash column chromatography (ethyl acetate:hexanes=4:1) to give 3c as a colorless viscous solid (167 mg, 92%). Following general procedure C from 3c (110 mg, 0.303 mmol), and purification using flash column chromatography (ethyl acetate:acetone=200:1), product 3 was obtained as a colorless viscous solid (194 mg, 94%). $^1$H NMR (500 MHz, CDCl$_3$) 5.38 (dd, J=3.5, 1.1 Hz, 1H, H-4), 5.16 (t, J=9.5 Hz, 1H, H-2), 5.11 (d, J=9.4 Hz, 1H, H-1), 4.94 (dd, J=9.6, 3.5 Hz, 1H, H-3), 4.11 (d, J=6.8 Hz, 2H, H-6a, H-6b), 3.92 (td, J=6.8, 1.1 Hz, 1H, H-5), 2.07 (s, 3H, OAc), 2.05 (s, 3H, OAc), 1.99 (s, 3H, OAc), 1.93 (s, 3H, OAc), 1.82 (dq, J=9.9, 7.6 Hz, 6H, CH$_2$CH$_3$), 1.20 (dt, J=18.4, 7.6 Hz, 9H, CH$_2$CH$_3$). $^{13}$C NMR (50 MHz, CDCl$_3$) δ 170.63, 170.38, 170.38, 169.96, 83.86, 74.69, 74.39, 72.30, 68.09, 61.69, 21.40, 20.91, 20.81, 20.81, 18.56, 18.56, 18.56, 17.90, 17.90, 17.90, 9.14, 9.14, 9.14. $^{31}$P NMR (81 MHz, CDCl$_3$) δ 37.57.

(3,4,6-Tri-O-acetyl-2-N-trichloroactyl-1-thio-β-D-glucopyranosato) (triethylphosphine) gold (I) (4). Compound 4b (260 mg, 0.511 mmol), DTT (118 mg, 0.767 mmol) and NaHCO$_3$ (5 mg, 0.0511 mmol) was added to 3 mL of DMF. The mixture was stirred at RT for 1.5 h, and was diluted by 30 mL of toluene and 30 mL of water. The aqueous layer was further extracted by toluene twice. The combined organic layer was dried over Na$_2$SO$_4$. After removing the solvent, the crude product was dissolved in 4 mL of DCM, then Et$_3$PAuCl(162 mg, 0.464 mmol) was added. The reaction was brought to 0° C., then 2 mL of cold K$_2$CO$_3$ solution (35 mg. 0.255 mmol) was added dropwise. The mixture was further stirred at RT for 1.5 h, then it was diluted by 20 mL of DCM and 20 mL of brine. The aqueous layer was further extracted by DCM once more. The combined organic phase was dried over MgSO$_4$. After removal of the solvent, the residue was purified by column chromatography (ethyl acetate:hexanes=1:1) to afford 4 as colorless viscous solid (242 mg, 61% over 2 steps). $^1$H NMR (500 MHz, CDCl$_3$) δ 5.36 (d, J=4.0 Hz, 1H, H-1H-1'), 5.31 (dd, J=10.4, 9.6 Hz, 1H, H-3'), 5.13 (t, J=9.1 Hz, 1H, H-3), 5.12 (d, J=9.6 Hz, 1H, H-1), 5.00 (t, J=9.9 Hz, 1H, H-4'), 4.81 (dd, J=10.5, 4.0 Hz, 1H, H-2'), 4.77 (t, J=9.4 Hz, 1H, H-2), 4.31 (dd, J=12.1, 2.7 Hz, 1H, H-6a), 4.20 (dd, J=12.0, 4.2 Hz, 1H, H-6b), 4.16 (dd, J=12.4, 3.7 Hz, 1H, H-6'a), 4.00 (dd, J=12.4, 2.3 Hz, 1H, H-6'b), 3.98-3.93 (t, J=9.3 Hz, 1H, H-4), 3.91 (ddd, J=10.3, 3.4, 2.6 Hz, 1H, H-5'), 3.66 (ddd, J=9.7, 4.2, 2.9 Hz, 1H, H-5), 2.08 (s, 3H, OAc), 2.05 (s, 3H, OAc), 2.00 (s, 3H, OAc), 2.00 (s, 3H, OAc), 1.97 (s, 3H, OAc), 1.94 (s, 3H, OAc), 1.92 (s, 3H, OAc), 1.80 (dq, J=9.9, 7.6 Hz, 6H, CH$_2$CH$_3$), 1.16 (dt, J=18.5, 7.6 Hz, 9H, CH$_2$CH$_3$). $^{13}$C NMR (50 MHz, CDCl$_3$) δ 170.75, 170.75, 170.64, 170.37, 170.10, 169.99, 169.56, 95.65, 82.83, 78.24, 76.03, 73.53, 70.03, 69.51, 68.50, 68.18, 64.13, 61.60, 21.28, 21.16, 21.12, 21.08, 20.72, 20.72, 20.72, 18.42, 18.42, 18.42, 17.75, 17.75, 17.75, 9.05, 9.05, 9.05. $^{31}$P NMR (81 MHz, CDCl$_3$) δ 36.88.

[2,3,4,6-Tetra-O-acetyl-α-D-glucopyranosyl (1→4)-2,3,6-tri-O-acetyl-1-thio-β-D-glucopyranosato](triethylphosphine) gold(I) (5). This compound was synthesized from 5c (260 mg, 0.398 mmol) according to general procedure C and was purified by flash column chromatography (ethyl acetate:hexanes=2:3) to give 5 as a colorless viscous solid (370 mg, 96%). $^1$H NMR (500 MHz, CDCl$_3$) δ 5.32 (dd, J=3.4, 0.9 Hz, 1H, H-4'), 5.14-5.04 (m, 3H, H-3, H-1, H-2'), 4.92 (dd, J=10.4, 3.5 Hz, 11, H-3'), 4.87 (t, J=9.4 Hz, 1H, H-2), 4.46 (d, J=7.9 Hz, 1H, H-1'), 4.37 (dd, J=11.9, 1.6 Hz, 1H, H-6'a), 4.17-4.00 (m, 3H, H-6a, H-6b, H-6'b), 3.84 (t, J=8.0 Hz, 1H, H-5'), 3.80 (t, J=9.6 Hz, 1H, H-4), 3.62 (ddd, J=9.9, 5.1, 1.7 Hz, 1H, H-5), 2.13 (s, 3H, OAc), 2.08 (s, 3H, OAc), 2.06 (s, 3H, OAc), 2.04 (s, 3H, OAc), 2.02 (s, 3H, OAc), 2.01 (s, 3H, OAc), 1.94 (s, 3H, OAc), 1.83 (dq, J=9.8, 7.6 Hz, 6H, CH$_2$CH$_3$), 1.19 (dt, J=18.4, 7.6 Hz, 9H, CH$_2$CH$_3$). $^{13}$C NMR (50 MHz, CDCl$_3$) δ 170.76, 170.55, 170.37, 170.25, 170.15, 170.04, 169.29, 101.24, 83.01, 77.43, 77.05, 76.87, 74.68, 71.29, 70.73, 69.33, 66.80, 63.42, 60.98, 21.40, 21.16, 21.16, 20.81, 20.81, 20.81, 20.68, 18.50, 18.50, 18.50, 17.84, 17.84, 17.84, 9.10, 9.10, 9.10. $^{31}$P NMR (81 MHz, CDCl$_3$) δ 37.35.

[2,3,4,6-Tetra-O-acetyl-β-D-galactopyranosyl (1→4)-2,3,6-tri-O-acetyl-1-thio-β-D-glucopyranosato](triethylphosphine) gold(I) (6). This compound was synthesized from 6c (300 mg, 0.460 mmol) according to general procedure C and was purified by flash column chromatography (ethyl acetate:hexanes=2:3) to give 6 as a colorless viscous solid (370 mg, 83%). yield. $^1$H NMR (500 MHz, CDCl$_3$) δ 6.47 (d, J=3.2 Hz, 1H, H-1'), 5.56 (d, J=7.9 Hz, 1H, H-1), 5.41 (dd, J=10.5, 9.5 Hz, 1H, H-3'), 5.11 (dd, J=10.6, 4.1 Hz, 1H, H-2'), 5.08 (t, J=9.6 Hz, 1H, H-4'), 4.35 (dd, J=12.0, 2.0 Hz, if, H-6a), 4.22 (dd, J=13.0, 4.1 Hz, 1H, H-6'a), 4.17-4.09 (m, 3H, H-5', H-6b, H-6'b), 3.81-3.75 (m, 1H, H-5), 3.65 (s, 1H, OH), 3.60 (t, J=9.3 Hz, 1H, H-4), 3.44 (t, J=9.8 Hz, 1H, H-3), 3.40-3.34 (dd, J=10.0, 8.1 Hz, 1H, H-2), 2.15 (s, 3H, OAc), 2.13 (s, 3H, OAc), 2.08 (s, 3H, OAc), 2.07 (s, 3H, OAc), 2.02 (s, 3H, OAc), 1.99 (s, 3H, OAc), 1.85 (dq, J=15.4, 7.7 Hz, 6H, CH$_2$CH$_3$), 1.20 (dt, J=18.5, 7.7 Hz, 9H, CH$_2$CH$_3$). $^{13}$C NMR (50 MHz, CDCl$_3$) δ 170.95, 170.76, 170.76, 170.29, 169.78, 169.41, 96.33, 94.37, 81.98, 76.90, 76.12, 70.08, 69.34, 68.69, 68.56, 64.14, 61.92, 54.39, 21.72, 21.37, 21.03, 20.88, 20.84, 20.84, 18.61, 18.61, 18.61, 17.95, 17.95, 17.95, 9.23, 9.23, 9.23. $^{31}$P NMR (81 MHz, CDCl$_3$) δ 38.39.

Example 2

The synthetic scheme for Compound 7 is shown in Scheme 2a.

2,3,2',3',4',6'-O-Acetyl-4,6-di-O-benzylidene-α-D-trehalose (7b). Benzaldehyde dimethyl acetal (1.62 mL, 10.8 mmol), trehalose (2054 mg, 6.0 mmol) and p-toluenesulfonic acid monohydrate (0.23 g, 1.2 mmol) were added to

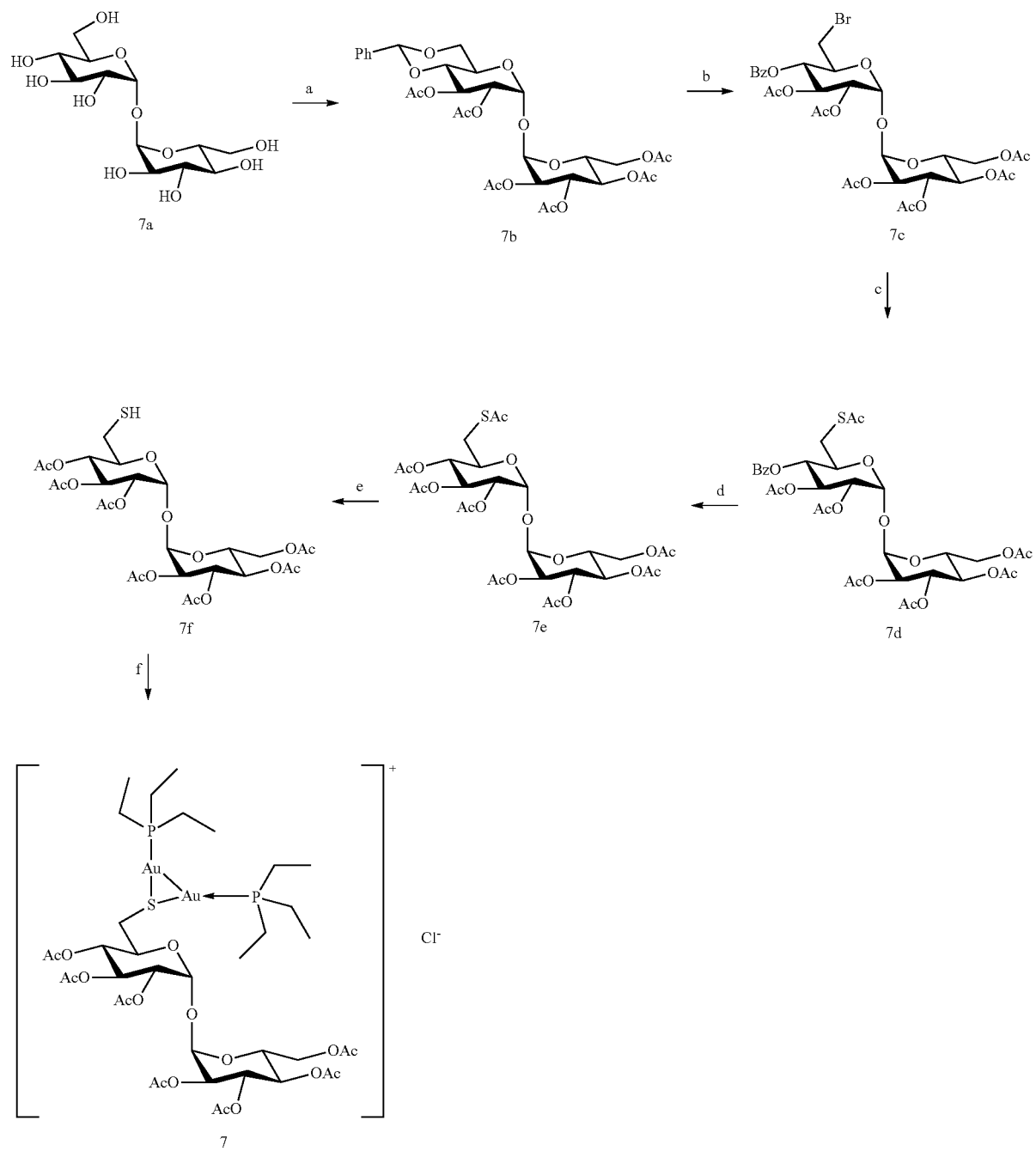

Scheme 2a

Reagents and conditions used in Scheme 2a include: a) i: PhCH(OMe)$_2$, TsOH, DMF; ii Ac$_2$O, Et$_3$N, DMF (40% over 2 steps); b) NBS, CaCO$_3$, CCl$_4$ (89%); c) i: KI, DMF, 60° C.; ii: KSAc, DMF, RT, 8 h, (87%); d) i: NaOMe, MeOH, RT; ii: Ac$_2$O, pyridine, 0° C.-RT, (72%); e) DTT, NaHCO$_3$, DMF, RT, 24 h, (93%); f) Et$_3$PAuCl, DBU, DCM, RT, (62%).

DMF (30 mL). The mixture was stirred for 12 hours at 40° C. After cooling to 0° C., triethylamine (23.60 g, 232.0 mol) and DMAP (122 mg, 1.00 mmol) were added followed by Ac$_2$O (13.0 g, 116.0 mmol) dropwise. The reaction mixture was slowly warmed to RT and stirred overnight, after which it was poured into water, and extracted by ethyl acetate 3 times. The combined organic phase was washed by brine twice, and dried over Na$_2$SO$_4$. After removing the solvent, the residue was purified by column chromatography (ethyl acetate:hexanes=1:1.5~1:1) twice to give the desired product as a white amorphous solid (1.60 g, 40%). $^1$H NMR (500 MHz, CDCl$_3$): δ 7.48-7.38 (m, 2H, Ar—H), 7.38-7.30 (m, 3H, Ar—H), 5.61 (t, J=9.8 Hz, 1H; H-3'), 5.55-5.44 (m, 2H; H-3, PhCH), 5.37 (d, J=3.7 Hz, 1H; H-1'), 5.27 (d, J=3.7 Hz, 1H; H-1), 5.09-5.02 (m, 2H; H-2' and H-4'), 5.00 (dd, J=10.2, 4.0 Hz, 1H, H-2), 4.25 (dd, J=12.2, 5.6 Hz, 1H; H-6a'), 4.17 (dd, J=10.5, 4.9 Hz, 1H; H-6a), 4.09 (ddd, J=10.3, 5.7, 2.2 Hz, 1H; H-5'), 4.01 (dd, J=12.2, 2.2, 1H; H-6b'), 3.97 (td, J=9.9, 4.9 Hz, 1H, H-5), 3.75 (t, J=10.4 Hz; 1H, H-6b), 3.69 (t, J=9.6 Hz, 1H H-4), 2.22-1.96 (m, 18H; OAc). $^{13}$C NMR (126 MHz, CDCl$_3$) δ 170.76, 170.22, 170.03, 169.97, 169.78, 169.78, 136.87, 129.32, 128.41, 126.34, 101.96, 93.49, 92.35, 79.16, 77.43, 70.78, 70.24, 70.16, 69.06, 68.70, 68.28, 63.34, 61.94, 21.01, 20.84, 20.79, 20.79.

4-O-Benzoyl-6-bromo-2,3,2',3',4',6'-penta-O-acetyl-6-deoxy-α,α-D-trehalose (7c). Compound 7b (1.44 g, 2.11 mmol) was added into 60 mL of CCl$_4$ containing N-bromosuccinimide (NBS, 413 mg, 2.32 mmol) and CaCO$_3$ (232 mg, 2.32 mmol). The mixture was refluxed at 77° C. for 3 hours. After cooling to room temperature, the solution was washed with saturated NaHCO$_3$ and water. The organic phase was dried over Na$_2$SO$_4$, and the filtrate was concentrated in vacuo. The residue was purified by flash column chromatography (ethyl acetate:hexanes=2:3) to give 7c as a white solid (1.43 g, 91%). $^1$H NMR (500 MHz, CDCl$_3$): δ 8.15-7.95 (d, J=7.3 Hz, 2H, Ar—H), 7.63 (t, J=7.3 Hz, 1H, Ar—H), 7.49 (t, J=7.7 Hz, 2H, Ar—H), 5.71 (t, J=9.8 Hz, 1H; H-3), 5.54 (t, J=9.7 Hz, 1H; H-3'), 5.41 (d, J=3.9 Hz, 1H; H-1), 5.38 (d, J=3.9 Hz, 1H; H-1'), 5.21-5.00 (m, 4H; H-2, H-4', H-2' and H-4), 4.25 (m, 2H; H-5' and H-6a'), 4.16-3.97 (m, 2H; H-5 and H-6b'), 3.49-3.25 (m, 2H; H-6a and H-6b), 2.28-1.76 (m, 18H; OAc); $^{13}$C NMR (126 MHz, CDCl$_3$) δ 170.81, 170.81, 170.24, 169.73, 169.65, 169.65, 165.59, 134.10, 130.17, 130.17, 128.91, 128.91, 128.65, 92.39, 91.98, 71.82, 70.48, 70.40, 70.29, 69.43, 69.43, 68.80, 68.45, 61.99, 30.75, 21.17, 20.92, 20.90, 20.81, 20.80, 20.78, 20.76.

4-O-Benzoyl-6-S-acetyl-2,3,2',3',4',6'-penta-O-acetyl-α,α-D-trehalose (7d). Compound 7c (2.95 g, 3.87 mmol) and KI (1.93 g, 11.6 mmol) was added to a round bottom flask containing 30 mL of DMF. After stirring at 60° C. for 4 h, the mixture was cooled to RT, and KSAc (1.33 g, 11.6 mmol) was added to the mixture. The reaction was stirred under Ar(g) atmosphere overnight. The resulting mixture was poured into 100 mL brine/100 mL water and extracted with ethyl acetate (100 mL×3). The combined organic layers were further washed with 200 mL brine and dried over MgSO$_4$, concentrated in vacuo. The residue was purified by column chromatography (ethyl acetate:hexanes=1:1) to afford the product as a viscous solid (2.93 g, 96%). $^1$H NMR (500 MHz, CDCl$_3$) δ 8.04 (dd, J=8.3, 1.2 Hz, 1H, Ar—H), 7.60 (t, J=7.5 Hz, 1H, Ar—H), 7.47 (t, J=7.8 Hz, 1H, Ar—H), 5.67 (dd, J=9.8, 9.7 Hz, 1H, H-3), 5.52 (dd, J=9.9, 9.6 Hz, 1H, H-3), 5.34 (d, J=3.9 Hz, 2H, H-1, H-1'), 5.20 (t, J=9.7 Hz, 1H, H-4), 5.13-4.98 (m, 3H, H-2, H-2', H-4'), 4.20 (dd, J=12.2, 6.0 Hz, 1H, H-6a'), 4.07 (dd, J=12.2, 2.1 Hz, 1H, H-6b'), 4.03-3.90 (m, 2H, H-5, H-5'), 3.30 (dd, J=14.2, 2.6 Hz, 1H, H-6a), 2.91 (dd, J=14.5, 9.2 Hz, 1H, H-6b), 2.32 (s, 3H, SAc), 2.11 (s, 3H, OAc), 2.10 (s, 3H, OAc), 2.08 (s, 3H, OAc), 2.05 (s, 3H, OAc), 2.04 (s, 3H, OAc), 1.93 (s, 3H, OAc). $^{13}$C NMR (126 MHz, CDCl$_3$) δ 194.64, 170.73, 170.01, 169.94, 169.85, 169.77, 169.70, 165.66, 133.78, 130.02, 128.95, 128.73, 91.26, 91.12, 72.03, 70.34, 70.31, 69.76, 69.60, 69.53, 68.72, 68.31, 61.93, 30.47, 30.27, 20.80, 20.72, 20.72, 20.72, 20.70, 20.70.

6-S-Acetyl-2,3,4,2',3',4',6'-hexa-O-acetyl-α,α-D-trehalose (7e). Compound 7d (1435 mg, 1.90 mmol) was dissolved in 50 mL methanol. NaOMe (113 mg, 2.09 mmol) in 3 mL methanol was added to the reaction under Ar(g) atmosphere. The reaction mixture was stirred overnight. After removing the solvent under vacuum, 7 mL of pyridine was added followed by addition of acetic anhydride (2.7 mL, 28.5 mmol) dropwise at 0° C. The reaction was stirred for 16 hours at RT. The reaction mixture was diluted with 100 mL ethyl acetate and poured into 100 mL of water. After extraction for 3 times by ethyl acetate, the combined organic layers were washed with 1 M HCl (aq), saturated NaHCO$_3$, water, and brine, and dried over MgSO$_4$. After removing the solvent, the residue was purified by column chromatography (ethyl acetate:hexanes=1:1) to afford the product as a viscous solid (964 mg, 73% over 2 steps). $^1$H NMR (500 MHz, CDCl$_3$) δ 5.44 (t, J=9.7 Hz, 2H, H-4, H-4'), 5.27 (d, J=3.9 Hz, 1H, H-1'), 5.24 (d, J=3.8 Hz, 1H, H-1), 5.05-4.89 (m, 4H, H-2, H-2', H-3, H-3'), 4.16 (dd, J=12.2, 6.0 Hz, 1H, H-6a'), 4.01 (dd, J=12.2, 1.9 Hz, 1H, H-6b'), 3.94 (ddd, J=10.0, 5.9, 1.7 Hz, 1H, H-5'), 3.89-3.80 (m, 1H, H-5), 3.15 (dd, J=14.2, 2.6 Hz, 1H, H-6a), 2.93 (dd, J=14.2, 7.9 Hz, 1H, H-6b), 2.32 (s, 3H, SAc), 2.07 (s, 3H, OAc), 2.06 (s, 3H, OAc), 2.05 (s, 3H, OAc), 2.04 (s, 3H, OAc), 2.02 (s, 3H, OAc), 2.00 (s, 3H, OAc), 2.00 (s, 3H, OAc). $^{13}$C NMR (50 MHz, CDCl$_3$) δ 194.73, 170.69, 169.96, 169.85, 169.83, 169.66, 91.45, 91.31, 71.07, 70.20, 70.12, 69.93, 69.70, 69.48, 68.68, 68.30, 61.92, 30.47, 29.93, 20.76, 20.76, 20.73, 20.67.

Compound 7. Compound 7f was prepared from compound 7e (278 mg, 0.40 mmol) according to general procedure B (24 h) and was purified by flash column chromatography (ethyl acetate:hexanes=2:3) to give 7f as a viscous solid (260 mg, quant). Compound 7 was obtained from 7f (260 mg, 0.40 mmol) following general procedure C, and purified using flash column chromatography (ethyl acetate:hexanes=3:1) to give compound 7 as a colorless viscous solid (230 mg, 60%). $^1$H NMR (500 MHz, CDCl$_3$) δ 5.68 (d, J=3.8 Hz, 1H, H-1'), 5.51-5.44 (m, 2H, H-4, H-4'), 5.25 (d, J=3.9 Hz, 1H, H-1), 5.15 (dd, J=10.3, 3.8 Hz, 1H, H-2'), 4.99 (ddd, J=10.1, 9.1, 6.6 Hz, 3H, H-2, H-3, H-3'), 4.16 (dd, J=12.3, 6.3 Hz, 1H, H-6a), 4.04-3.97 (m, 2H, H-6b, H-5), 3.95-3.88 (m, 1H, H-5'), 2.98 (dd, J=13.7, 2.1 Hz, 1H, H-6'a), 2.88 (dd, J=13.7, 8.5 Hz, 1H, H-6'b), 2.21 (s, 3H, OAc), 2.06 (s, 3H, OAc), 2.04 (s, 3H, OAc), 2.02 (s, 3H, OAc), 2.02 (s, 3H, OAc), 1.99 (s, 3H, OAc), 1.99 (s, 3H, OAc), 1.80 (dq, J=10.0, 7.6 Hz, 12H, CH$_2$CH$_3$), 1.17 (dt, J=18.5, 7.6 Hz, 18H, CH$_2$CH$_3$). $^{13}$C NMR (50 MHz, CDCl$_3$) δ 170.67, 170.19, 170.16, 170.07, 170.07, 170.01, 169.82, 91.87, 91.57, 73.14, 72.16, 70.65, 70.65, 70.41, 69.11, 68.99, 68.94, 68.41, 62.17, 21.54, 20.98, 20.92, 20.83, 20.80, 20.80, 20.74, 18.60, 18.60, 18.60, 17.91, 17.91, 17.91, 9.07, 9.07, 9.07. $^{31}$P NMR (81 MHz, CDCl$_3$) δ 34.68.

The synthetic scheme for Compound 8 is shown in Scheme 2b.

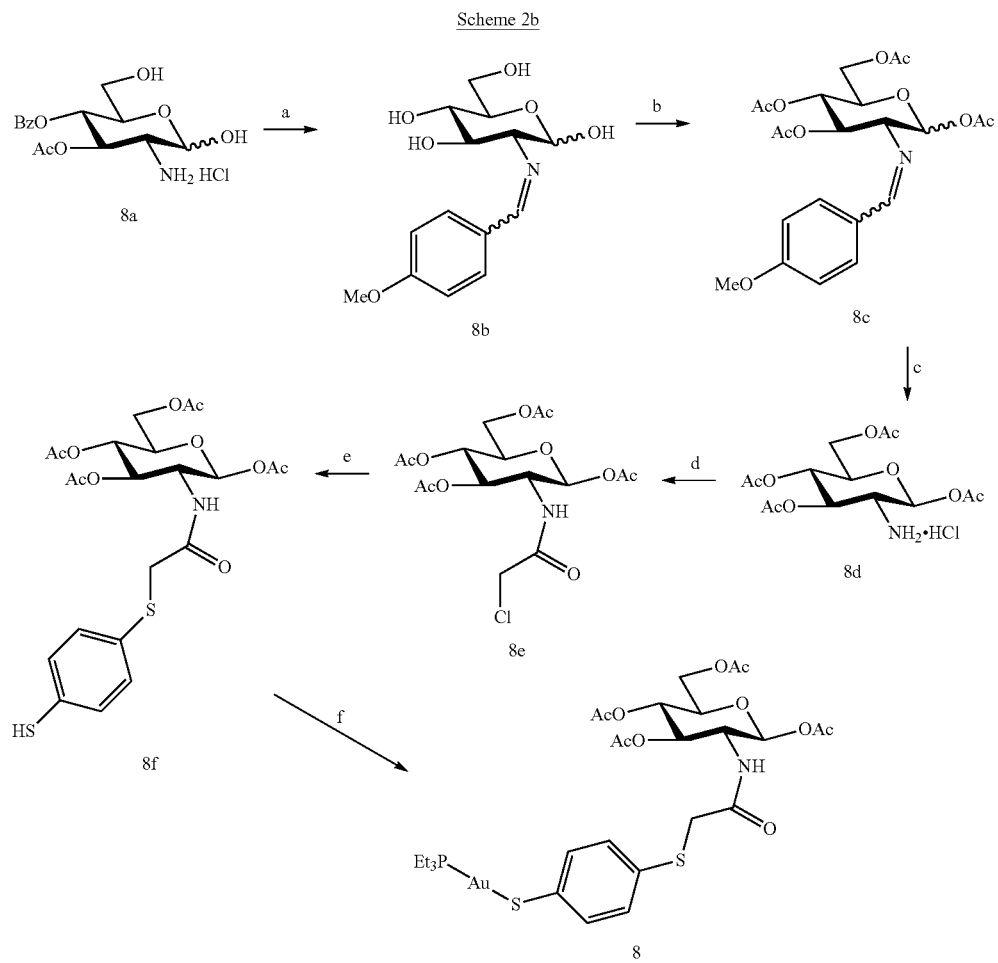

Reagents and conditions for Scheme 2b include: a) p-anisaldehyde, NaOH, H₂O, RT, 1 h (80%); b) Ac₂O, pyridine, RT, overnight (81%); c) 5 M HCl, acetone, reflux, 30 min (86%); d) chloroacetic anhydride, pyridine, DCM, 0° C.-RT (89%); e) 1,4-benzenedithiol, TEA, DCM, 16 h (91%); f) Et₃PAuCl, DBU, DCM, RT, 1.5 h (96%).

1,2,3,4-Tetra-O-acetyl-2-chloroacetamido-2-deoxy-β-D-glucopyranose (8e). To a solution of 8d (2.53 g, 6.51 mmol) in 30 mL of DCM, pyridine (0.84 mL, 10.4 mmol) was added. The solution was brought to 0° C. Chloroacetic anhydride (1.67 g, 9.77 mmol) was added. The reaction solution was stirred overnight, then was poured into 50 mL of a 1 M HCl solution and was extracted by DCM (50 mL×3). The combined organic phase was washed by saturated NaHCO₃, brine, and dried over MgSO₄. After removing the solvent, the residue was purified by flash column chromatography (ethyl acetate:hexanes=2:3) to afford 8e as a white solid (2.45 g, 89%). $^1$H NMR (500 MHz, CDCl₃) δ 6.59 (d, J=9.2 Hz, 1H, NH), 5.81 (d, J=8.6 Hz, 1H, H-1), 5.28 (dd, J=10.5, 9.3 Hz, 1H, H-3), 5.14 (t, J=9.5 Hz, 1H, H-4), 4.29 (dd, J=12.5, 4.7 Hz, 1H, H-6a), 4.22 (dt, J=10.5, 9.0 Hz, 1H, H-2), 4.14 (dd, J=12.5, 2.3 Hz, 1H, H-6b), 3.98 (d, J=1.6 Hz, 2H, CH₂Cl), 3.85 (ddd, J=9.8, 4.6, 2.3 Hz, 1H, H-5), 2.12 (s, 3H, OAc), 2.10 (s, 3H, OAc), 2.05 (s, 3H, OAc), 2.05 (s, 3H, OAc).

1,3,4,6-Tetra-O-acetyl-2-((4-mercaptophenyl)sulfanyl) acetamido-2-deoxy-β-D-glucopyranose (8f). To a solution of compound 8e (160 mg, 0.378 mmol) and 1,4-benzenedithiol (107 mg, 0.755 mmol) in 5 mL of DCM, TEA (42 mg, 0.415 mmol) was added. The reaction was stirred for 16 h. Then it was concentrated and directly purified by flash column chromatography (ethyl acetate:DCM=1:1.2) to give the product as a colorless viscous solid (180 mg, 90%). $^1$H NMR (500 MHz, CDCl₃) δ 7.22-7.17 (m, 2H, Ar—H), 7.15-7.09 (m, 2H, Ar—H), 6.81 (d, J=9.2 Hz, 1H, NH), 5.73 (d, J=8.7 Hz, 1H, H-1), 5.24 (dd, J=10.5, 9.3 Hz, 1H, H-3), 5.09 (t, J=9.6 Hz, 1H, H-4), 4.27 (dd, J=12.5, 4.6 Hz, 1H, H-6a), 4.18 (dt, J=10.5, 9.1 Hz, 1H, H-2), 4.11 (dd, J=12.5, 2.2 Hz, 1H, H-6b), 3.82 (ddd, J=9.9, 4.6, 2.3 Hz, 11, H-5), 3.53 (q, J=16.6 Hz, 2H, SCH₂), 3.45 (s, 1H, SH), 2.08 (s, 3H, OAc), 2.02 (s, 3H, OAc), 1.95 (s, 3H, OAc), 1.88 (s, 3H, OAc). $^{13}$C NMR (126 MHz, CDCl₃) δ 170.80, 170.74, 169.43, 169.30, 168.43, 131.72, 130.33, 130.06, 129.04, 92.28, 72.94, 72.18, 68.10, 61.76, 53.47, 37.60, 20.83, 20.81, 20.69, 20.57.

[1,3,4,6-Tetra-O-acetyl-2-((4-sulfanylbenzenethiolatoxtriethylphosphine)gold(I)] acetamido-2-deoxy-β-D-glucopyranose (8). To a solution of compound 8f (110 mg, 0.208 mmol) and Et₃PAuCl (73 mg, 0.208 mmol) in DCM (6 mL), DBU (48 mg, 0312 mmol) was added. The reaction mixture was stirred for 1.5 h. After concentrating by rotovap, the crude was purified by flash column chromatography (ethyl acetate:DCM=1:1~2:1) to give the product as a colorless viscous solid (169 mg, 96%). H NMR (500 MHz, CDCl$_3$) δ 7.46-7.39 (m, 6H, Ar—H), 7.04 (d, J=9.3 Hz, 1H, NH), 7.01-6.97 (m, 6H. Ar—H), 5.77 (d, J=8.8 Hz, 1H, H-1), 5.31 (dd, J=10.6, 9.3 Hz, 1H, H-3), 5.09 (t, J=9.6 Hz, 1H, H-4), 4.27 (dd, J=12.5, 4.6 Hz, 1H. H-6a), 4.20 (dt, J=10.5, 9.1 Hz, 1H, H-2), 4.11 (dd, J=12.4, 2.2 Hz, 1H, H-6b), 3.85 (ddd, J=10.0, 4.5, 2.3 Hz, 1H, H-5), 3.49 (q, J=16.5 Hz, 2H, SCH$_2$), 2.08 (s, 3H, OAc), 2.02 (s, 3H, OAc), 1.97 (s, 3H, OAc), 1.91 (s, 3H, OAc), 1.87 (dq, J=9.9, 7.6 Hz, 6H, P(CH$_2$CH$_3$)$_3$), 1.22 (dt, J=18.6, 7.6 Hz, 9H, P(CH$_2$CH$_3$)$_3$). $^{13}$C NMR (126 MHz, CDCl$_3$) δ 170.75, 170.67, 169.43, 169.30, 168.97, 142.54, 133.31 (2C), 128.86 (2C) 127.92, 92.13, 72.72, 72.10, 68.24, 61.77, 53.20, 38.54, 20.83, 20.72, 20.60, 20.57, 18.14 (d, J=33.9 Hz, 3C, P(CH$_2$CH$_3$)$_3$)), 9.08 (s, P(CH$_2$CH$_3$)$_3$). Purity by quantitative proton NMR ($^1$H qNMR): 95%.

Example 3

The synthetic scheme for Compounds 9-17 is shown in Scheme 3a.

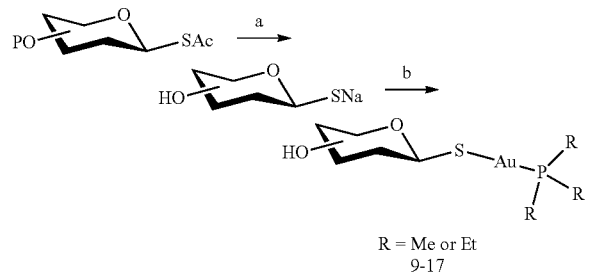

Scheme 3a

R = Me or Et
9-17

Reagents and conditions used in Scheme 3a include: a) NaOMe, MeOH, RT, 2-4 h; b) Et$_3$PAuCl or Me$_3$PAuCl, MeOH, 1-2 h.

(1-Thio-β-D-glucopyranosato)(triethylphosphine) gold(I) (9). This compound was prepared from compound 1b (200 mg, 0.492 mmol) according to general procedure E and was purified by silica gel chromatography (DCM:methanol=10:1-6:1) to give compound 9 (208 mg, 83%) as a colorless viscous solid. $^1$H NMR (500 MHz, D$_2$O) δ 4.87 (d, J=9.1 Hz, 1H, H-1), 3.81 (dd, J=12.3, 2.1 Hz, 1H, H-6a), 3.60 (dd, J=12.3, 6.0 Hz, 1H, H-6b), 3.47-3.28 (m, 3H), 3.20 (t, J=9.1 Hz, 1H), 1.89 (dq, J=9.8, 7.7 Hz, 6H, P(CH$_2$CH$_3$)$_3$),), 1.14 (dt, J=18.5, 7.6 Hz, 9H, P(CH$_2$CH$_3$)$_3$). Purity: 98% by $^1$H qNMR.

(1-Thio-β-D-galatopyranosato)(triethylphosphine) gold (I) (10). This compound was prepared from compound 1b (307 mg, 0.755 mmol) according to general procedure E, and was purified by silica gel chromatography (DCM:methanol=10:1~6:1) to give compound 10 as a colorless viscous solid (284 mg, 74%). $^1$H NMR (500 MHz, D$_2$O) δ 4.90 (d, J=9.0 Hz, 1H, H-1), 3.98 (d, J=3.3 Hz, 1H, H-4), 3.80-3.66 (m, 3H, H-3-, H-5, H-6a), 3.62 (dd, J=9.6, 3.4 Hz, 1H, H-6b), 3.54 (t, J=9.3 Hz, 1H, H-2), 1.97 (dq, J=9.8, 7.6 Hz, 6H, P(CH$_2$CH$_3$)$_3$),), 1.23 (dt, J=18.7, 7.6 Hz, 9H, P(CH$_2$CH$_3$)$_3$). $^{13}$C NMR (50 MHz, D$_2$O) δ 85.39, 79.42, 76.96, 74.03, 69.54, 61.53, 17.78 (d, J=33.9 Hz, P(CH$_2$CH$_3$)$_3$)), 8.98 (s, P(CH$_2$CH$_3$)$_3$). $^{31}$P NMR (81 MHz, D$_2$O) δ 37.75. Purity: 96% by $^1$H qNMR.

(1-Thio-D-mannopyranosatoxtriethylphosphine) gold(I) (11). This compound was prepared from 2,3,4,6-tetra-O-acetyl-1-S-acetyl-α-D-mannopyranose (283 mg, 0.696 mmol) following general procedure E and was purified by silica gel chromatography with gradient elution (DCM:methanol=10:1 to 6:1) to give compound 11 as a colorless viscous solid (277 mg, 78%). $^1$H NMR (400 MHz, D$_2$O, α/β=7.4:1) δ 5.73 (d, J=1.2 Hz, 1H, H-1α), 4.72 (d, J=1.5 Hz, 1H, H-1β), 4.31 (dd, J=9.6, 3.3 Hz, 1H, H-3α), 4.17 (ddd, J=9.8, 4.8, 2.7 Hz, 1H, H-5α), 3.99 (dd, J=3.2, 1.6 Hz, 1H, H-2a), 3.89 (td, J=3.6, 1.8 Hz, 1H, H-5β), 3.82-3.71 (m, 2H, H-6aα, H-6bα), 3.64 (t, J=9.8 Hz, 1H, H-4), 1.92 (dq, J=9.8, 7.6 Hz, 6H), 1.16 (dt, J=18.4, 7.6 Hz, 9H). $^{13}$C NMR (101 MHz, D$_2$O, α-anomer) δ 82.77, 76.37, 72.58, 70.16, 67.30, 60.91, 17.30 (d, J=33.9 Hz, P(CH$_2$CH$_3$)$_3$)), 8.49 (s, P(CH$_2$CH$_3$)$_3$). $^{31}$P NMR (162 MHz, D$_2$O) δ 37.72. Purity: 97% by $^1$H qNMR.

(2-Acetamido-2-deoxy-1-thio-β-D-glucopyranosato)(triethylphosphine) gold(I) (12). This compound was prepared from compound 3b (310 mg, 0.765 mmol) according to general procedure E and was purified by silica gel chromatography (DCM:methanol=5:1) to give compound 12 as a colorless viscous solid (295 mg, 70%). $^1$H NMR (500 MHz, D$_2$O) 5.10 (d, J=9.7 Hz, 1H), 3.90 (dd, J=12.3, 1.8 Hz, 1H), 3.77 (t, J=9.5 Hz, 1H), 3.71 (dd, J=12.3, 5.4 Hz, 1H), 3.54-3.40 (m, 2H), 2.08 (s, 3H), 1.98 (dq, J=15.6, 7.6 Hz, 10H), 1.23 (dt, J=18.6, 7.6 Hz, 16H). $^{13}$C NMR (50 MHz, D$_2$O) δ 173.92, 83.48, 80.51, 76.16, 70.72, 62.18, 61.75, 23.04, 17.75 (d, J=33.9 Hz, P(CH$_2$CH$_3$)$_3$)), 9.07 (s, P(CH$_2$(H$_3$)$_3$). $^{31}$P NMR (81 MHz, D$_2$O) 37.93. Purity: 97% by $^1$H qNMR.

[β-D-galactopyranosyl-(1→4)-β-D-glucopyranosato](triethylphosphine) gold(I) (13). Compound 13 was prepared from compound 6b (402 mg, 0.579 mmol) according to general procedure E and was purified by silica gel chromatography (DCM:methanol=5:1-3:1) to give compound 13 as a colorless viscous solid (243 mg, 62%). $^1$H NMR (500 MHz, D$_2$O) δ 5.00 (d, J=9.2 Hz, 1H), 4.47 (d, J=7.8 Hz, 1H), 4.02-3.92 (m, 2H), 3.78 (m, 4H), 3.70 (dd, J=10.0, 3.3 Hz, $^1$H), 3.67-3.54 (m, 4H), 3.36 (t, J=8.8 Hz, 1H), 1.98 (dq, J=9.7, 7.8 Hz, 6H, P(CH$_2$CH$_3$)$_3$),), 1.24 (dt, J=18.8, 7.6 Hz, 9H, P(CH$_2$CH$_3$)$_3$). $^{13}$C NMR (50 MHz, D$_2$O) δ 103.36, 84.90, 79.71, 79.42, 79.24, 75.84, 75.78, 73.00, 71.41, 69.02, 61.47, 61.07, 17.82 (d, J=34.5 Hz, P((CH$_2$CH$_3$)$_3$)), 9.06 (s, P(CH$_2$CH$_3$)$_3$). $^{31}$P NMR (81 MHz, D$_2$O) δ 39.39. Purity: 95% by H qNMR.

(1-Thio-β-D-maltosato)(triethylphosphine) gold(I) (14). Compound 14 was prepared from compound 5b (407 mg, 0.586 mmol) according to general procedure E and was purified by silica gel chromatography (DCM:methanol=5:1-3:1) to give compound 14 as a colorless viscous solid (252 mg, 64%). $^1$H NMR (500 MHz, D$_2$O) δ 5.41 (d, J=3.8 Hz, 1H), 4.98 (d, J=9.2 Hz, 1H), 3.98-3.85 (m, 2H), 3.82-3.66 (m, 5H), 3.65-3.56 (m, 3H), 3.44 (t, J=9.5 Hz, 1H), 3.34 (t, J=9.2 Hz, 1H), 1.99 (dq, J=15.8, 7.7 Hz, 6H), 1.24 (dt, J=18.7, 7.6 Hz, 9H). $^{13}$C NMR (50 MHz, D$_2$O) 100.06, 84.94, 80.00, 79.05, 77.92, 77.63, 73.34, 73.14, 72.18, 69.82, 61.75, 60.99, 17.85 (d, J=34.0 Hz, P(CH$_2$CH$_3$)$_3$)), 9.08 (s, P(CH$_2$CH$_3$)$_3$). $^{31}$P NMR (81 MHz, D$_2$O) δ 38.39. Purity: 96% by $^1$H qNMR.

(1-Thio-β-D-glucopyranosato)(trimethylphosphine) gold (I) (15). This compound was prepared from compound 1b (120 mg, 0.295 mmol) according to general procedure E, and was purified by silica gel chromatography (DCM:methanol=10:1-5:1) to give the product as a colorless viscous solid (70 mg, 57%). $^1$H NMR (500 MHz, D$_2$O) δ 4.94 (d, J=9.1 Hz, 1H), 3.93 (dd, J=12.3, 1.7 Hz, 1H), 3.73 (dd, J=12.3, 5.9 Hz, 1H), 3.53-3.42 (m, 3H), 3.28 (t, J=8.9 Hz, 1H), 1.69 (d, J=10.9 Hz, 9H). $^{13}$C NMR (126 MHz, D$_2$O) δ 84.54, 80.07, 79.30, 76.90, 70.08, 61.22, 15.11 (d, J=37.7 Hz, PMe$_3$). $^{31}$P NMR (162 MHz, D$_2$O) δ−1.06. Purity: 95% by $^1$H qNMR.

(1-Thio-β-D-galatopyranosato)(trimethylphosphine) gold (I) (16). This compound was prepared from compound 2b (120 mg, 0.295 mmol) according to general procedure E, and was purified by silica gel chromatography (DCM: methanol=10:1-5:1) to give compound 16 as a colorless viscous solid (72 mg, 59%). $^1$H NMR (500 MHz, D$_2$O) δ 4.91 (d, J=9.1 Hz, 1H), 4.01 (d, J=3.4 Hz, 1H), 3.83-3.70 (m, 3H), 3.65 (dd, J=9.6, 3.4 Hz, 1H), 3.53 (t, J=9.3 Hz, 1H), 1.69 (d, J=10.0 Hz, 9H). $^{13}$C NMR (126 MHz, D$_2$O) δ 85.15, 79.12, 76.53, 73.69, 69.16, 61.17, 15.10 (d, J=38.3 Hz, PMe$_3$). $^{31}$P NMR (162 MHz, D$_2$O) δ−0.87. Purity: 96% by $^1$H qNMR.

(2-Acetamido-2-deoxy-1-thio-β-D-glucopyranosato) (trimethylphosphine) gold(I) (17). This compound was prepared from compound 3b (150 mg, 0.370 mmol) according to general procedure E, and was purified by silica gel chromatography (DCM:methanol=10:1-5:1) to give compound 17 as a colorless viscous solid (126 mg, 67%). $^1$H NMR (500 MHz, D$_2$O) δ 5.09 (d, J=8.6 Hz, 1H), 3.92 (d, J=12.1 Hz, 1H), 3.86-3.66 (m, 2H), 3.60-3.35 (m, 3H), 2.10 (s, 3H), 1.67 (d, J=11.1 Hz, 9H, PMe$_3$). $^{13}$C NMR (101 MHz, D$_2$O) δ 173.62, 83.19, 80.24, 75.69, 70.09, 61.44, 61.14, 22.69, 15.06 (d, J=37.7 Hz, PMe$_3$). $^{31}$P NMR (162 MHz, D$_2$O) δ−1.98. Purity: 95% by $^1$H qNMR.

The synthesis for compounds 18-26 is shown in Scheme 3b.

Scheme 3b

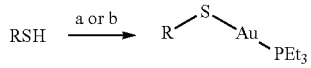

Reagents and conditions for Scheme 3b: a) For compounds 18-19, 21-23: Et$_3$PAuCl, DBU, DCM, RT, 1-2 h (62%-91%). b) for compounds 20, 24-26: Et$_3$PAuCl, NaOMe, MeOH, RT, 1-2 h (59%-92%).

(Benzenethiolato)(triethylphosphine) gold(I) (18) (Scheme 3b, condition a). Compound 18 was prepared from thiophenol (35 mg, 0.314 mmol) according to general procedure E, and was purified by flash column chromatography (ethyl acetate:hexanes=2:3) to afford the product as a pale yellow oil (104 mg, 78%). $^1$H NMR (500 MHz, CDCl$_3$)) δ 7.53 (d, J=7.8 Hz, 2H), 7.07 (t, J=7.7 Hz, 2H), 6.96 (t, J=7.3 Hz, 1H), 1.83 (dq, J=10.1, 7.7 Hz, 6H), 1.20 (dt, J=18.5, 7.6 Hz, 9H). $^{13}$C NMR (126 MHz, CDCl$_3$) δ 141.92, 132.44, 127.94, 123.27, 18.10 (d, J=33.1 Hz, P(CH$_2$CH$_3$)$_3$)), 9.07 (s, P(CH$_2$CH$_3$)$_3$). $^{31}$P NMR (81 MHz, CDCl$_3$) δ 36.42. Purity: 96% by $^1$H qNMR.

(2-Aminobenzenethiolato)(triethylphosphine) gold(I) (19) (Scheme 3b, condition a). Compound 19 was prepared from 2-aminobenzenethiol (36 mg, 0.285 mmol) according to general procedure D using DCM as the solvent, and the crude was purified by flash column chromatography (ethyl acetate:hexanes=1:2) to afford the product as a light orange solid (78 mg, 62%). $^1$H NMR (500 MHz, CDCl$_3$) δ 7.51 (dd, J=7.7, 1.5 Hz, 1H, Ar—H), 6.86 (td, J=7.7, 1.5 Hz, 1H, Ar—H), 6.66 (dd, J=7.8, 1.4 Hz, 1H, Ar—H), 6.55 (td, J=7.5, 1.4 Hz, 1H, Ar—H), 4.09 (bs, 2H, NH$_2$), 1.80 (dq, J=9.9, 7.6 Hz, 6H, P(CH$_2$CH$_3$)), 1.17 (dt, J=18.4, 7.6 Hz, 9H, P(CH$_2$CH$_3$)$_3$). $^{13}$C NMR (126 MHz, CDCl$_3$) δ 147.03, 135.32, 125.31, 124.15, 117.61, 114.23, 18.13 (d, J=33.1 Hz, P(CH$_2$CH)$_3$)), 9.04 (s, P(CH$_2$CH$_3$)$_3$). $^{31}$P NMR (81 MHz, CDCl$_3$) δ 38.20. Purity: 98% by $^1$H qNMR.

(4-Aminobenzenethiolato)(triethylphosphine) gold(I) (20) (Scheme 3b, condition b). To a solution of 4-aminothiophenol (45 mg, 0.359 mmol) and NaOMe (100 μL, 25 wt % in MeOH) in cold MeOH (4 mL), gold triethylphosphine chloride (120 mg, 0.342 mmol) in DCM/MeOH (v/v 1:1) was added dropwise. The reaction was stirred for 1 h. The solvent was removed by rotovap, and water was added to the mixture. The mixture was extracted by DCM twice. The combined organic phase was washed with brine and dried over Na$_2$SO$_4$. The solution was concentrated, then toluene (1 mL) was added. The remaining DCM was removed by rotovap, after which hexanes (3 mL) was added. The solution was kept at −20° C., after which yellow crystals formed. The supernatant was removed with a pipet, and the crystals were washed with hexanes and dried under vacuum to afford the product as yellow crystals (138 mg, 92%). $^1$H NMR (500 MHz, CDCl$_3$) δ 7.31-7.23 (m, 2H, Ar—H), 6.53-6.44 (m, 2H, Ar—H), 3.49 (s, 2H, NH$_2$), 1.81 (dq, J=9.8, 7.6 Hz, 6H, P(CH$_2$CH$_3$)$_3$), 1.18 (dt, J=18.4, 7.6 Hz, 9H, P(CH$_2$CH$_3$)$_3$). $^{13}$C NMR (126 MHz, CDCl$_3$) 5142.80, 133.37, 128.36, 115.47, 18.03 (d, J=32.9 Hz, P(CH$_2$CH$_3$)$_3$)), 8.99 (s, P(CH$_2$CH$_3$)$_3$). $^{31}$P NMR (81 MHz, CDCl$_3$) δ 37.40. Purity: 98% by $^1$H qNMR.

(4-Methoxybenzenethiolato)(triethylphosphine) gold(I) (21) (Scheme 3b, condition a). This compound was prepared from 4-methoxybenzenethiol (48 mg, 0.342 mmol) according to general procedure D using DCM as the solvent, and the crude was purified by flash column chromatography (ethyl acetate:hexanes=1:2) to afford the product as a colorless viscous solid (104 mg, 78%). $^1$H NMR (500 MHz, CDCl$_3$) δ 7.44-7.38 (m, 2H, Ar—H), 6.71-6.64 (m, 2H, Ar—H), 3.73 (s, 3H, OMe), 1.83 (dq, J=9.8, 7.6 Hz, 6H, P(CH$_2$CH$_3$)$_3$), 1.20 (dt, J=18.4, 7.6 Hz, 9H, P(CH$_2$CH$_3$)$_3$). $^{13}$C NMR (126 MHz, CDCl$_3$) δ 156.74, 133.56, 131.72, 113.85, 55.38, 18.18 (d, J=33.0 Hz, P(CH$_2$CH$_3$)$_3$)), 9.09 (s, P(CH$_2$CH$_3$)$_3$). $^{31}$P NMR (81 MHz, CDCl$_3$) δ 38.79. Purity: 99% by $^1$H qNMR.

(4-Nitrobenzenethiolato)(triethylphosphine) gold(I)(22) (Scheme 3b, condition a). Compound 22 was prepared from 4-nitrobenzenethiol (56 mg, 0.359 mmol) according to general procedure D using DCM as the solvent, and the crude was purified by flash column chromatography with gradient elution (ethyl acetate:hexanes=1:4 to 1:2) to afford the product as a yellow solid (151 mg, 91%). $^1$H NMR (500 MHz, CDCl$_3$) δ 7.95-7.88 (m, 2H, Ar—H), 7.63-7.57 (m, 2H, Ar—H), 1.92 (dq, J=9.9, 7.6 Hz, 6H, P(CH$_2$CH$_3$)$_3$), 1.24 (dt, J=18.7, 7.6 Hz, 9H, P(CH$_2$CH$_3$)$_3$). $^{13}$C NMR (126 MHz, CDCl$_3$) δ 156.67, 143.86, 131.94, 122.99, 18.07 (d, J=33.5 Hz, P(CH$_2$CH$_3$)$_3$)), 9.12 (s, P(CH$_2$CH$_3$)$_3$). $^{31}$P NMR (81 MHz, CDCl$_3$) δ 37.77. Purity: 99% by $^1$H qNMR.

(4-(Trifluromethyl)benzenethiolato)(triethylphosphine) gold(I) (23) (Scheme 3b, condition a). Compound 23 was prepared from 4-(trifluoromethyl) benzenethiol (61 mg, 0.342 mmol) according to general procedure D using DCM as the solvent, and the crude was purified by flash column chromatography (ethyl acetate:hexanes=1:2) to give the product as a colorless viscous solid (126 mg, 75%). $^1$H NMR (500 MHz, CDCl$_3$) δ 7.63-7.58 (m, 2H, Ar—H), 7.31-7.26 (d, J=8.1 Hz, 2H, Ar—H), 1.87 (dq, J=9.9, 7.6 Hz, 6H, P(CH$_2$CH$_3$)$_3$), 1.22 (dt, J=18.6, 7.7 Hz, 9H, P(CH$_2$CH$_3$)$_3$)). $^{13}$C NMR (126 MHz, CDCl$_3$) δ 148.93, 132.22, 125.18 (q, $^2J_{CF}$=32.4 Hz), 124.88 (q, $^1J_{CF}$=270.72 Hz, CF$_3$), 124.63 (q, $^3J_{CF}$=3.6 Hz), 18.18 (d, $^1J_{CP}$=33.4 Hz, P(CH$_2$CH$_3$)$_3$)), 9.13

(s, P(CH$_2$CH$_3$)$_3$). $^{19}$F NMR (188 MHz, CDCl$_3$) δ–60.60. $^{31}$P NMR (81 MHz, CDCl$_3$) 39.08. Purity: 101% by $^1$H qNMR.

(2-Mercaptoethanolato)(triethylphosphine) gold(I) (24) (Scheme 3b, condition b). To a solution of 2-sulfanylethanol (24 uL, 0.342 mmol) in methanol (4 mL), NaOMe (20 mg, 25 wt % in methanol) was added. The solution was cooled to 0° C. A solution of Et$_3$PAuCl (120 mg, 0.342 mmol) in methanol (2 mL) was added dropwise, and the reaction mixture was stirred for 1 h. The solution was concentrated, and water was added, and the mixture was extracted by DCM twice. The combined organic phase was washed with brine, dried over Na$_2$SO$_4$ to give the product as a pale-yellow oil (134 mg, quant). $^1$H NMR (500 MHz, CD$_3$OD) δ 3.68-3.59 (m, 2H, CH$_2$OH), 2.98 (t, J=7.5 Hz, 2H, CH$_2$S), 1.94 (dq, J=10.2, 7.6 Hz, 6H, P(CH$_2$CH$_3$)$_3$), 1.23 (dt, J=18.4, 7.6 Hz, 9H, P(CH$_2$CH$_3$)$_3$). $^{13}$C NMR (126 MHz, CD$_3$OD) δ 68.04, 31.24, 18.95 (d, $^1J_{CP}$=33.4 Hz, P(CH$_2$CH$_3$)$_3$)), 9.50 (s, P(CH$_2$(H$_3$)$_3$). $^{31}$P NMR (81 MHz, CD$_3$OD) δ 38.71. Purity: 98% by $^1$H qNMR.

(Methyl mercaptoacetatato) (triethylphosphine) gold(I) (25) (Scheme 3b, condition b). Compound 25 was prepared from methyl thioglycolate (38 mg, 0.359 mmol) according to general procedure E. After the reaction was completed, the mixture was concentrated. Water was added, and the mixture was extracted with DCM twice. The combined organic phase was washed with brine and dried over Na$_2$SO$_4$. The residue was purified by flash column chromatography (ethyl acetate:hexanes=2:3) to afford the product as a colorless oil (85 mg, 59%). $^1$H NMR (500 MHz, CDCl$_3$) δ 3.70 (s, 3H, OMe), 3.56 (s, 2H, MeOCOCH$_2$), 1.84 (dq, J=9.8, 7.7 Hz, 6H, P(CH$_2$CH$_3$)$_3$), 1.22 (dt, J=18.4, 7.7 Hz, 9H, P(CH$_2$CH$_3$)$_3$). $^{13}$C NMR (126 MHz, CDCl$_3$) δ 175.69, 52.16, 29.15, 18.16 (d, $^1J_{CP}$=32.8 Hz, P(CH$_2$CH$_3$)$_3$)), 9.03 (s, P(CH$_2$CH$_3$)$_3$). $^{31}$P NMR (81 MHz, CDCl$_3$) δ 37.57. Purity: 99% by $^1$H qNMR.

(2,2,2-Trifluoroethanethiolato)(triethylphosphine) gold(I) (26) (Scheme 3b, condition b). Compound 26 was prepared from (triethylphosphine)gold chloride (120 mg, 0.342 mmol) and 2,2,2-trifluoroethanethiol (44 mg, 0.377 mmol) according to general procedure C. The product was obtained as a colorless oil (135 mg, 92%) with satisfied purity without column chromatography purification. $^1$H NMR (500 MHz, CDCl$_3$) δ 3.43 (q, J=10.1 Hz, 2H, CF$_3$CH$_2$), 1.85 (dq, J=9.8, 7.6 Hz, 6H, P(CH$_2$CH$_3$)$_3$), 1.21 (dt, J=18.4, 7.6 Hz, 9H, P(CH$_2$CH$_3$)$_3$). $^{13}$C NMR (126 MHz, CDCl$_3$) δ 127.32 (d, J=274.7 Hz, CF$_3$), 30.33 (q, J=32.2 Hz, CF$_3$CH$_2$), 18.13 (d, $^1J_{CP}$=33.2 Hz, P(CH$_2$CH$_3$)$_3$)), 9.00 (s, P(CH$_2$CH$_3$)$_3$). $^{19}$F NMR (188 MHz, CDCl$_3$) δ–65.55 (t, J=10.0 Hz). $^{31}$P NMR (81 MHz, CDCl$_3$) δ 38.87. Purity: 102% by $^1$H qNMR.

(2-Mercaptoethanolato)(trimethylphosphine) gold (I) (27). To a solution of 2-sulfanylethanol (40 mg, 0.512 mmol) and Me$_3$PAuCl (0.538 mmol, 166 mg) in MeOH, NaOMe (121 mg, 25 wt %, 0.563 mmol) was added. After stirring at RT for 1.5 h, the solvent was removed. DCM (5 mL) and water (5 mL) were added, and the mixture was extracted by DCM twice. The combined organic phase was dried over Na$_2$SO$_4$ and filtered. After removal of the solvent, the desired product was obtained as a white solid (179 mg, 88%). $^1$H NMR (500 MHz, CDCl$_3$) δ 3.73-3.62 (m, 2H, HOCH$_2$CH$_2$), 3.18-3.07 (m, 3H, HOCH-2CH$_2$ and OH), 1.60 (d, J=10.5 Hz, 9H, PMe$_3$). $^{13}$C NMR (126 MHz, CDCl$_3$) δ 65.98, 32.24, 16.03 (d, $^1J_{CP}$=35.7 Hz, PMe$_3$). $^{31}$P NMR (162 MHz, CDCl$_3$) δ–0.13. Purity: 100% by $^1$H qNMR.

Example 4A

The synthetic scheme for compounds 28-34, 1, and 35-40 is shown in Scheme 4a.

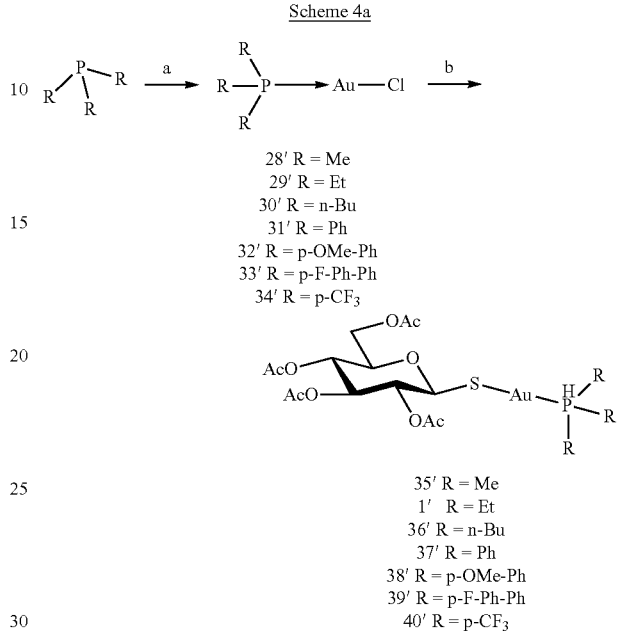

Scheme 4a

28' R = Me
29' R = Et
30' R = n-Bu
31' R = Ph
32' R = p-OMe-Ph
33' R = p-F-Ph-Ph
34' R = p-CF$_3$

35' R = Me
1' R = Et
36' R = n-Bu
37' R = Ph
38' R = p-OMe-Ph
39' R = p-F-Ph-Ph
40' R = p-CF$_3$

Reagents and conditions used in the Scheme 4a include: HAuCl$_4$ 3H$_3$O, 2,2'-thiodiethanol, H$_2$O/EtOH; b) Et$_3$PAuCl, K$_2$CO$_3$, DCM/H$_2$O, 0° C. to RT, 1 to 2 h.

(Trimethylphosphine) gold chloride (28). Compound 28 was prepared from gold acid chloride trihydrate (1.05 g, 2.62 mmol) and PMe$_3$ (2.86 mL, 1M in THF) according to general procedure F. The product was obtained as a white amorphous solid (580 mg, 72%). $^1$H NMR (500 MHz, CDCl$_3$) δ 1.63 (d, J=11.3 Hz, 9H). $^{13}$C NMR (126 MHz, CDCl$_3$) δ 16.25 (d, $^1J_{CP}$=40.3 Hz). $^{31}$P NMR (81 MHz, CDCl$_3$) δ–9.94.

(Triethylphosphine) gold chloride (29). Compound 29 was prepared from gold acid chloride trihydrate (1.57 g, 4.0 mmol) and PEt$_3$ (0.5 g, 4.25 mmol) according to general procedure F. The product was obtained as a white amorphous solid (1.41 g, quant). $^1$H NMR (500 MHz, CDCl$_3$) δ 1.87 (dq, J=10.3, 7.6 Hz, 6H), 1.21 (dt, J=19.0, 7.7 Hz, 9H). $^1$P NMR (81 MHz, CDCl$_3$) δ 33.15. Purity: 97% by $^1$H qNMR.

(Tri-n-butylphosphine) gold chloride (30). Compound 30 was prepared from gold acid chloride trihydrate (525 mg, 1.31 mmol) and tri-n-butylphosphine (287 mg, 1.40 mmol) according to general procedure F with a slightly modification. After extraction, the solvent was removed, and the residue was purified by column chromatography (ethyl acetate:hexanes=1:3) to afford the product as a colorless oil (530 mg, 93%). $^1$H NMR (500 MHz, CDCl$_3$) δ 1.85-1.74 (m, 2H), 1.63-1.50 (m, 2H), 1.46 (q, J=7.3 Hz, 2H), 0.95 (t, J=7.3 Hz, 3H). $^{13}$C NMR (126 MHz, CDCl$_3$) δ 27.45, 25.77 (d, $^1J_{CP}$=36.1 Hz), 24.19 (d, $^2J_{CP}$=15.0 Hz), 13.75. $^{31}$P NMR (81 MHz, CDCl$_3$) δ 22.38. Purity: 100% by $^1$H qNMR.

(Triphenylphosphine) gold chloride (31). This compound was prepared from gold acid chloride trihydrate (0.785 g, 2.0 mmol) and PPh$_3$ (556 mg, 2.12 mmol) according to general procedure F. The product was obtained as a white amorphous solid (960 mg, 97%). $^1$H NMR (500 MHz, CDCl$_3$) δ 7.57-7.50 (m, 9H, Ar—H), 7.43-7.49 (m, 6H, Ar—H). $^{13}$C NMR (126 MHz, CDCl$_3$) δ 134.30 (d, J=13.8 Hz), 132.00 (d, J=2.4 Hz), 129.35 (d, J=11.8 Hz), 129.21 (d, J=59.9 Hz). $^{31}$P NMR (81 MHz, CDCl$_3$) δ 33.35. Purity: 99% by $^1$H qNMR.

(Tris(4-methoxyphenyl)phosphine) gold chloride (32). Compound 32 was prepared from gold acid chloride trihydrate (525 mg, 1.31 mmol) and tris (4-methoxyphenyl) phosphine (500 mg, 1.35 mmol) according to general procedure F with a slight modification. The precipitate was washed by EtOH instead of an EtOH/H$_2$O solution. The product was obtained as a white amorphous solid (716 mg, 94%). $^1$H NMR (500 MHz, CDCl$_3$) δ 7.57-7.35 (m, 6H, Ar—H), 7.04-6.86 (m, 6H, Ar—H), 3.84 (s, 9H, OMe). $^{13}$C NMR (126 MHz, CDCl$_3$) δ 162.49 (d, J=2.5 Hz), 135.71 (d, J=15.3 Hz), 120.55 (d, J=68.2 Hz), 114.88 (d, J=13.0 Hz), 55.60. $^{31}$P NMR (81 MHz, CDCl$_3$) δ 29.49.

(Tris(4-fluorphenyl)phosphine) gold chloride (33). Compound 33 was prepared from gold acid chloride trihydrate (525 mg, 1.31 mmol) and tris (4-flurophenyl) phosphine (443 mg, 1.37 mmol) according to general procedure F with a slight modification. The precipitate was washed by EtOH instead of EtOH/H$_2$O solution. The product was obtained as a white amorphous solid (672 mg, 94%). $^1$H NMR (500 MHz, CDCl$_3$) δ 7.63-7.48 (m, 6H, Ar—H), 7.21 (td, J=8.5, 1.8 Hz, 6H, Ar—H). $^{13}$C NMR (126 MHz, CDCl$_3$) δ 165.18 (dd, J=255.7, 2.6 Hz), 136.34 (dd, J=15.8, 8.9 Hz), 124.29 (dd, J=65.2, 3.3 Hz), 117.04 (dd, J=21.7, 13.3 Hz). $^{19}$F NMR (188 MHz, CDCl$_3$) δ− 102.96 (m). $^{31}$P NMR (81 MHz, CDCl$_3$) δ 30.14 (s). Purity: 97% by $^1$H qNMR.

(Tris(4-trifluoromethylphenyl)phosphine) gold chloride (34). Compound 34 was prepared from gold acid chloride trihydrate (525 mg, 1.31 mmol) and tris(4-trifluoromethylphenyl) phosphine (647 mg, 1.37 mmol) according to general procedure F with a slight modification. The precipitate was washed by EtOH instead of EtOH/H$_2$O solution. The product was obtained as a white amorphous solid (857 mg, 94%). $^1$H NMR (500 MHz, CDCl$_3$) δ 7.79 (dd, J=8.5, 2.1 Hz, 6H), 7.69 (dd, J=12.8, 8.1 Hz, 6H). $^{13}$C NMR (126 MHz, CDCl$_3$) δ 134.71 (qd, J=33.4, 2.6 Hz), 134.69 (d, 1=14.7 Hz), 132.25 (d, J=57.7 Hz), 126.63 (dq, J=11.8, 3.6 Hz), 123.25 (q, J=273.1 Hz, CF$_3$). $^{19}$F NMR (188 MHz, CDCl$_3$) δ−60.82. $^{31}$P NMR (81 MHz, CDCl$_3$) δ 31.86. Purity: 101% by $^1$H qNMR.

(2,3,4,6-Tetra-O-acetyl-1-thio-β-D-glucopyranosato) (trimethylphosphine) gold(I) (35). Compound 35 was synthesized from trimethylphosphine gold chloride (85 mg, 0.274 mmol) and compound 1c (105 mg, 0.274 mmol) according to general procedure D using toluene as the solvent, and was purified by flash column chromatography (ethyl acetate:hexanes=5:1) to afford the product as a colorless viscous solid (145 mg, 83%). $^1$H NMR (500 MHz, CDCl$_3$) 5.19-5.08 (m, 3H), 4.98 (t, J=9.3 Hz, 1H), 4.25 (dd, J=12.2, 4.8 Hz, 1H), 4.12 (dd, J=12.1, 2.4 Hz, 1H), 3.74 (ddd, J=9.5, 4.7, 2.2 Hz, 1H), 2.08 (s, 3H), 2.07 (s, 3H), 2.02 (s, 3H), 1.99 (s, 3H), 1.61 (d, J=10.8 Hz, 9H). $^{13}$C NMR (126 MHz, CDCl$_3$) δ 170.76, 170.24, 169.72, 169.65, 83.21, 77.30, 75.76, 74.40, 68.87, 62.83, 21.26, 20.91, 20.72, 20.69, 15.96 (d, J=37.1 Hz). $^{31}$P NMR (81 MHz, CDCl$_3$) δ−3.47. Purity: 95% by $^1$H qNMR.

(2,3,4,6-Tetra-O-acetyl-1-thio-β-D-glucopyranosato)(tri-n-butylphosphine) gold(I) (36). Compound 36 was synthesized from tri-n-butylphosphine gold chloride (143 mg, 0.329 mmol) and compound 1c (126 mg, 0.345 mmol) according to general procedure D using toluene as the solvent, and was purified by flash column chromatography (ethyl acetate:hexanes=1:2) to afford the product as a colorless viscous solid (225 mg, 90%). $^1$H NMR (500 MHz, CDCl$_3$) δ 5.18-5.06 (m, 3H), 4.99 (t, J=9.0 Hz, 1H), 4.24 (dd, J=12.3, 4.9 Hz, 1H), 4.10 (dd, J=12.2, 2.3 Hz, 1H), 3.72 (ddd, J=8.6, 4.6, 2.0 Hz, 1H), 2.07 (s, 3H), 2.06 (s, 3H), 2.01 (s, 3H), 1.98 (s, 3H), 1.85-1.75 (m, 6H), 1.65-1.53 (m, 6H), 1.48 (h, J=7.2 Hz, 7H), 0.96 (t, J=7.2 Hz, 9H). $^{13}$C NMR (126 MHz, CDCl$_3$) δ 170.72, 170.25, 169.53, 169.51, 83.34, 77.53, 75.73, 74.31, 69.00, 62.94, 27.23, 25.58 (d, J=32.6 Hz), 24.16 (d, J=14.4 Hz), 21.15, 20.83, 20.67, 20.64, 13.68. $^{31}$P NMR (81 MHz, CDCl$_3$) δ 27.02. Purity: 96% by $^1$H qNMR.

(2,3,4,6-Tetra-O-acetyl-1-thio-β-D-glucopyranosato)(triphenylphosphine) gold(I) (37). Compound 37 was synthesized from triphenylphosphine gold chloride (258 mg, 0.521 mmol) and compound 1c (200 mg, 0.548 mmol) according to general procedure D using toluene as the solvent, and was purified by flash column chromatography (ethyl acetate:hexanes=2:3-1:1) to afford the product as a colorless viscous solid (377 mg, 88%). $^1$H NMR (500 MHz, CDCl$_3$) δ 7.62-7.44 (m, 15H, Ar—H), 5.23-5.01 (m, 4H), 4.22 (dd, J=12.2, 4.8 Hz, 1H), 4.12 (dd, J=12.2, 2.4 Hz, 1H), 3.76 (ddd, J=9.8, 4.8, 2.4 Hz, 1H), 2.05 (s, 3H), 2.02 (s, 3H), 1.98 (s, 3H), 1.89 (s, 3H). $^{13}$C NMR (126 MHz, CDCl$_3$) δ 170.88, 170.43, 169.70, 169.70, 134.36 (d, J=14.2 Hz), 131.71 (d, J=2.4 Hz), 129.84 (d, J=55.4 Hz), 129.28 (d, J=11.5 Hz), 83.20, 77.73, 75.82, 74.34, 69.08, 62.97, 21.23, 20.83, 20.83, 20.78. $^{31}$P NMR (81 MHz, CDCl$_3$) 36.93. Purity: 96% by $^1$H qNMR.

(2,3,4,6-Tetra-O-acetyl-1-thio-β-D-glucopyranosato)(tris (4-methoxyphenyl)phosphine) gold(I) (38). Compound 38 was synthesized from tris(4-methoxyphenyl)phosphine gold chloride (160 mg, 0.274 mol) and compound 1c (105 mg, 0.288 mmol) according to general procedure D using toluene as the solvent, and was purified by column chromatography (ethyl acetate:hexanes=1:1) to afford the product as a colorless viscous solid (224 mg, 89%). $^1$H NMR (500 MHz, CDCl$_3$) δ 7.51-7.44 (m, 6H, Ar—H), 7.01-6.95 (m, 6H, Ar—H), 5.20-5.10 (m, 3H, H-1, H-3, H-4), 5.06 (t, J=9.3 Hz, 1H, H-2), 4.22 (dd, J=12.2, 4.8 Hz, 1H, H-6a), 4.13 (dd, J=12.1, 2.5 Hz, 1H, H-6b), 3.84 (s, 9H, 3×OMe), 3.77 (ddd, J=9.7, 4.7, 2.5 Hz, 2H, H-5), 2.05 (s, 3H, OAc), 2.01 (s, 3H, OAc), 1.98 (s, 3H, OAc), 1.91 (s, 3H, OAc). $^{13}$C NMR (50 MHz, CDCl$_3$) δ 170.84, 170.34, 169.64, 169.58, 162.22, 135.70 (d, J=15.1 Hz), 121.27 (d, J=62.8 Hz), 114.79 (d, J=12.5 Hz), 83.19, 77.41, 75.70, 74.32, 69.09, 62.99, 55.49, 55.49, 55.49, 21.23, 20.79, 20.79, 20.79. $^{31}$P NMR (81 MHz, CDCl$_3$) δ 33.82. Purity: 96% by $^1$H qNMR.

(2,3,4,6-Tetra-O-acetyl-1-thio-β-D-glucopyranosato)(tris (4-fluorophenyl)phosphine)gold(I) (39). Compound 39 was synthesized from tris(4-fluorphenyl)phosphine gold chloride (144 mg, 0.262 mmol) and compound 1c (100 mg, 0.276 mmol) according to general procedure D using toluene as the solvent, and was purified by column chromatography (ethyl acetate:hexanes=1:2) to afford the product as a colorless viscous solid (198 mg, 86%). $^1$H NMR (500 MHz, CDCl$_3$) δ 7.64-7.50 (m, 6H, Ar—H), 7.25-7.18 (m, 6H, Ar—H), 5.16 (d, J=9.5 Hz, 1H, H-1), 5.15 (t, J=9.3 Hz, 1H, H-3), 5.08 (dd, J=9.9, 9.4 Hz, 1H, H-4), 5.03 (t, J=9.3 Hz, 1H, H-2), 4.24 (dd, J=12.2, 5.0 Hz, 1H, H-6a), 4.11 (dd, J=12.2, 2.4 Hz, 1H, H-6b), 3.79-3.74 (m, 1H, H-5), 2.07 (s, 3H, OAc), 2.02 (s, 3H, OAc), 1.98 (s, 3H, OAc), 1.94 (s, 3H, OAc). $^{13}$C NMR (126 MHz, CDCl$_3$) δ 170.69, 170.26, 169.77, 169.71, 163.99 (d, J=2.4 Hz), 136.43 (dd, J=16.0, 8.8 Hz), 125.37 (dd, J=57.3, 3.5 Hz), 116.92 (dd, J=21.6, 12.7 Hz), 83.31, 78.01, 75.83, 74.15, 69.02, 62.96, 21.19, 20.79, 20.73, 20.69. $^{19}$F NMR (188 MHz, CDCl$_3$) δ –103.75. $^{31}$P NMR (81 MHz, CDCl$_3$) δ 35.38. Purity: 94% by $^1$H qNMR.

(2,3,4,6-Tetra-O-acetyl-1-thio-β-D-glucopyranosato)(tris(4-(trifluoromethyl)phenylphosphine)) gold(I) (40). Compound 40 was synthesized from tris(4-trifluromethyl)phenylphosphine gold chloride (183 mg, 0.262 mmol) and compound 1c (100 mg, 0.275 mmol) according to general procedure D using toluene as the solvent, and was purified by column chromatography (ethyl acetate:hexanes=1:3) to afford the product as a colorless viscous solid (69 mg, 26%). $^1$H NMR (500 MHz, CDCl$_3$) δ 7.80 (d, J=6.6 Hz, 6H, Ar—H), 7.71 (dd, J=11.9, 8.1 Hz, 6H, Ar—H), 5.18 (d, J=9.4 Hz, 1H, H-1), 5.15 (t, J=9.3 Hz, 1H, H-3), 5.08 (t, J=9.8 Hz, 1H, H-4), 5.04 (t, J=9.3 Hz, 1H, H-2), 4.27 (dd, J=12.3, 5.1 Hz, 1H, H-6a), 4.11 (dd, J=12.3, 2.3 Hz, 1H, H-6b), 3.78 (ddd, J=9.9, 5.0, 2.4 Hz, 1H, H-5), 2.08 (s, 3H, OAc), 2.03 (s, 3H, OAc), 1.97 (s, 3H, OAc), 1.94 (s, 3H, OAc). $^{13}$C NMR (50 MHz, CDCl$_3$) δ 170.70, 170.29, 169.99, 169.75, 134.77 (d, 0.1=15.3 Hz), 134.52-132.25 (m), 126.49 (dq, J=11.0, 3.5 Hz), 123.42 (q, J=272.7 Hz, CF$_3$), 83.50, 78.27, 76.06, 74.16, 69.02, 62.99, 21.27, 20.83, 20.73, 20.73. $^{19}$F NMR (188 MHz, CDCl$_3$) δ –60.82. $^{31}$P NMR (81 MHz, CDCl$_3$) δ 32.62. Purity: 95% by $^1$H qNMR.

Example 4B

Scheme 4b-1 shows the synthetic pathway to Compounds 41-44.

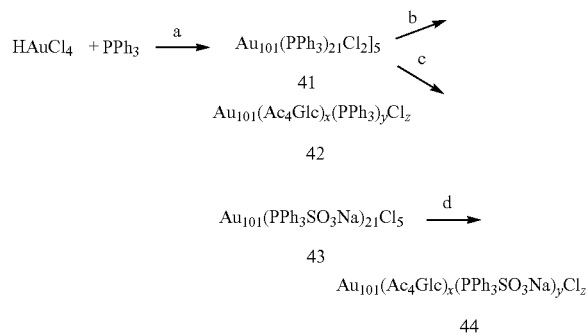

Reagents and conditions for Scheme 4b-1: a) NaBH$_4$, TOAB, Toluene/water, 3 h; b) Ac$_4$Glc, DCM, 12 h; c) TPPMS, DCM/water, 12 h; d) Ac$_4$Glc, DCM/water, 12 h.

Synthesis of 41. Argon was bubbled into a mixture of 65 mL/50 mL toluene/water for 1 hour. To this mixture, TOAB (1.2 g, 2.9 mmol) and HAuCl$_4$ (1.0 g, 2.5 mmol) were added, and the reaction was stirred vigorously until the gold color had transferred to the organic layer. Triphenylphosphine (2.3 g, 8.8 mmol) was added and the reaction was stirred for 10 minutes. NaBH$_4$ (1.0 g in 10 mL H$_2$O, 37 mmol) was added quickly, upon which the mixture turned black immediately. The reaction was maintained under Argon for 3 hours. The mixture was then washed with water (100 mL×2), evacuated and suspended in hexanes. The particles were then deposited onto a medium porosity frit and washed consecutively with hexanes (100 mL) followed by methanol/water (2:3)(100 mL), and hexanes (100 mL) followed by saturated NaNO$_2$ (100 mL) in a process that was repeated 5 times. The black product was dissolved in DCM and slowly precipitated with pentane (5 mL/h) three times to obtain the final product. $^1$H NMR (500 MHz, CDCl$_3$) δ 7.10 (broad). Au(PPh$_3$)Cl impurity $^1$H NMR (500 MHz, CDCl$_3$) 7.57-7.50 (m, 9H, Ar—H), 7.43-7.49 (m, 6H, Ar—H). $^{31}$P NMR (162 MHz, CDCl$_3$) δ 33.78.

Synthesis of 42, 43, and 44 was done by following the general procedure of ligand exchange.

Scheme 4b-2 shows the synthetic scheme for Compounds 45-47.

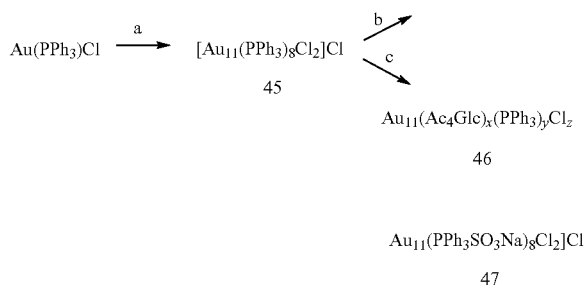

Reagents and conditions for Scheme 4b-2: a) NaBH$_4$, DCM, 24 h; b) Ac$_4$Glc, DCM, 12 h; c) TPPMS, DCM/water, 12 h; d) Ac$_4$Glc, DCM/water 12 h.

Synthesis of 45. Au(PPh$_3$)Cl (663 mg, 1.34 mmol) was dissolved in 28 mL of dry DCM. To this stirring solution, NaBH$_4$ (13.8 mg, 0.365 mmol) in 4.20 mL of absolute ethanol was quickly added. The stirring was continued for 24 h at room temperature, after which the solvents were evaporated. The dark red residual obtained was dissolved in a minimum amount of DCM and precipitated by slow addition (5 mL/h) of pentane until small red particles were observed at the bottom of the reaction flask. The clusters obtained were dissolved in DCM, purified by column chromatography using DCM/MeOH (15:1 v/v). TLC was used to confirm the absence of Au(PPh$_3$)Cl, (R$_f$~0.9 in DCM). The product was obtained as a red solid (0.2 g, 60% yield based on Au). $^1$H NMR (500 MHz, CDCl$_3$) δ 7.32 (b, 2H, Ar—H), 6.94 (dd, 1H, Ar—H), 6.68 (dd, 2H, Ar—H). $^{31}$P NMR (162 MHz, CDCl$_3$) δ 53.03.

Synthesis of 46, and 47 followed the general procedure for ligand exchange.

General procedure for ligand exchange of gold nanoclusters (compounds 42, 43, 44, 46 and 47). To a stirring solution of the precursor gold cluster (1.0 μmol) in 3 mL of DCM/water, the exchanging ligand (50 μmol) dissolved in water/DCM (3 mL) was added. The mixture was stirred at room temperature (25° C.) for 12 hours. In the water-soluble compound solutions, the aqueous layer was washed with DCM (3×10 mL), and the combined organic layers were washed with water (3×10 mL). In all exchanges, the crude product was concentrated then purified by gel filtration using SEPHADEX LH-20 beads swollen, packed and eluted using a 4:1 methanol/water solution. Purity was confirmed by TLC followed by $^1$H and $^{31}$P NMR.

Example 5

Scheme 5 shows the synthesis of Compound 49.

Scheme 5

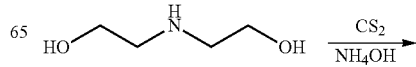

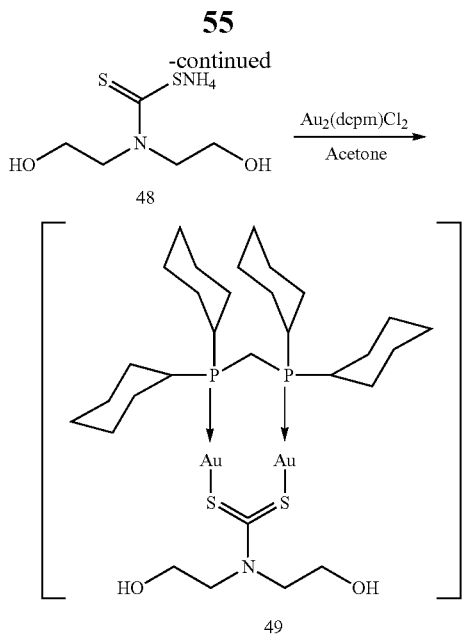

48

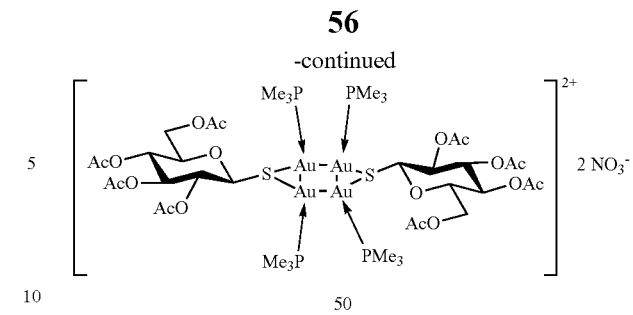

50

Synthesis of 50. AgNO₃ (60 mg, 0.352 mmol) in MeCN was added to Me₃PAuCl (93 mg, 0.302 mmol) at 0° C. in dark. After stirring for 0.5 h, it was filtered. The filtrate was concentrated to around 1 mL then was added diethyl ether. A white precipitate formed, which was collected by centrifugation, and was washed by diethyl ether. After dried in vacuum, it was suspended in DCM, which was added to compound 35 (160 mg, 0.251 mmol) in 2 mL of DCM at 0° C. After stirring for 40 mins, the mixture was filtered through a PTFE syringe filter (0.2 μm) to give a transparent colorless solution. Then it was slightly concentrated without heating. The product was recrystallized by diffusion of diethyl ether into DCM and dried in vacuum overnight to afford the product (62 mg, 27%) as white crystals. $^1$H NMR (500 MHz, CDCl₃) δ 5.42 (d, J=9.7 Hz, 2H), 5.21-5.13 (m, 4H), 5.06-4.99 (m, 2H), 4.24 (d, J=3.3 Hz, 4H), 3.96 (dq, J=6.7, 3.2 Hz, 2H), 2.11 (s, 6H), 2.09 (s, 6H), 2.03 (s, 6H), 1.99 (s, 6H), 1.73 (d, J=11.5 Hz, 36H). $^{13}$C NMR (126 MHz, CDCl₃) δ 170.53, 170.09, 169.69, 169.48, 81.90, 76.39, 75.46, 74.20, 68.11, 62.14, 21.31, 21.03, 20.73, 15.57 (d, J=38.0 Hz).

Synthesis of 48. Ammonium hydroxide solution (25%, 1.4 mL) was added to diethanolamine (2.1 g, 20 mmol) in ethanol (10 mL) at 0° C. Carbon disulfide (1.52 g, 20 mmol) in ethanol (1 mL) was added dropwise with stirring for 10 mins. The reaction was left stand for 5-10 min in a −20° C. freezer. A large amount of white precipitate formed, which was collected by centrifugation and washed by EtOH. After air dry and vacuum dry, the product (3.25 g, 81%) was obtained as a white amorphous powder. $^1$H NMR (400 MHz, D₂O) δ 4.20 (t, J=6.0 Hz, 4H), 3.87 (t, J=6.0 Hz, 4H). $^{13}$C NMR (101 MHz, D₂O) δ 211.15, 59.13, 56.84.

Synthesis of 49. To a solution of Au₂(dcpm)Cl₂ (100 mg, 0.114 mmol) in 20 mL of acetone, compound 48 (24 mg, 0.12 mmol) was added. After stirring for 8 h at rt, the reaction was concentrated on rotavap. The product was precipitated out by water. The precipitate was collected and dried in vacuum. Then it was purified by column chromatography (DCM:MeOH=10:1~8:1) to give the product (106 mg, 91%) as a pale yellow solid. $^1$H NMR (400 MHz, CDCl₃/CD₃OD=12/1) δ 4.30 (s, 4H), 4.03 (t, J=5.1 Hz, 4H), 2.65-2.46 (m, 2H), 2.25 (s, 4H), 2.13-1.89 (m, 16H), 1.80 (d, J=10.2 Hz, 4H), 1.65-1.22 (m, 20H). $^{13}$C NMR (101 MHz, CDCl₃/CD₃OD=12/1) δ 61.19, 59.19, 35.82 (t, J=15.9 Hz), 29.50 (d, J=36.7 Hz), 26.45 (q, J=7.2, 6.7 Hz), 25.53.

Antibacterial assay of gold nanoclusters. Organisms used for MIC and MBC tests included *E. coli* ATCC 25922 CLSI as the control strain and the ESKAPE pathogens: *Enterobacter cloacae* (NCTC 13405, ESBL positive and AmpC enzyme), *Pseudomonas aeruginosa* (NCTC 13437, MDR β-lactams and aminoglycosides), *Acinetobacter baumanni* (NCTC 13420, MDR and ESBL positive), *Klebsiella pneumonia* (ATCC 700603, ESBL positive and SHV-18), *Enterococcus faecalis* (ATCC 51299, high level aminoglycoside resistance), *Staphylococcus aureus* (MRSA JE2 USA300). Liquid cultures of bacteria were grown in log-phase and diluted to 10⁶ CFU/mL. Media used for MIC/MBC was cation-adjusted Muller Hinton broth (Sigma). MIC/MBC was determined by broth microdilution. Compounds were dissolved in either water or DMSO, and the stock solutions were serially diluted with water to the tested concentration range of 256-0.5 μg/mL. Aliquots (100 μL) of the dilutions were mixed with an equal volume of bacterium suspension in a 96 well plate (in triplicates). The plates were incubated at 37° C. for 18 h. Results obtained are presented in Table 3.

Example 6

Scheme 6 shows the synthesis of Compound 50.

Scheme 6

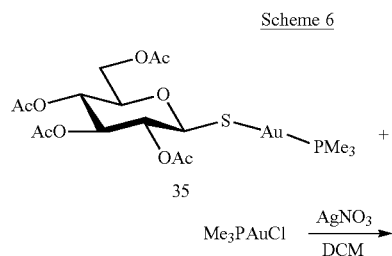

TABLE 3

| MIC (MBC), μg/mL of Au-101 Clusters (41-47) | | | | | | | |
|---|---|---|---|---|---|---|---|
| | A. baumannii NCTC 13420 | P. aeruginosa NCTC 13437 | E. cloacae NCTC 13405 | K. pneumoniae ATCC 700603 | S. aureus JE2 (USA300) | E. faecalis ATCC 51299 | E. coli (control) ATCC 25922 |
| 41 | 64 (64) | >256 | >256 | >256 | 4 (4) | 32 (32) | >256 |
| 42 | >256 | >256 | >256 | >256 | 4 (4) | 16 (16) | >256 |
| 43 | 32 (64) | 32 (32) | >256 | >256 | 2 (2) | 8 (8) | 256 (256) |

TABLE 3-continued

| | MIC (MBC), μg/mL of Au-101 Clusters (41-47) | | | | | | |
|---|---|---|---|---|---|---|---|
| | A. baumannii NCTC 13420 | P. aeruginosa NCTC 13437 | E. cloacae NCTC 13405 | K. pneumoniae ATCC 700603 | S. aureus JE2 (USA300) | E. faecalis ATCC 51299 | E. coli (control) ATCC 25922 |
| 44 | 32 (64) | 32 (32) | >256 | >256 | 2 (2) | 8 (8) | >256 |
| 45 | >256 | >256 | >256 | >256 | 8 (8) | >256 | >256 |
| 46 | >256 | >256. | >256 | >256 | 8 (8) | >256 | >256 |
| 47 | >256 | >256 | >256 | >256 | 4 (4) | 4 (4) | >256 |

Example 5

Antibacterial assay. The minimum inhibitory concentrations (MICs) and the minimum bactericidal concentrations (MBCs) were determined by the broth microdilution method as described in the CLSI (The Clinical & Laboratory Standards Institute) guidelines (*Performance standards for antimicrobial susceptibility testing*: Clinical and Laboratory Standards Institute (CLSI), Twenty-Fifth informational supplement. Document M100-S25: 2009; Vol. 35). All bacterial strains were cultured in cation-adjusted Muller Hinton broth (CAMHB) up to log-phase and then diluted to give a concentration of $7.5 \times 10^5$ CFU/mL. The gold complexes were dissolved in DMSO or water as stock solutions, which were then serially diluted two-fold in a 96-well plate. Aliquots (100 μL) of the dilutions were mixed with equal volumes of the bacterium suspension in a 96 well plate (in triplicates). The plates were incubated at 37° C. for 18 h without shaking. Negative and positive controls were included in the same well plate with wells having the culture medium only and bacteria solution only, respectively. The sample concentration that gave inhibition values above 90% were determined as MICs as calculated from absorbance values at 600 nm (OD600) obtained using a Tecan SPARK 1OM plate reader. To determine minimum bactericidal concentrations (MBCs), agar plates were treated with 5 μL sample solutions from each well, and then incubated at 37° C. for 18 h without shaking. The sample concentration that gave no colony formed on agar plates were determined as MBCs.

Sample preparation. The compounds were dissolved in DMSO at 12.8 mg/mL as the stock solutions, except for compounds 9-17, which were directly dissolved in the culture medium at 12.8 mg/mL. The stock solutions were diluted by the culture medium to the testing concentration at 128 μg/mL (compound 9-17 were diluted to 1,280 μg/mL). The solutions were then serially diluted two fold in a 96-well plate and were used in the cytotoxicity assay immediately.

Cell culture and cytotoxicity assay. A549 cells (ATCC CCL-185) were cultured in high glucose DMEM (Sigma-Aldrich, D6429) supplemented with 10% FBS, 1% penicillin-streptomycin solution (Sigma-Aldrich, P4333), 1% gentamicin solution (Sigma-Aldrich, G1272) and 1% amphotericin B solution (Sigma-Aldrich, A2942) at 37° C. in a humidified atmosphere containing 5% $CO_2$. After cells reached 80%~90% confluency, they were detached and counted using an Invitrogen Countess automated cell counter. Cells with viability over 90% were seeded at a density of $5 \times 10^3$ cells per well in 96-well cell culture plates. After overnight culture, the culture medium in each well removed with a pipet. 80 μL of the compound solutions from each well of the 96-well plate prepared above were transferred to this 96-well plate containing the cells, and the plates were incubated for 20 h. After addition of 8 μL of 110 μg/mL resazurin, the plates were incubated for further 3 h at 37° C. in 5% $CO_2$. The fluorescence intensity was measured using a Tecan M200 Infinite Pro microplate reader at excitation 560 nm, emission 590 nm. $IC_{50}$ were calculated by curve fitting the inhibition values vs. log(concentration) using GraphPad's Prism. The cytotoxicity assays (in triplicate) were repeated twice using freshly prepared cells and compound solutions.

TABLE 4

| $IC_{50}$ (μg/mL)[a] of auranofin and analogs against A549 cells. | | | | | | |
|---|---|---|---|---|---|---|
| 1 | 2 | 3 | 4 | 5 | 6 | 7 |
| 7.7 ± 1.3 | 10.5 ± 0.2 | 30.9 ± 5.8 | 7.9 ± 0.1 | 15.2 ± 0.3 | 29.8 ± 3.2 | 14.4 ± 0.0 |
| 8 | 9 | 10 | 11 | 12 | 13 | 14 |
| 15.8 ± 0.1 | 30.2 ± 0.1 | 16.9 ± 0.5 | 17.2 ± 1.1 | 29.2 ± 4.8 | 32.9 ± 4.6 | 31.0 ± 2.4 |
| 15 | 16 | 17 | 18 | 19 | 20 | 21 |
| 52.2 ± 1.0 | 43.0 ± 3.7 | 35.5 ± 0.9 | 4.3 ± 0.2 | 7.5 ± 0.1 | 6.5 ± 1.1 | 7.2 ± 0.7 |
| 22 | 23 | 24 | 25 | 26 | 27 | 28 |
| 5.5 ± 1.3 | 3.1 ± 0.2 | 7.3 ± 1.7 | 6.4 ± 2.4 | 4.6 ± 0.2 | 12.3 ± 3.1 | 15.9 ± 0.7 |
| 29 | 30 | 31 | 32 | 33 | 34 | 35 |
| 9.5 ± 0.1 | 4.7 ± 0.0 | 12.0 ± 1.8 | 9.4 ± 1.7 | 13.2 ± 1.0 | 85.6 ± 26.1 | 13.1 ± 2.3 |
| 36 | 37 | 38 | 39 | 40 | | |
| 2.5 ± 0.3 | 3.1 ± 0.1 | 3.8 ± 0.1 | 2.9 ± 0.1 | 18.3 ± 2.2 | | |

Regarding Table 4, [a]Data are presented as mean±S.E.M. from two independent experiments.

Log P Determination: Calibration curves. Milli-Q Water (150 mL) was added to n-octanol (150 mL), and the mixture was stirred for 3 days to allow both phases to reach saturation. The gold standard solution (1000 ppm Au in hydrochloric acid, Fisher Scientific) was diluted to 1, 2, 3, 4 and 5 ppm with n-octanol-saturated water, and the absorbance of the resulting solutions was measured by flame atomic absorption spectroscopy (FAAS, Agilent Technology 200 Series AA, equipped with a gold HC Lamp-Au coded). The absorbance data were plotted against Au concentration, and the resulting calibration curve was used for determining the concentration of the analogs in the aqueous phase.

To construct the standard calibration curve of the Au concentration in the n-octanol phase, compound 27 was used. The Au concentration in compound 27 was first calibrated against the aqueous gold standard. For this, 0.440 mg of compound 27 was weighed on a Sartorius MC5 microbalance, and then added to 22 mL of n-octanol-saturated water. After the compound was fully dissolved, the absorbance of the solution was measured by FAAS, and the Au concentration was determined from a first calibration curve to be 9.88 ppm. This data was then used to construct the standard calibration curve of the Au concentration in the n-octanol phase. For this, solutions of varying concentrations (0.99, 2.47, 4.94, 5.93, 9.88 ppm) of compound 27 in water-saturated n-octanol were prepared. The absorbance was measured by FAAS, and the data were plotted against the Au concentration to provide a second calibration curve, which was used for determining the Au concentration of the analogs in the n-octanol phase.

Determination of Au concentrations: Method 1. 0.5 to 1 mg of compound was weighed into a 2-mL Eppendorf tube containing 2 mL of n-octanol-saturated water. After shaking for about 4 h, the solution was centrifuged at 6000 rpm for 3 min. 1 mL of the supernatant was transferred to a new tube containing 1 mL of water-saturated n-octanol, and the mixture was shaken for 1 h. After centrifugation at 6000 rpm for 5 min, the two layers were collected and the gold concentration in each layer was determined by FAAS by comparing the absorbance to the first and second calibration curves.

Determination of Au concentrations: Method 2. This method was used for compounds 22, 23, 30-34, 36-40, which gave very low absorbance reading on FAAS, likely due to the low solubility of these compounds in n-octanol-saturated water. For Method 2, 0.6 to 1 mg of compound was weighed into a 2-mL Eppendorf tube containing 1 mL of n-octanol-saturated water and 1 mL of water-saturated n-octanol. After shaking for 3-4 h, the mixture was centrifuged, and all liquid was transferred to a 15-mL tube. The liquid was then diluted with 2 mL of n-octanol-saturated saturated water and 2 mL of water-saturated n-octanol, and the mixture was shaken for another hour. After centrifugation at 6000 rpm for 5 min, the two layers were collected and the gold concentration in each layer was determined by FAAS by comparing the absorbance to the first and second calibration curves.

Log $P$ was calculated as follows: log $P$=log[compound]$_{oct}$/[compound]$_{water}$

TABLE 5

| | *A. baumannii* NCTC 13420 | *P. aeruginosa* NCTC 13437 | *E. cloacae* NCTC 13405 | *K. pneumoniae* ATCC 700603 | *S. aureus* JE2 (USA300) | *E. faecalis* ATCC 700221 | *E. coli* ATCC 25922 | Log P |
|---|---|---|---|---|---|---|---|---|
| 1 | 47 (47) | 377 (377) | 189 (189) | 377 (377) | 0.04 (0.09) | 0.2/0.09 (0.4) | 24 (24) | 0.56 |
| 2 | 47 (94) | 377 (377) | 377 (377) | >377 | 0.04 (0.09) | 0.2/0.4 (0.4) | 24 (24) | 0.38 |
| 3 | 24 (47) | 189 (189) | 47 (94) | 189 (189) | 0.04/0.09 (0.09) | 0.09 (0.4) | 12 (12) | 0.26 |
| 4 | 82 (164) | >328 | >328 | >328 | 0.01 (0.01) | 0.08 (0.2) | 21 (21) | 1.01 |
| 5 | 33 (33) | 132 (132) | 66 (66) | >265 | 0.008 (0.06) | 0.03/0.06 (0.1) | 17 (17) | 0.45 |
| 6 | 66 (132) | 132 (132) | 265 (265) | >265 | 0.03 (0.1) | 0.1 (0.3) | 33 (33) | 1.04 |
| 7 | 12 (12) | >194 | 24 (24) | >194 | 0.003/0.006 (0.006) | 0.05 (0.09) | 24 (24) | −0.28 |
| 8 | 76/19 (19) | >303 | 152 (303) | >303 | 0.04/0.009 (0.1) | 0.04/0.07 (0.3) | 152/323 (152) | −0.36 |
| 9 | 63/16 (251) | 502 (502) | 125 (125) | 502 (502) | 0.06/0.1 (0.5) | 0.1 (2) | 31 (31) | −0.81 |
| 10 | 31 (31) | 251 (251) | 63 (63) | 251 (251) | 0.02 (0.1) | 0.1/0.2 (0.5) | 16 (16) | −0.73 |
| 11 | 31 (63) | 502 (502) | 125 (251) | 502 (502) | 0.02/0.06 (0.1) | 0.1/0.06 (0.5) | 16 (16) | −0.59 |
| 12 | 15/29 (116) | 464 (464) | 116 (232) | 464 (464) | 0.02 (0.05) | 0.05/0.1 (0.5) | 7/4 (7) | −0.89 |
| 13 | 24/48 (190) | 381 (381) | 190 (190) | 381 (381) | 0.02/0.05 (0.09) | 0.09 (0.4) | 24 (24) | −1.81 |
| 14 | 24 (24) | 381 (381) | 190 (190) | >381 | 0.09/0.04 (0.09) | 0.09/0.2 (0.4) | 12 (12) | −1.69 |
| 15 | 17/4 (17) | >547 | 4/9 (17) | 34 (34) | 0.3/0.5 (1) | 0.3/0.5 (0.5) | 9 (9) | −1.63 |
| 16 | 17/9 (17) | >547 | 4 (4) | 34 (34) | 0.3 (0.3) | 0.3/0.5 (0.5) | 9 (9) | −1.88 |
| 17 | 16/8 (16) | >503 | 8/16 (16) | 31 (126) | 0.5 (0.5) | 0.2/0.5 (0.5) | 8/31 (31) | −2.03 |
| 18 | 19/75 (>603) | 302 (302) | 75 (603) | >603 | 0.02 (0.6) | 0.6 (1) | 151 (151) | 2.20 |
| 19 | 18/36 (18) | 291 (291) | 18/73 (36/73) | 146 (146) | 0.009 (0.6) | 0.02 (0.1) | 36 (36) | 0.61 |

TABLE 5-continued

MIC$^a$ (MBC), μM/mL of Compounds 1-40

| | A. baumannii NCTC 13420 | P. aeruginosa NCTC 13437 | E. cloacae NCTC 13405 | K. pneumoniae ATCC 700603 | S. aureus JE2 (USA300) | E. faecalis ATCC 700221 | E. coli ATCC 25922 | Log P |
|---|---|---|---|---|---|---|---|---|
| 20 | 18(18) | 146 (146) | 36 (36) | 36 (36) | 0.07/0.02 (0.07) | 0.02 (0.1) | 9 (9) | 1.36 |
| 21 | 35 (35) | 282 (282) | 141 (141) | 141 (141) | 0.02 (0.3) | 0.02/0.1 (0.3) | 35 (35) | 2.01 |
| 22 | >546 | >546 | >546 | >546 | 0.0004/0.02 (0.02) | 0.06/0.1 (0.5) | >546 | >3.28 |
| 23 | 520 (>520) | >520 | >520 | >520 | 0.02/0.1 (0.2) | 0.02 (0.2) | >520 | >3.18 |
| 24 | 10 (82) | 41 (41) | 5/10 (82) | 20 (20) | 0.03 (0.03) | 0.2/0.3 (0.6) | 10 (10) | 1.19 |
| 25 | 19 (76) | 305 (305) | 38 (152) | 76 (76) | 0.005/0.02 (0.02) | 0.1/0.3 (0.6) | 76 (76) | 1.75 |
| 26 | 37/74 (149) | 149 (149) | 37 (149) | 149 (149) | 0.009 (0.1) | 0.6 (1) | 74 (74) | 2.08 |
| 27 | 6/3 (23) | 23/91 (91) | 3 (3) | 11 (23) | 0.3 (0.7) | 0.3 (0.3) | 1/6 (11) | −0.15 |
| 28 | 7/13 (13) | 52 (52) | 3 (3) | 7/13 (13) | 0.1/0.2 (1.6) | 0.4 (3) | 7 (7) | 0.16 |
| 29 | 11/23 (23) | 92 (183) | 23 (23) | 46 (46) | 0.001/0.02 (0.2) | 0.09/0.2 (0.7) | 23 (23) | 1.74 |
| 30 | 74/147 (147) | 74 (74) | >589 | 147 (147) | 2 (4) | 5 (5) | >589 | >3.99 |
| 31 | 16/129 (518) | >518 | >518 | >518 | 1/2 (4) | 4 (4) | >518 | >3.94 |
| 32 | >438 | >438 | >438 | >438 | 2 (3) | 3 (3) | >438 | >4.09 |
| 33 | 29/58 (233) | >467 | >467 | >467 | 1/(4) | 2/4 (4) | >467 | >4.04 |
| 34 | >366 | >366 | >366 | >366 | 3/1 (11) | >366 | >366 | >3.94 |
| 35 | 6/13 (101) | 101 (101) | 3 (3) | 13 (13) | 0.1 (0.2) | 0.2/0.4 (0.8) | 6 (6) | 0.35 |
| 36 | 84 (>336) | >336 | >336 | >336 | 3 (3) | 3/5 (3) | >336 | >4.32 |
| 37 | >311 | >311 | >311 | >311 | 1/2 (2) | 5 (5) | >311 | >3.87 |
| 38 | >281 | >281 | >281 | >281 | 1 (2) | 2/4 (4) | >281 | >3.03 |
| 39 | >292 | >292 | >292 | >292 | 1 (2) | 2/5 (5) | >292 | >3.04 |
| 40 | >249 | >249 | >249 | >249 | 4 (8) | 31 (62) | >249 | >3.55 |

Table 5 shows the MIC values for Compounds 1-40.

Regarding Table 5, $^a$MIC was repeated twice. Only one value is presented unless otherwise stated.

Selection of bacteria. The ESKAPE pathogens were chosen as they are responsible for the majority of nosocomial infections and also as they provide a good scope of strains including both Gram-negative and Gram-positive species. *A. baumannii* NCTC 13420 was originally identified in 24 hospitals in the UK during 2000-2003, which produced OXA-51-like β-lactamases, and was highly resistant to ampicillin, piperacillin, piperacillin/tazobactam, ceftazidime, cefotaxime, gentamicin and ciprofloxacin. *P. aeruginosa* NCTC13437 produces VIM-10 metallo-carbapenemase and VEB-1 (Vietnamese extended-spectrum beta-lactamase). Wild-type strain *E. cloacae* NCTC 13405 (originally named *E. cloacae* 684) was isolated from patients at the London Hospital during 1982-1983. This strain has inducible AmpC β-lactamase and is resistant to ampicillin/amoxicillin and cefoxitin. *K. pneumoniae* ATCC 700603 was isolated from the urine of a hospitalized patient in Richmond, Va. in 1994, and it produces SHV-18 extended spectrum beta-lactamase (ESBL). JE2 (USA300) is a methicillin-resistant *S. aureus* (MRSA) strain, also resistant to beta-lactams, ciprofloxacin, tetracycline, macrolides (erythromycin), lincosamides (clindamycin), streptogramin B, and mupirocin. *E. faecium* ATCC 700221, a positive fecal VRE (vancomycin-resistant *enterococcus*) isolate, is resistant to several antibiotics including vancomycin and teicoplanin. The quality control strain, Gram-negative *E. coli* ATCC 25922, was included in all assays and validated with ciprofloxacin and teicoplanin.

In vitro antimicrobial activities. The data for auranofin (1) is consistent with previous reports that auranofin is active against Gram-positive bacteria but inactive towards Gram-negative bacteria. Auranofin can be made active towards Gram-negative bacteria by changing the ligands coordinated to $Au^1$. While auranofin itself has no activity against all Gram-negative pathogens, some analogs become active against *P. aeruginosa*. The thiol ligand is important for the activity in addition to modulating the toxicity. For instance, replacing tetraacetylated thioglucose with 2-mercaptoethanol (21) increased the activity of auranofin by 5-19 times for all Gram-negative pathogens while decreasing the cytotoxicity by 1.6 times. The vast majority of the analogs showed either similar or lower mammalian cell toxicity compared to auranofin.

Gram-positive activities. Among the thio sugar analogs (1-14), the TreNAc$_7$ ligand (7) showed the highest activity enhancement of 7 fold and MIC/MBC of 6 nM against *S. aureus* (Table 3). Compounds 19, 22, 25, 26 also showed MIC values in the nanomolar range against *S. aureus* are analogs. Compounds 19-21 showed promising activity against *E. faecium*. Compound 19-21 have an electron-donating group on the benzene thiol ligand, resulting in an 8 fold improvement in activity over auranofin. Among the compounds tested, triethylphosphine appears to be the preferred phosphine ligand for the two Gram-positive strains. Replacing triethylphosphine with trimethylphosphine (e.g., 35) did not improve the activity. The tri-n-butylphosphine and all triarylphosphines drastically decreased the activity.

For the Gram-negative strains, there was a clear preference for aliphatic over aromatic phosphines. Analogs bearing triarylphosphines with either electron-withdrawing or electron-donating groups failed to show activity against the Gram-negative strains tested (37-40). The Au[1] chloride complexes (31-34) gave similar results. Among the aliphatic phosphine ligands, there was a preference for the trimethylphosphine ligand. Analogs prepared by replacing triethylphosphine with trimethylphosphine led to sizable improvement in activity (35, 15-17, 27). Increasing the alkyl chain length to n-butyl drastically decreased the activity for all Gram-negative strains tested except for *P. aeruginosa* (compare 30 with 29 and 35 with 1).

Auranofin was slightly active against *A. baumannii*, with an MIC/MBC of 47 µM. Changing the thio sugar structure had very little impact on the activity (2-14), and so were most analogs with an aliphatic or an aromatic thiol (18-26). Analogs having a trimethylphosphine ligand showed the best activity against *A. baumannii*, with MIC of 13 µM and 5.7 µM for 35 and 27, respectively.

Lipophilicity of the compounds appears to play a role in the activity of the compounds against *P. aeruginosa*. For example, the trimethylphosphine and de-protected thio sugar analogs 15-17 (Log P=−1.63--2.03) improved the activities by 3-44 fold over auranofin against all Gram-negative strains except for *P. aeruginosa* where the activity was completely lost. Compound 35 showed a four-fold improvement in activity over 15 against *P. aeruginosa*. It appears that *P. aeruginosa* is more sensitive to the structure of the thiol moiety than the phosphine ligand. Among the analogs that showed activity against *P. aeruginosa* (24, 28, 27), none of them bears a thio sugar ligand. The most promising analog is compound 24 that has a mercaptoethanol ligand (MIC/MBC at 41 µM), which is 9 times better than auranofin. Increasing the chain length of trialkylphosphine from methyl to ethyl to n-butyl led to drastic decrease in activity for all other Gram-negative strains, whereas in the case of *P. aeruginosa*, the effects were minimal (compare 28-30, 27 with 24). The effect on MIC was a 2 fold decrease from 28 (methyl) to 29 (ethyl), and the MIC increased from 29 (ethyl) to 30 (n-butyl).

Among the Gram-negative strains tested, *E. cloacae* appears to be the most affected by the structures of the thio sugar and the phosphine ligands. The structure of the phosphine ligand showed the largest impact on the activity against *E. cloacae*. Replacing triethylphosphine in auranofin with trimethylphosphine provided 35, resulting in a MIC/MBC of 3.1 µM, which is 61 fold lower than auranofin. Compound 16, which combines a trimethylphosphine ligand and a deprotected Gal sugar, had similar activity. Aromatic thiols having strong electron withdrawing groups (22, 23) completely diminished the activity. The thiol ligand, mercaptoethanol, combined with the phosphine ligand, trimethylphosphine, yielded analog 27 which had a MIC/MBC of 2.9 µM, a 65 fold improvement over auranofin.

Auranofin is ineffective against *K. pneumoniae*, with an MIC/MBC of 377 µM. Changing the thio sugar structure had no impact on the activity (i.e., 1-14). Replacing the thio sugar with an aliphatic or an aromatic thiol ligand yielded a number of analogs that showed good activities (i.e., 18-26). The p-aminobenzene thiol (20) lowered the MIC/MBC of auranofin by 10 fold to 36 µM. The mercaptoethanol ligand (21) lowered the MIC/MBC further to 20 µM. Trimethylphosphine is again the best phosphine ligand. All trimethylphosphine analogs have good activities against *K. pneumoniae* with the best candidate 27 having the MIC of 11 µg/mL, which is 34 fold lower than auranofin.

Lipophilicity. For Group 1 compounds having a thio sugar ligand, the de-protected thio sugar (9-14, Table 5) did not impact the activity of the resulting analogs for either the Gram-negative or the Gram-positive strains, even though the log P increased by more than one unit. Among the Group 2 compounds having an aromatic or aliphatic thiol ligand, the analogs having moderate log P values (1-2) exhibited better activity, whereas analogs 22 and 23 with high log P (>3) had no activity against all Gram-negative strains (Table 5). In the trialkyl- and triaryl-phosphine series of Group 3 compounds, the in vitro activity correlated well with the lipophilicity. Analogs having a high log P (>4), including tri-n-butylphosphine and all triarylphosphine analogs, showed either decreased or no activity (Table 5). The de-protected thio sugar analogs 15-17 exhibited good activity against all Gram-negative strains except for *P. aeruginosa*. Compounds that are active against *P. aeruginosa* are moderately lipophilic with a positive log P of less than 2.

TABLE 6

| | MIC µg/mL of Compounds 1-40 | | |
|---|---|---|---|
| | *C. albicans* | *C. neoformans* | |
| | ATCC 90028 | ATCC 208821 | KN99 |
| 1 | >32 | 8 | 16 |
| 2 | >32 | >32 | N.D. |
| 3 | >32 | >32 | N.D. |
| 5 | >32 | >32 | N.D. |
| 6 | >32 | >32 | N.D. |
| 7 | >32 | 32 | 16 |
| 19 | N.D. | N.D. | 2 |

Example 7

Scheme 7a shows the synthesis of Compound 51.

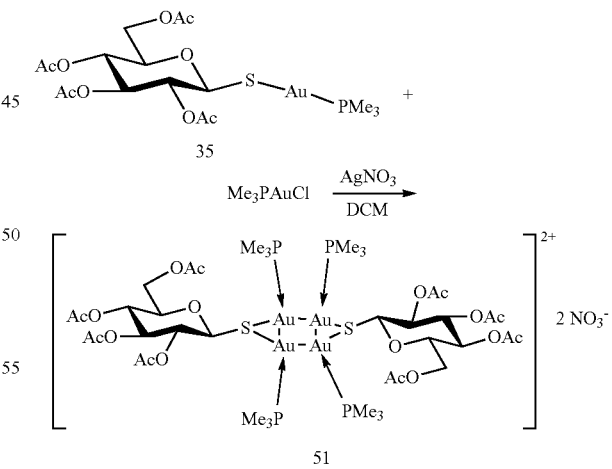

Compound 51. AgNO$_3$ (60 mg, 0.352 mmol) in MeCN was added to Me$_3$PAuCl (93 mg, 0.302 mmol) at 0 C in dark. After stirring for 0.5 h, it was filtered. The filtrate was concentrated to around 1 mL then diethyl ether was added. A white precipitate formed, which was collected by centrifugation, and was washed by diethyl ether. After dried under vacuum, it was suspended in DCM, which was added to compound 35 (160 mg, 0.251 mmol) in 2 mL of DCM at 0 C. After stirring for 40 mins, the mixture was filtered through a PTFE syringe filter (0.2 μm) to give a transparent colorless solution, which was slightly concentrated without heating. The product was recrystallized by diffusion of diethyl ether into DCM and dried in vacuum overnight to afford the product (62 mg, 27%) as white crystals. $^1$H NMR (500 MHz, CDCl$_3$) δ 5.42 (d, J=9.7 Hz, 2H), 5.21-5.13 (m, 4H), 5.06-4.99 (m, 2H), 4.24 (d, J=3.3 Hz, 4H), 3.96 (dq, J=6.7, 3.2 Hz, 2H), 2.11 (s, 6H), 2.09 (s, 6H), 2.03 (s, 6H), 1.99 (s, 6H), 1.73 (d, J=11.5 Hz, 36H). $^{13}$C NMR (126 MHz, CDCl$_3$) δ 170.53, 170.09, 169.69, 169.48, 81.90, 76.39, 75.46, 74.20, 68.11, 62.14, 21.31, 21.03, 20.73, 15.57 (d, J=38.0 Hz).

Scheme 7b shows the synthesis of Compound 52.

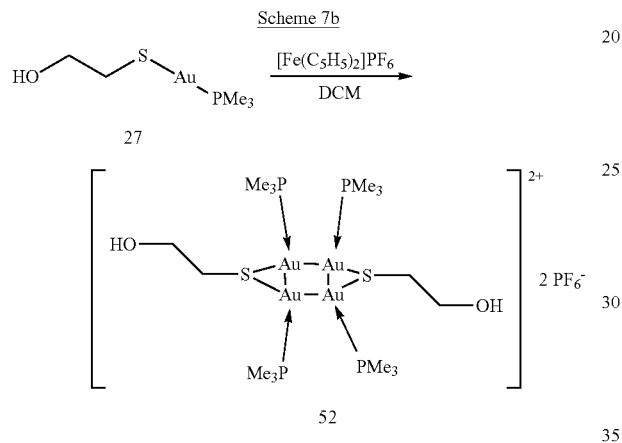

Compound 52. To a solution of compound 27 (200 mg, 0.57 mmol) in 100 mL of DCM, ferrocenium hexafluorophosphate (95 mg, 0.286 mmol) was added. The solution was stirred at 0° C. for 23 h, and was then filtered. The filtrate was concentrated. After transferred to a 20 mL scintillation vial, it was placed in ether vapor environment at 4° C. Yellow solids formed at bottom of the vials. After pipetting out the supernatant solution, the solids were washed by diethyl ether. The white solid was re-dissolved in 5 mL of DCM and was placed in ether vapor environment at 4° C. for 2 days. The product obtained was the title compound co-crystallized with (PMe$_3$)$_2$AuPF$_6$. $^1$H NMR (500 MHz, CD$_2$Cl$_2$) δ 3.86 (t, J=5.6 Hz, 4H), 3.35 (t, J=6.1 Hz, 4H), 2.55 (s, 2H), 1.70 (d, J=11.3 Hz, 36H), 1.64 (t, J=4.2 Hz, 18H, (PMe$_3$)$_2$AuPF$_6$). $^{13}$C NMR (101 MHz, CD$_2$Cl$_2$) δ 65.72, 35.14, 15.59 (d, J=38.4 Hz), 14.81 (t, J=18.9 Hz, (PMe$_3$)$_2$AuPF$_6$). $^{31}$P NMR (162 MHz, CD$_2$Cl$_2$) δ 8.26 ((PMe$_3$)$_2$AuPF$_6$), −4.05, −141.62 (hept, $^1J_{PF}$=713 Hz, PF$_6$).

Scheme 7c shows the synthesis of Compound 53.

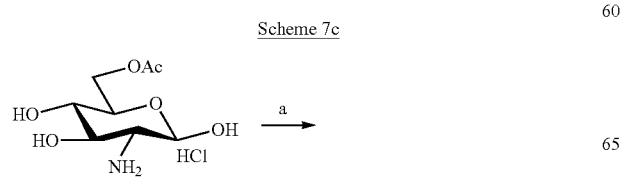

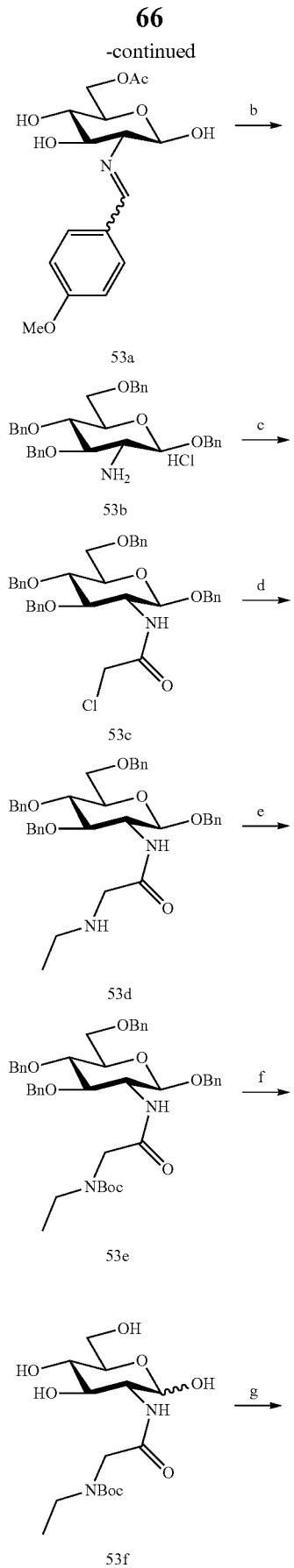

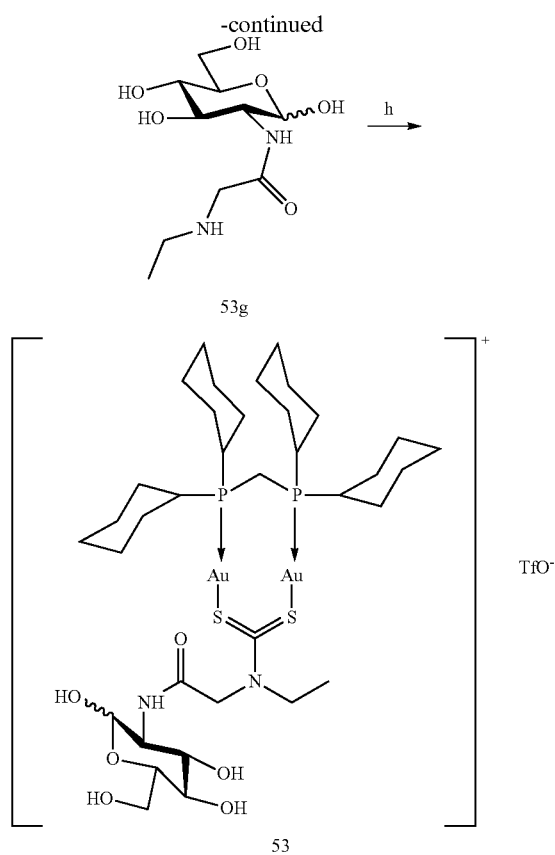

Reagents and conditions for Scheme 7c: a) p-anisaldehyde, 1 M NaOH, rt, overnight (89%); b) i: BnBr, NaH, DMF, rt, overnight; ii: 5 M HCl, acetone, 60° C., 25 min (42%); c) (ClCH$_2$CO)$_2$O, pyridine, DCM, rt, overnight (88%), d) EtNH$_3$, MeCN, rt, overnight (75%); e) (Boc)$_2$, TEA, DCM, overnight (98%). f) Pd/C, H$_2$, MeOH, 20 h (91%). g) TFA. DCM (quant). h) i) CS$_2$, aq. NH$_{40}$H, MeOH; ii) Au$_2$dcmpCl$_2$, acetone, overnight (47%).

Compound 53a. D-Glucosamine hydrochloride (3.0 g, 13.9 mmol) was dissolved in 1 M NaOH (15 mL), and p-anisaldehyde (2.0 mL, 16.7 mmol) was added. The mixture was stirred at RT for 0.5 h then was briefly sonicated for 1 min, and was stirred for another 0.5 h. The white precipitate was filtered off, washed with cold water (30 mL) and EtOH/Et$_2$O (30 mL, 1:1, v/v), and dried under high-vacuum, yielding the product as a white powder (3.71 g, 89%). $^1$H NMR (500 MHz, DMSO-d$_6$) δ 8.11 (s, 1H), 7.71-7.66 (m, 2H), 7.02-6.96 (m, 2H), 6.51 (d, J=6.8 Hz, 1H), 4.90 (d, J=5.3 Hz, 1H), 4.79 (d, J=5.6 Hz, 1H), 4.69 (dd, J=7.7, 6.7 Hz, 1H), 4.52 (t, J=5.8 Hz, 1H), 3.80 (s, 3H), 3.73 (ddd, J=11.6, 5.6, 2.2 Hz, 1H), 3.48 (dt, J=11.8, 6.0 Hz, 1H), 3.45-3.37 (m, 1H), 3.23 (ddd, J=9.7, 5.9, 2.2 Hz, 1H), 3.14 (ddd, J=9.7, 8.7, 5.3 Hz, 1H), 2.79 (dd, J=9.3, 7.6 Hz, 1H).

Synthesis of 53b. Compound 53a (3.64 g, 12.2 mmol) and BnBr (7.27 mL, 61.2 mmol) in DMF (40 mL), NaH (60% in mineral oil, 2.82 mg, 73.5 mmol) was added in two portions in ice/salt bath. The mixture was allowed to reach rt 30 mins after adding NaH. Then the reaction was stirred overnight and quenched by slow addition of ethyl acetate. The mixture was poured into 500 mL of water and extracted by ethyl acetate 3 times. The combined organic layer was washed by brine, dried on Na$_2$SO$_4$. After removal of the solvent, the reside was purified by flash column chromatography (hexanes:ethyl acetate=5:2 containing 5% TEA) to afford a yellow oil. After dissolved in acetone (60 mL), 5 M HCl solution (3 mL) was added. The solution was stirred at 60° C. for 25 min, a large amount precipitate formed. After cooled to rt, it was filtered off, and washed by cold acetone twice, dried in vacuum overnight to give the product as a white amorphous powder (2.95 g, 42% over 2 steps). $^1$H NMR (500 MHz, DMSO-d$_6$) δ 8.60 (s, 2H), 7.50-7.44 (m, 2H), 7.43-7.26 (m, 15H), 7.19-7.13 (m, 3H), 4.91 (d, J=11.0 Hz, 1H), 4.88 (d, J=8.4 Hz, 1H), 4.84 (d, J=11.7 Hz, 1H), 4.81 (d, J=11.0 Hz, 1H), 4.71 (d, J=11.6 Hz, 1H), 4.66 (d, J=11.0 Hz, 1H), 4.58 (d, J=12.2 Hz, 1H), 4.56 (d, J=11.0 Hz, 1H), 4.52 (d, J=12.2 Hz, 1H), 3.98 (t, J=9.5 Hz, 1H), 3.75-3.64 (m, 3H), 3.61 (ddd, J=9.8, 3.9, 2.3 Hz, 1H), 3.05 (dd, J=9.9 and 8.8 Hz, 1H).

Compound 53c. To a solution of Compound 53b (1.39 g, 14.8 mmol) in 20 mL of DCM, pyridine (585 μL, 7.24 mmol) was added. The solution was brought to 0° C. Chloroacetic anhydride (612 mg, 3.12 mmol) was then added. The reaction solution was stirred overnight, and was poured into 50 mL 1 M HCl solution followed by extraction with DCM (50 mL-3). The combined organic phase was washed by saturated NaHCO$_3$, brine, dried on MgSO$_4$. After removing the solvent, the residue was purified by flash column chromatography (ethyl acetate:DCM=1:15) to afford the product (1.31 g, 88%) as a white solid. $^1$H NMR (500 MHz, CDCl$_3$) δ 7.40-7.17 (m, 25H), 6.57 (d, J=8.3 Hz, 1H, NH), 4.87 (d, J=12.3 Hz, 1H), 4.80-4.74 (m, 3H), 4.65-4.52 (m, 5H), 3.96 (dd, J=9.7, 8.2 Hz, 1H), 3.79 (d, J=2.5 Hz, 2H), 3.78-3.66 (m, 4H), 3.57 (ddd, J=9.3, 4.5, 2.6 Hz, 1H). $^{13}$C NMR (126 MHz, CDCl$_3$) δ 166.02, 138.28, 138.08, 137.51, 128.70-127.60 (aromatic), 98.82, 80.51, 78.63, 75.03, 74.77, 74.68, 73.61, 70.71, 69.07, 56.70, 42.61.

Compound 53d. EtNH$_3$ (15 mmol, 676 mg) in MeCN solution (30 mL) was added to a 10 mL round bottle flask containing compound 53c (1.31 g, 2.13 mmol). The reaction was stirred at rt overnight. After removal of the solvent by rotavap evaporation, the residue was directly purified by column chromatography (ethyl acetate:DCM=2:1 with 3% TEA) to afford the product as a white solid (994 mg, 75%). $^1$H NMR (500 MHz, CDCl$_3$) δ 7.39-7.22 (m, 18H), 7.22-7.17 (m, 2H), 4.89 (d, J=12.0 Hz, 1H), 4.85-4.76 (m, 3H), 4.66-4.62 (m, 2H), 4.60-4.53 (m, 3H), 4.05 (dd, J=10.0, 8.4 Hz, 1H), 3.78 (dd, J=10.8, 2.4 Hz, 1H), 3.74 (dd, J=10.8, 4.5 Hz, 1H), 3.71-3.64 (m, 2H), 3.59 (ddd, J=9.5, 4.5, 2.4 Hz, 1H), 3.07 (s, 2H), 2.48 (q, J=7.2 Hz, 2H), 0.96 (t, J=7.1 Hz, 3H). $^{13}$C NMR (126 MHz, CDCl$_3$) δ 172.15, 138.73, 138.38, 138.28, 137.78, 128.60-127.55 (aromatic), 99.54, 81.57, 78.71, 75.13, 74.72, 73.61, 70.81, 69.19, 56.38, 52.65, 44.42, 15.37.

Compound 53e. To a solution of compound 53d (1.02 g, 1.64 mmol) in 25 mL of DCM, (Boc)$_2$O (536 mg, 2.45 mmol) and TEA (1.0 mL) was added. The solution was stirred overnight. After concentrated by rotavap evaporation, it was directly purified by flash column chromatography (ethyl acetae:hexanes=1:2) to give the product (1.16 g, 98%) as a white solid. $^1$H NMR (400 MHz, CDCl$_3$) δ 7.54-6.97 (m, 25H), 6.76 (s, 1H, NH), 4.89 (d, J=11.9 Hz, 1H), 4.83 (d, J=7.8 Hz, 1H), 4.78-4.67 (m, 3H), 4.64-4.45 (m, 4H), 4.02 (dd, J=9.2 and 8.4 Hz, 1H), 3.91-3.55 (m, 7H), 3.12 (d, J=6.7 Hz, 2H), 1.37 (s, 9H), 0.97 (t, J=6.8 Hz, 3H). $^{13}$C NMR (101 MHz, CDCl$_3$) δ 170.05, 155.95, 138.17, 138.06, 137.93, 137.40, 128.30-127.00 (aromatic), 99.22, 81.19, 80.26, 78.05, 74.70, 74.35, 73.21, 70.47, 68.85, 56.32, 50.84, 43.20, 28.11, 12.99.

Compound 53f. Compound 53e (1.1 g, 0.152 mmol) was dissolved in 50 mL of methanol. Then 160 mg of Pd/C (10% w) was added to the solution. The reaction mixture was stirred under $H_2$ atmosphere for 20 h. Then it was filtered through celite. The filtrate was collected. After removal of the solvent, the residue was purified by column chromatography (DCM:MeOH=5:1-3:1). The afforded product was re-dissolved in water and lyophilized to give the product as a white solid (501 mg, 91%). $^1$H NMR (400 MHz, $D_2O$) δ 5.07 (s, 1H, H-1α), 3.71 (ddd, J=52.9, 25.5, 11.0 Hz, 9H), 3.46 (s, 1H), 3.40-3.28 (m, 3H), 3.26-3.09 (m, 4H), 1.31 (d, J=17.6 Hz, 12H), 1.07-0.90 (m, 6H). $^1$H NMR (400 MHz, $D_2O$) δ 5.20 (s, 1H, H-1α), 4.74 (d, J=8.32 Hz, 1H, H-1β), 4.10-3.66 (m, 9H, 4 β-anomer-H and 5 α anomer-H), 3.59 (s, 1H, β-anomer-H), 3.54-3.41 (m, 2H, β-anomer-H and α anomer-H), 3.40-3.23 (m, 2H, $CH_2CH_3$), 1.47 (s, 9H, $C(CH_3)_3$ of p anomer), 1.42 (s, 9H, $C(CH_3)_3$ of p anomer), 1.20-1.03 (m, 3H, $CH_2CH_3$). $^1$H NMR (101 MHz, $D_2O$) δ 172.72, 172.44, 172.04, 157.26, 156.88, 156.77, 94.96, 94.82, 90.98, 81.84, 75.90, 73.77, 71.56, 70.89, 70.76, 70.32, 70.22, 69.96, 60.88, 60.75, 56.96, 56.68, 54.02, 50.15, 49.76, 49.57, 43.89, 43.60, 43.40, 43.18, 27.89, 27.79, 27.72, 12.92, 12.67, 12.52.

Compound 53g. Compound 53f (100 mg, 0.274 mmol) was suspended in 3 mL of DCM. Then 2 mL of TFA was added dropwise. After stirring at rt for 20 mins, the solvent was removed by rotavap evaporation. After co-evaporated with toluene 3 times, the product was further dried in vacuum overnight to afford the product (78 mg, quant.) as a white solid. $^1$H NMR (400 MHz, $D_2O$) δ 5.09 (d, J=3.5 Hz, 1H, H-1α), 4.61 (d, J=8.4 Hz, 1H. H-1β), 3.82 (dd, J=10.7, 3.5 Hz, 1H, H-2a), 3.80 (s, 2H, $CH_2CONH$), 3.78-3.56 (m, 7H, H, H-5a, H-2β, H-3α, H-6aα, H-6bα, H-6aβ, H-6bβ), 3.49-3.27 (m, 4H, H-3β, H-4α, H-4β, H-5β), 3.03 (qd, J=7.3, 1.5 Hz, 2H, $CH_2CH_3$), 1.19 (t, J=7.3 Hz, 3H, $CH_2CH_3$). $^{13}$C NMR (101 MHz, $D_2O$) δ 166.64, 166.34, 162.68 (q, J=35.9 Hz), 116.14 (q, J=291.1 Hz), 94.61 (C1β), 90.68 (C1α), 75.87, 73.65, 71.47, 70.72, 69.96, 69.78, 60.60, 60.46, 56.63, 53.99, 47.51, 47.40, 42.88, 10.29.

Compound 53. Compound 53g (70 mg, 0.196 mmol) in MeOH, $CS_2$ (22 mg, 0.294 mmol) and ammonium hydroxide (25%, 91 μL) was added in ice bath. The solution was stirred at rt for 1 h. The solvent was removed by rotavap evaporation. The crude product was mixed with $Au_2dcmpCl_2$ (171 mg, 0.196 mmol) in 10 mL of acetone. The mixture was stirred at rt overnight. LiOTf (306 mg, 1.96 mmol) was added. After stirring for 2 h, 20 mL of water was added. The mixture was extracted by DCM/MeOH=10/1 twice. The combined organic phase was died on $Na_2SO_4$. After evaporation of the solvent, the residue was purified by column chromatography (DCM:MeOH=10:1~5:1) to give the product as a pale yellow solid (120 mg, yield=47%, over 2 steps). $^1$H NMR (400 MHz, $CDCl_3$) δ 5.20 (d, J=2.8 Hz, 1H, H-1α), 4.90-4.61 (m, 3H, H-1β, $COCH_2N$), 4.35-3.32 (m, 14H, H-2α-H-6α, H-2β-H-6β and $CH_2CH_3$), 2.53 (t, J=10.4 Hz, 2H, $PCH_2P$), 2.24 (s, 4H, 4×PH), 2.15-1.85 (m, 16H), 1.78 (d, J=10.1 Hz, 4H), 1.66-1.16 (m, 23H).

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A compound or salt of Formula VIII or a pharmaceutically acceptable salt thereof wherein $$Au_a(X)_x(Y)_y(W)_w(Z)_z \qquad \text{(Formula VIII)}$$

X is an aromatic or aliphatic phosphine of the following formulas 17-2
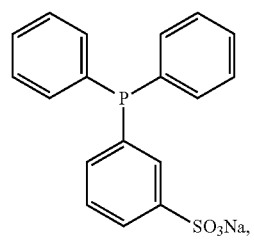

17-5
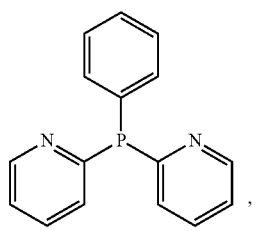

17-6
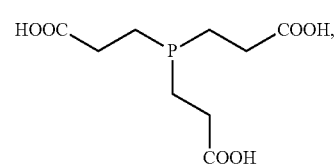

17-9
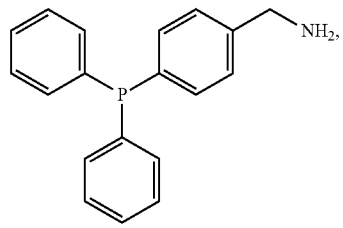

17-11
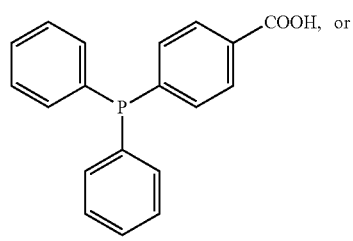

17-12
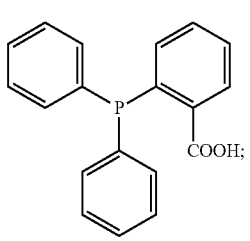

Y is a sugar;
W is —S$_2$C$_2$(CN)$_2$, —SC$_2$H$_5$, or —SC$_2$H$_4$Ph;
Z is NO$_3$ or halogen;
a is at least 10;
w is 0 to 14;
x is 1 to 14;
y is 0 to 14; and
z is 0 to 6.
2. The compound or salt of claim 1, wherein X is
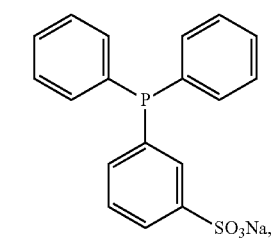
17-2
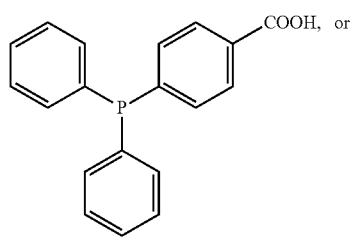
17-11
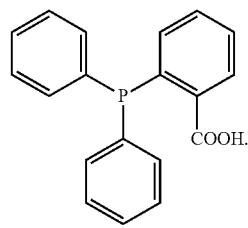
17-12
3. The compound or salt claim 1, wherein X is
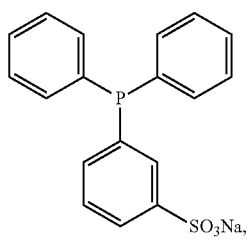
17-2
and Y is
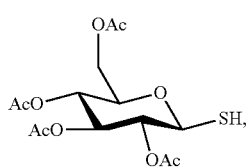
18-1
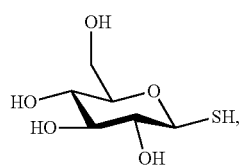
18-2
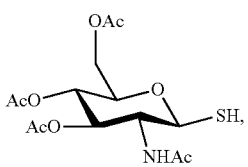
18-3
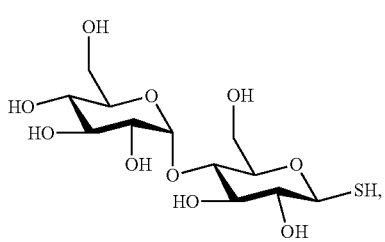
18-4
18-5
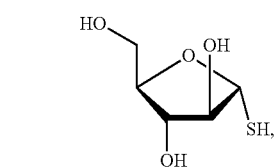
18-6
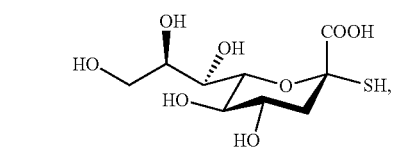
18-7
18-8
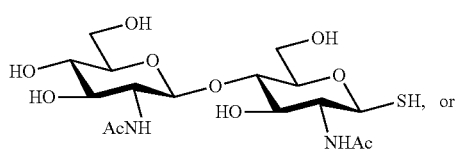
18-9

-continued
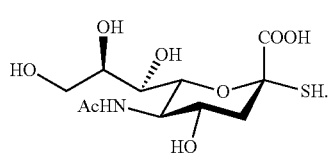
18-10
4. The compound or salt of claim 1, wherein the size of the compound is no more than 50 nanometers.
5. The compound or salt of claim 1, wherein the size of the compound is from 0.5 to 50 nanometers.
6. A pharmaceutical composition comprising a compound or salt of claim 1 together with a pharmaceutically acceptable carrier.
* * * * *